(12) United States Patent
Shi

(10) Patent No.: US 12,201,678 B2
(45) Date of Patent: *Jan. 21, 2025

(54) USE OF PERTUSSIS TOXIN AS A THERAPEUTIC AGENT

(71) Applicant: Dignity Health, San Francisco, CA (US)

(72) Inventor: Jiong Shi, Scottsdale, AZ (US)

(73) Assignee: Dignity Health, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/496,633

(22) Filed: Oct. 27, 2023

(65) Prior Publication Data

US 2024/0131119 A1 Apr. 25, 2024
US 2024/0226244 A9 Jul. 11, 2024

Related U.S. Application Data

(60) Division of application No. 17/083,032, filed on Oct. 28, 2020, now Pat. No. 11,833,191, which is a division of application No. 16/736,842, filed on Jan. 8, 2020, now Pat. No. 10,849,961, which is a continuation of application No. 15/782,151, filed on Oct. 12, 2017, now Pat. No. 10,596,233, which is a continuation-in-part of application No. 14/125,892, filed as application No. PCT/US2012/045065 on Jun. 29, 2012, now Pat. No. 9,801,921.

(60) Provisional application No. 61/503,491, filed on Jun. 30, 2011.

(51) Int. Cl.
| A61K 38/45 | (2006.01) |
| A61K 9/00 | (2006.01) |
| A61K 38/16 | (2006.01) |
| A61K 45/06 | (2006.01) |

(52) U.S. Cl.
CPC ............ *A61K 38/45* (2013.01); *A61K 38/164* (2013.01); *A61K 45/06* (2013.01); *C12Y 204/00* (2013.01); *C12Y 204/02031* (2013.01); *A61K 9/0019* (2013.01)

(58) Field of Classification Search
None
See application file for complete search history.

(56) References Cited

U.S. PATENT DOCUMENTS

| 5,858,965 | A | 1/1999 | Ben-Nun |
| 9,801,921 | B2 | 10/2017 | Shi |
| 10,596,233 | B2 | 3/2020 | Shi |
| 10,849,961 | B2 | 12/2020 | Shi |
| 2002/0142982 | A1 | 10/2002 | Hla et al. |
| 2002/0172687 | A1 | 11/2002 | Bukrinsky et al. |
| 2011/0044988 | A1 | 2/2011 | Bernhagen et al. |
| 2021/0069302 | A1 | 3/2021 | Shi |

FOREIGN PATENT DOCUMENTS

WO 2013003786 A1 1/2013

OTHER PUBLICATIONS

Patent Cooperation Treaty, International Search Report and Written Opinion, date of mailing Aug. 28, 2012, International Application No. PCT/US2012/045065, 3 pages.
Chung, KM et al., "Effects of intrathecal or incracerebroventricular pretreatment with pertussis toxin on antinociception induced by beta-endorphin or morphine adminstrered intracerebrobentricularly in mice" Naunyn Schmiedebergs Arch Pharmacol 349(6), Jun. 1994, pp. 588-593.
Yin, J. et al., "Centrally Administered Pertussis Toxin inhibits Microglia migration to the spinal cord and prevents dissemination of disease in an EAE model", PLoS ONE, vol. 5, Issue 8, Aug. 2010, pp. 1-14.
Tanaka et al., "Essential role of neutrophils in anti-type II collagen antibody and lipopolysaccharide-induced arthritis", Immunology, 119, May 26, 2006, pp. 195-202.
Weber et al., "Repetitive Pertussis Toxin Promotes Development of Regulatory T Cells and Prevents Central Nervous System Autoimmune Disease", PLoS ONE, vol. 5, Issue 12, e16009, Dec. 2010, pp. 1-9.
Kanwar, J. R. et al., "Recent Advances in the Treatment of Neurological Autoimmune Disorders", Recent Advances in the Treatment of Neurological Autoimmune Disorders, Nov. 14, 2011, pp. 289-323.
Biology Online, "Analog", http://www.biology-online.org/dictionary/Analog, accessed Dec. 7, 2014, 2 pages.
Biology Online, "Derivative", http://www.biology-online.org/dictionary/Derivative, accessed Dec. 7, 2014, 2 pages.
(http://www.fda.gov/ohrms/dockets/ac/05/briefing/2005-4137B1_07_Nomenclature.pdf) (accessed Dec. 7, 2014).
Medline Plus, "Neurologic Diseases", http://www.nlm.nih.gov/medlineplus/neurologicdiseases.html, accessed Dec. 7, 2014, 4 pages.
National Institute of Neurological Disorders and Stroke (NINDS) (accessed Dec. 7, 2014).
National Institute of Neurological Disorders and Stroke (NINDS), "Autism Information Page", http://www.ninds.nih.gov/disorders/autism/autism/htm, accessed Dec. 7, 2014, 4 pages.
National Institute of Neurological Disorders and Stroke (NINDS), "Amyotrophic Lateral Sclerosis (ALS) Information Page", http://www.ninds.nih.gov/disorders/amyotrophiclateralsclerosis/ALS.htm, accessed Dec. 7, 2014, 5 pages.
The Mayo Clinic, "HIV/AIDS", http://www.mayoclinic.org/diseases-conditions/hiv-aids/basics/complications/con-20013732, copyright 1998-2014, accessed Dec. 7, 2014, 3 pages.
Purves, D., et al., "G-Proteins and Their Molecular Targets", https://www.ncbi.nlm.nih.gov/books/NBK10832/, Neuroscience, 2nd Edition (2001), accessed Dec. 9, 2014, 3 pages.

(Continued)

*Primary Examiner* — Jeanette M Lieb
*Assistant Examiner* — Tara L Martinez
(74) *Attorney, Agent, or Firm* — Polsinelli PC

(57) ABSTRACT

The present application relates to the use of *pertussis* toxin, and its derivatives, analogs, salts and pharmaceutical equivalents. In one embodiment, the invention provides a method of treating or preventing a neurological disease or injury by administering *pertussis* toxin to the individual.

10 Claims, 37 Drawing Sheets

(56) References Cited

OTHER PUBLICATIONS

Perry et al. "Microglia and macrophages of the central nervous system: the contribution of microglia priming and systemic inflammation to chronic neurodegeneration" Semin Immunopathol, 35 (35), 2013, pp. 601-612.
Schwartz ("Macrophages and Microglia in Central Nervous System Injury: are they helpful or harmful" Journal of Cerebral Blood Flow and Metabolism, 23 395-394, 2003).
Yaldizli et al. "Natalizumab in the treatment of multiple sclerosis", Therapeutic Advances in Neurological Disorders 2 (2), 2009, pp. 115-128.
Canadian Office Action, Application Serial No. 2,831,154, issued Apr. 20, 2018, 5 pages.
Lu, C. et al., Journal of Neuroscience Research, "Pertussis Toxin Induces Angiogenesis in Brain Microvascular Endothelial Cells", Journal of Neuroscience Research vol. 86, Sep. 2008, pp. 2624-2640 (cited in Canadian Office Action).
Tang, Z. et al., "CXCR 1 deficiency suppresses activation and neurotoxicity of microglia/macrophage in experimental schemic stroke" Journal of Neuroinflammation vol. 11, Issue 26, 2014, pp. 1-13.
Tang, Z. et al., "Pertussis Toxin reduces calcium influx to protect ischemic stroke in a middle cerebral artery occlusion mode" Journal of Neurochemistry, vol. 135, 2015, pp. 998-1006.
Patent Cooperation Treaty, International Preliminary Report on Patentability, dated Jan. 7, 2014, International Application No. PCT/US2012/045065, 5 pages.

| | WT | EAE | EAE+PTx |
|---|---|---|---|
| CD3+ (x $10^5$) | 108.5±9.1 | 146.7±12.2* | 149.3±21.4* |
| CD4+ (x $10^5$) | 30.1±3.8 | 104.4±7.5* | 111.4±16.1* |
| CD8+ (x $10^5$) | 20.1±7.8 | 61.2±11.5* | 59.4±11.6* |
| CD4+/CD25+ (x $10^3$) | 55.9±6.8 | 63.9±7.8 | 53.9±10.9 |
| CD3-/CD19+ (x $10^5$) | 119.5±13.1 | 164.7±15.2* | 159.3±17.4* |
| CD45+/CD11b+ (x $10^3$) | 11.9±6.8 | 53.9±11.8** | 61.1±8.9** |

Figure 3
(Continued)

Cell number field

Brain-Iba-1

USE OF PERTUSSIS TOXIN AS A THERAPEUTIC AGENT

CROSS-REFERENCE TO RELATED APPLICATIONS

This application is a divisional of U.S. application Ser. No. 17/083,032, which is a divisional of U.S. application Ser. No. 16/736,842, filed Jan. 8, 2020, now U.S. Pat. No. 10,849,961, which is a continuation of U.S. application Ser. No. 15/782,151, filed on Oct. 12, 2017, now U.S. Pat. No. 10,596,233, which is a continuation-in-part of U.S. application Ser. No. 14/125,892, filed Dec. 12, 2013, now U.S. Pat. No. 9,801,921, which claims benefit of International Application PCT/US2012/045065, filed Jun. 29, 2012, which claims benefit from U.S. Provisional Application Ser. No. 61/503,491, filed on Jun. 30, 2011, which is incorporated by reference in its entirety.

FIELD OF THE INVENTION

The invention relates generally to the field of medicine and neurology and autoimmunity and, more specifically, to *pertussis* toxin and methods of treating and preventing neurological and autoimmune diseases and conditions such as multiple sclerosis and stroke (e.g., ischemic stroke).

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Multiple sclerosis (MS), or disseminated sclerosis or encephalomyelitis disseminata is a neurological and autoimmune disease where myelin sheaths around axons of the brain and spinal cord are damaged. The result is difficulty for nerve cells in the brain and spinal cord to effectively communicate with each other. Various neurological symptoms can occur, often progressing into physical and cognitive disability, until often permanent neurological problems occur as the disease advances. The disease affects 2.5 million people and life expectancy of those with MS is about 5 to 10 years lower than the normal population. At present, the exact cause of MS is unknown, although experimental autoimmune encephalomyelitis (EAE) is the primary animal model used to study MS. Unfortunately, there is no known cure for MS, and MS medications often have adverse effects. Thus, there is a great need in the art for novel and effective treatments for neurological and autoimmune diseases such as multiple sclerosis.

Similarly, stroke is a leading cause of disability and death in the United States and other developed countries. Advances in the understanding of the pathophysiology of stroke have generated a plethora of new investigative studies in the treatment of stroke; however there has been little success in the clinical translation of the findings from these studies. Moreover, ischemic brain injuries, such as those caused by strokes, often elicit an inflammatory response that involves activation and migration of microglia and monocyte-derived macrophages in the central nervous system. Within and adjacent to these injury sites, these immune cells adopt unique phenotypes with either protective or detrimental effects on neuron survival. Thus, there is a great need in the art for novel and effective treatments and protective compounds for neurological diseases and disorders, such as ischemic brain injuries caused by stroke.

SUMMARY OF THE INVENTION

Various embodiments herein include a method of treating and/or ameliorating the effects of a neurologic disease in a subject, comprising providing a composition comprising *pertussis* toxin (PTx), or a derivative, analog, pharmaceutical equivalent, and/or salt thereof, and treating and/or ameliorating the effects of the neurologic disease by administering a therapeutically effective dosage of the composition comprising *pertussis* toxin (PTx), or a derivative, analog, pharmaceutical equivalent, and/or salt thereof to the subject. In another embodiment, the neurologic disease is multiple sclerosis. In another embodiment, the neurologic disease is Systemic lupus erythematosus (SLE), Rheumatoid arthritis and Wegener's granulomatosis, complications related to the Human Immunodeficiency Virus (HIV), Guillain-Barre syndrome, meningitis, Alzheimer's disease, dementia, or Parkinson's disease. In another embodiment, the subject is a human. In another embodiment, the subject is a mouse or rat. In another embodiment, the composition is administered intracerebroventricularly (icv) or intraperitoneally (ip). In another embodiment, ameliorating the effects of the neurologic disease in the subject includes mitigating clinical motor symptoms, minimizing T cell infiltration, and/or preventing demyelination of the spinal cord. In another embodiment, administering the composition results in inhibition of migration of microglia in the subject. In another embodiment, the composition is administered to the subject in conjunction with G-protein, chemokine and/or adhesion blocking agents. In another embodiment, administering the composition results in increased vascular endothelial growth factor (VEGF) expression on neurons and/or increased angiogenesis. In another embodiment, administering the composition results in increased blood vessel density in brain cortex and/or spinal gray matter. In another embodiment, the therapeutically effective dosage comprises at least 500 ng PTx. In another embodiment, the therapeutically effective dosage comprises at least 1000 ng PTx.

Other embodiments include a method of protecting against a neurologic disease in a subject, comprising providing a composition comprising *pertussis* toxin (PTx), or a derivative, analog, pharmaceutical equivalent, and/or salt thereof, and protecting against the neurologic disease by administering a therapeutically effective dosage of the composition comprising *pertussis* toxin (PTx), or a derivative, analog, pharmaceutical equivalent, and/or salt thereof to the subject. In another embodiment, the neurologic disease is multiple sclerosis. In another embodiment, the neurologic disease is a central nervous system autoimmune disease. In another embodiment, the neurologic disease is Systemic lupus erythematosus (SLE), Rheumatoid arthritis and Wegener's granulomatosis, complications related to the Human Immunodeficiency Virus (HIV), Guillain-Barre syndrome, meningitis, Alzheimer's disease, dementia, or Parkinson's disease. In another embodiment, the subject is a human. In another embodiment, the subject is a mouse or rat. In another embodiment, the composition is administered intracerebroventricularly (icv) or intraperitoneally (ip). In another embodiment, administering the composition results in inhibition of migration of microglia in the subject. In another embodiment, administering the composition results in increased vascular endothelial growth factor (VEGF) expression on neurons and/or increased angiogenesis. In another embodiment, the therapeutically effective dosage comprises at least 500 ng PTx. In another embodiment, the therapeutically effective dosage comprises at least 1000 ng PTx.

Other embodiments include a pharmaceutical composition, comprising a therapeutically effective amount of *pertussis* toxin (PTx), or a derivative, analog, pharmaceutical equivalent, and/or salt thereof, and a pharmaceutically acceptable carrier. In another embodiment, the therapeutically effective amount of PTx is about 1000 ng PTx.

Some embodiments include a method of reducing T cell infiltration into a neurological tissue in a human subject. For example, the method may include providing a composition comprising *pertussis* toxin (PTx) comprising subunits A and B and administering (e.g., intracerebroventricularly (icv) or intraperitoneally (ip)) a therapeutically effective dosage of the composition to the human subject. In some aspects, the neurological tissue may comprise brain tissue that has undergone an ischemic brain injury resulting from a stroke (e.g., an ischemic stroke). In some embodiments, the administration may also result in the inhibition of migration of microglia in the human subject (e.g., migration to the site of injury).

In another embodiment, the composition is administered to the subject in conjunction with G-protein, chemokine and/or adhesion blocking agents. In another embodiment, administering the composition results in increased vascular endothelial growth factor (VEGF) expression on neurons and/or increased angiogenesis. In another embodiment, administering the composition results in increased blood vessel density in brain cortex and/or spinal gray matter. In another embodiment, the therapeutically effective dosage comprises at least 500 ng PTx. In another embodiment, the therapeutically effective dosage comprises at least 1000 ng PTx.

Some other embodiments may provide a method of protecting against an occurrence of stroke (e.g., an ischemic stroke) in a human subject at risk therefore. For example, the method may comprise the steps of: providing a composition comprising *pertussis* toxin (PTx) comprising subunits A and B and administering (e.g., intracerebroventricularly (icv) or intraperitoneally (ip)) a therapeutically effective dosage of the composition to the human subject. In some aspects, administration of the composition may result in inhibition of migration of microglia and T cell infiltration to the site of the ischemic stroke.

Some embodiments may provide a method of reducing migration of microglia to a site of brain injury (e.g., caused by an ischemic stroke) in a human subject. For example, the method may comprise the steps of providing a composition comprising *pertussis* toxin (PTx) comprising subunits A and B and administering (e.g., intracerebroventricularly (icv) or intraperitoneally (ip)) a therapeutically effective dosage of the composition to the human subject. Moreover, in some embodiments, administration of the composition may also inhibit migration of T cells to the site of the brain injury.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

DETAILED DESCRIPTION OF THE INVENTION

Figure 1:
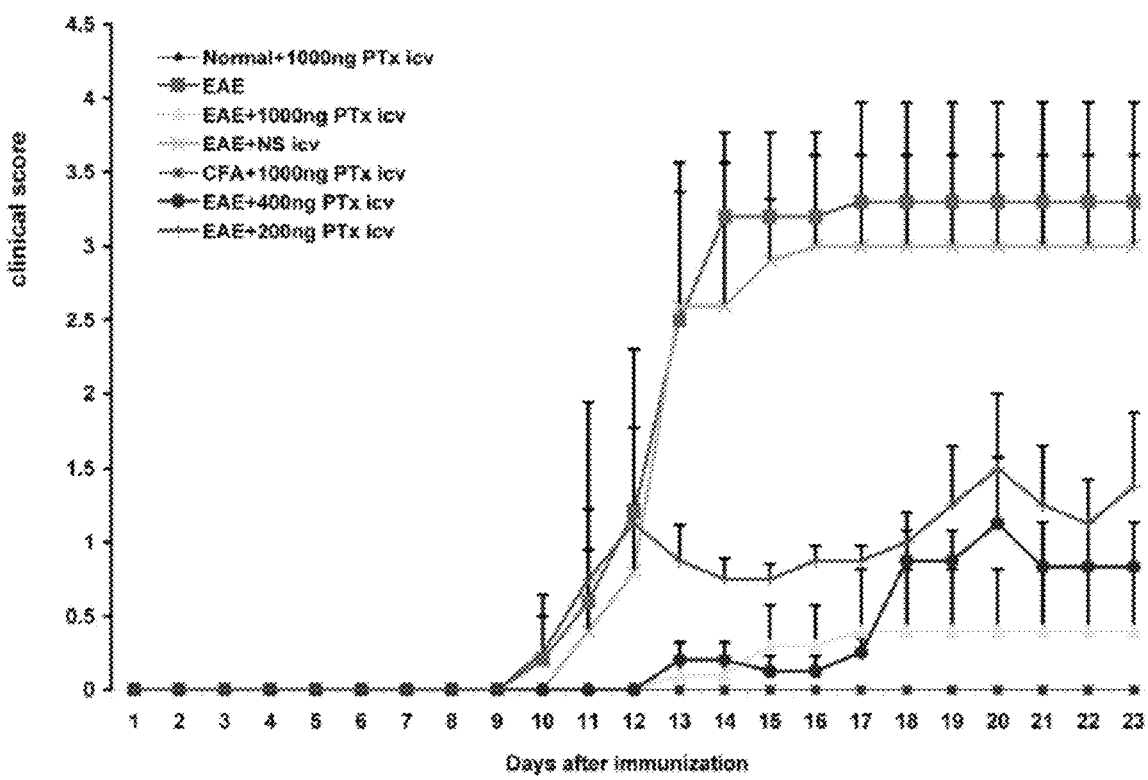
FIG. 1 depicts EAE+PTx icv mice developed an attenuated and delayed course of EAE. Clinical scores were evaluated daily in EAE+PTx icv and control mice and were plotted as the mean 6 S.D (n=12/group). Maximum clinical scores as well as scores on day 14 and 23 evidence marked attenuation of disease severity after PTx icv (P,0.01). A dose response to PTx icv is demonstrated as well. Mice receiving lower doses of PTx icv (400 ng and 200 ng) continued to manifest a dose dependent benefit compared to the EAE controls (P,0.05).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, NY 2001); March, Advanced Organic Chemistry Reactions, Mechanisms and Structure 5th ed., J. Wiley & Sons (New York, NY 2001); and Sambrook and Russel, Molecular Cloning: A Laboratory Manual 3rd ed., Cold Spring Harbor Laboratory Press (Cold Spring Harbor, NY 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As disclosed herein, the inventors investigated the effects of *Pertussis* toxin (PTx) administered intracerebroventricularly (icv) as well as intraperitoneally (ip) in preventing downstream immune cell infiltration and demyelination of the spinal cord. EAE was induced in C57BL/6 mice with MOG35-55. PTx icv at seven days post MOG immunization resulted in mitigation of clinical motor symptoms, minimal T cell infiltration, and the marked absence of axonal loss and demyelination of the spinal cord. Integrity of the blood brain barrier was compromised in the brain whereas spinal cord BBB integrity remained intact. PTx icv markedly increased microglia numbers in the brain preventing their migration to the spinal cord. An in vitro transwell study demonstrated that PTx inhibited migration of microglia. Centrally administered PTx abrogated migration of microglia in EAE mice, limiting the inflammatory cytokine milieu to the brain and prevented dissemination of demyelination.

As further disclosed herein, the inventors have provided evidence of the usage of PTx as a therapeutic agent to treat autoimmune disease, and provide insight into the etiological mechanism of autoimmune diseases and provide a therapeutic model demonstrating attenuation of the lesion and clinical manifestations of EAE with early administration of icv and ip PTx. Understanding the mechanism of PTx allows implementation of other directed methods to mimic the effects of PTx therapeutically utilizing G protein, chemokine, and adhesion blocking agents. In addition, the design and development of effective treatment strategies surrounding the unique concept of translocated inflammation provide further insight into the mechanism of therapies. By applying PTx, the inventors successfully attenuate the motor deficits in EAE. Beyond its implications for multiple sclerosis, the understanding of microglia and T cell translocation in central nervous system (CNS) and the manipulation of its regulation have a broad impact in other autoimmune diseases such as Systemic lupus erythematosus (SLE), Rheumatoid arthritis and Wegener's granulomatosis as well as infectious disorders affecting the immune system such as HIV, Guillain-Barre syndrome and meningitis. Finally, in light of the role of immune modulation in the effective treatment of neurodegenerative diseases, there is also an impact on neurodegenerative diseases such as Alzheimer's and Parkinson's disease and the continuum between immunologic disease and neurodegeneration.

As further disclosed herein, the inventors have provided evidence of the usage of PTx to treat and or prevent one or more insults or injuries to the neurological system. For example, in some embodiments, the treatment and/or prevention of the one or more insults or injuries to the neurological system may be provided via administering a therapeutically effective dosage of a composition comprising *pertussis* toxin (PTx), including subunits A and B, or a derivative, analog, pharmaceutical equivalent, and/or salt, thereof to the subject. In some embodiments, the one or more insults or injuries to the neurological system may comprise an ischemic brain injury, such as a brain injury caused by a stroke. As such, administration of PTx may prevent or treat ischemic brain injuries arising from an ischemic stroke in a human subject. For example, prior to or after the occurrence of an ischemic brain injury, administration of PTx may reduce and/or eliminate one or more signs of an inflammatory response.

In some embodiments, PTx may be administered to individuals at risk for a first ischemic brain injury or may have already suffered a first ischemic brain injury and may be at risk for subsequent ischemic brain injuries. In some aspects, an individual/subject who has not previously suffered an ischemic brain injury, such an as ischemic stroke, may be determined by a healthcare provider to be a risk for experiencing an ischemic brain injury (e.g., via an evaluation of current state of health, personal health history, family health history, environmental factors, genetic factors, etc.). As such, according to some embodiments, a therapeutically effective amount of a composition comprising PTx can be administered to the subject at risk for the stroke to prevent the occurrence of the stroke. In other aspects, the subject may have already suffered from one or more ischemic brain injuries, such as a stroke, such that the subject may be at an increased risk of addition strokes. In such circumstances, the composition comprising a therapeutically effective amount of PTx may also be administered to the subject at risk to reduce the risk of, and protect against the occurrence of a stroke in the subject.

In some aspects, administration of PTx may reduce infiltration/migration of one or more types of leukocytes, such as T cells and microglia to the site of the ischemic injury, such as the brain or immediately adjacent tissues. As such, the potentially harmful inflammatory response may be blunted to reduce the likelihood of the occurrence of the ischemic brain injury or treat the resulting injury if administered after occurrence.

In one embodiment, the present invention provides a method of treating a disease or disorder in a subject by administering a therapeutically effective dosage of a composition comprising *pertussis* toxin (PTx), or a derivative, analog, pharmaceutical equivalent, and/or salt, thereof to the subject. In another embodiment, the present invention provides a method of mitigating the effects of and/or slowing progression of the disease by administering a therapeutically effective dosage of a composition comprising *pertussis* toxin (PTx), or a derivative, analog, pharmaceutical equivalent, and/or salt, thereof to the subject. In another embodiment, the administration of the composition prevents and/or reduces the likelihood of susceptibility to developing the disease relative to a healthy individual. In another embodiment, the subject is a mouse. In another embodiment, the subject is a human. In another embodiment, the disease is a neurodegenerative disease, including for example, Alzheimer's disease, dementia, and Parkinson's disease. In one embodiment, the disease or disorder is an ischemic brain injury, such as an ischemic injury caused by a stroke. In another embodiment, the disease is an autoimmune disease, including but not limited to acute demyelinating encephalomyelitis, multiple sclerosis, and systemic lupus erythematosus, Rheumatoid arthritis, and Wegener's granulomatosis. In another embodiment, administering the composition results in inhibition of migration of microglia (e.g., to the site of the ischemic injury caused by a stroke). In another embodiment, administering the composition results in increased vascular endothelial growth factor (VEGF) expression on neurons and/or increased angiogenesis. In another embodiment, the therapeutically effective dosage comprises at least 1000 ng PTx. In another embodiment, the disease is an infectious disorder affecting the immune system such as but not limited to HIV, Guillain-Barre syndrome and meningitis. In another embodiment, the invention may provide treatment for inflammatory spinal cord injury. In another embodiment, the treatment may be administered intracerebroventricularly (icv) and/or intraperitoneally (ip).

In another embodiment, the present invention provides a composition comprising a therapeutically effective dosage of *pertussis* toxin (PTx), or a pharmaceutical equivalent, analog, derivative, and/or salt thereof, and a pharmaceutically acceptable carrier. In another embodiment, the therapeutically effective dosage is about 1000 ng PTx.

In some embodiments of the invention, the effective amount of *pertussis* toxin (PTx), or a pharmaceutical equivalent, analog, salt, and/or derivative in the composition can be in the range of about 10-100 ng, 100-200 ng, 200-300 ng, 300-400 ng, 400-500 ng, 500-600 ng, 600-700 ng, 700-800 ng, 800-900 ng, 900-1000 ng, 1000-1100 ng, 1100-1200 ng, 1200-1300 ng, 1300-1400 ng, 1400-1500 ng, 1500-1600 ng, 1600-1700 ng, 1700-1800 ng, 1800-1900 ng, 1900-2000 ng, 2000-2100 ng, 2100-2200 ng, 2200-2300 ng, 2300-2400 ng, 2400-2500 ng, 2500-2600 ng, 2600-2700 ng, 2700-2800 ng, 2800-2900 ng, or 2900-3000 ng.

In some embodiments of the invention, the effective amount of *pertussis* toxin (PTx), or a pharmaceutical equivalent, analog, salt, and/or derivative in the composition can be in the range of about 10-100 ng/day, 100-200 ng/day, 200-300 ng/day, 300-400 ng/day, 400-500 ng/day, 500-600 ng/day, 600-700 ng/day, 700-800 ng/day, 800-900 ng/day, 900-1000 ng/day, 1000-1100 ng/day, 1100-1200 ng/day, 1200-1300 ng/day, 1300-1400 ng/day, 1400-1500 ng/day, 1500-1600 ng/day, 1600-1700 ng/day, 1700-1800 ng/day, 1800-1900 ng/day, 1900-2000 ng/day, 2000-2100 ng/day, 2100-2200 ng/day, 2200-2300 ng/day, 2300-2400 ng/day, 2400-2500 ng/day, 2500-2600 ng/day, 2600-2700 ng/day, 2700-2800 ng/day, 2800-2900 ng/day, or 2900-3000 ng/day.

In some embodiments of the invention, the effective amount of *pertussis* toxin (PTx), or a pharmaceutical equivalent, analog, salt, and/or derivative in the composition can be in the range of about 10-100 mg, 100-200 mg, 200-300 mg, 300-400 mg, 400-500 mg, 500-600 mg, 600-700 mg, 700-800 mg, 800-900 mg, 900-1000 mg, 1000-1100 mg, 1100-1200 mg, 1200-1300 mg, 1300-1400 mg, 1400-1500 mg, 1500-1600 mg, 1600-1700 mg, 1700-1800 mg, 1800-1900 mg, 1900-2000 mg, 2000-2100 mg, 2100-2200 mg, 2200-2300 mg, 2300-2400 mg, 2400-2500 mg, 2500-2600 mg, 2600-2700 mg, 2700-2800 mg, 2800-2900 mg, or 2900-3000 mg.

Typical dosages of an effective amount of *pertussis* toxin (PTx), or a pharmaceutical equivalent, analog, salt, and/or derivative can be in the ranges recommended by the manufacturer where known therapeutic compounds are used, and also as indicated to the skilled artisan by the in vitro responses or responses in animal models. For example, one of skill in the art may readily calculate and prepare the equivalent dosages of PTx for human patients based on an effective dosage of 1000 ng/day administered to a mouse model. The same or similar dosing can be used in accordance with various embodiments of the present invention, or an alternate dosage may be used in connection with alternate embodiments of the invention, such as administrating in conjunction with or without various G-proteins, chemokines and/or adhesion blocking agents. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models.

As readily apparent to one of skill in the art, various embodiments described herein may be used to treat any number of conditions and diseases that affect the central nervous system, motor deficits, spinal cord injury and/or inflammation, and demyelination, and the invention is not in any way limited to only treatment of multiple sclerosis. Similarly, as described herein, the inventors have determined that *pertussis* toxin may be distinguished from other possible therapeutic lesions by mediating therapeutic effects immunologically, as opposed to being neurotransmitter driven. Thus, as readily apparent to one of skill in the art, any number of additional compositions or substitutes may also act through a similar mechanism, including pharmaceutical equivalents, derivatives, analogs, and/or salts, or other compounds and agents that mimic *pertussis* toxin's therapeutic utilization of G protein, chemokine and adhesion blocking, and the invention is not limited only to *pertussis* toxin itself.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

Experimental autoimmune encephalomyelitis (EAE) models are important vehicles for studying the effect of infectious elements such as *Pertussis* toxin (PTx) on disease processes related to acute demyelinating encephalomyelitis (ADEM) or multiple sclerosis (MS). PTx has pleotropic effects on the immune system. The inventors investigated the effects of PTx administered intracerebroventricularly (icv) in preventing downstream immune cell infiltration and demyelination of the spinal cord.

Methods and Findings: EAE was induced in C57BL/6 mice with MOG35-55. PTx icv at seven days post MOG immunization resulted in mitigation of clinical motor symptoms, minimal T cell infiltration, and the marked absence of axonal loss and demyelination of the spinal cord. Integrity of the blood brain barrier was compromised in the brain whereas spinal cord BBB integrity remained intact. PTx icv markedly increased microglia numbers in the brain preventing their migration to the spinal cord. An in vitro transwell study demonstrated that PTx inhibited migration of microglia.

Centrally administered PTx abrogated migration of microglia in EAE mice, limiting the inflammatory cytokine milieu to the brain and prevented dissemination of demyelination. The effects of PTx icv warrants further investigation and provides an attractive template for further study regarding the pleotropic effects of infectious elements such as PTx in the pathogenesis of autoimmune disorders.

Example 2

EAE Induction and Treatment

The animals were kept in groups on a 12:12 h light/dark cycle with food and water ad libitum. EAE was induced in female C57BL/6 mice (6-8 weeks old, Taconic Laboratory, New York, USA) by subcutaneous injection with 200 mg myelin oligodendrocyte glycoprotein (MOG35-55; M-E-V-G-W-Y-R-S-P-F-S-R-V-V-H-L-Y-R-N-G-K, Bio-synthesis Inc. Lewisville, TX), dissolved in an emulsion of 50 ml of complete Freund's adjuvant containing 0.5 mg of heat killed *Mycobacterium tuberculosis* (CFA, Difco Laboratories, Detroit, MI) and 50 ml of phosphate buffered saline (PBS). On the day of immunization (day 0) and 48 h later (day 2), PTx (List Biological laboratories Inc.) 200 ng in PBS was injected into the mouse tail vein. Neurological functional tests were performed by an examiner blinded to the treatment status of each animal. Functional data were collected on 7 mouse groups (n=12/group), 3 PTx icv treatment groups (EAE+PTx icv 1000 ng, 400 ng, and 200 ng), 2 EAE groups (EAE and EAE+ normal saline (NS) icv) and 2 non-EAE control groups (normal+1000 ng PTX icv and CFA+1000 ng PTX icv). Neurological assessments were reported using a five-point standardized rating scale to evaluate motor deficit: 0 no deficit; 1 tail paralysis; 2 unilateral hind limb weakness; 3 incomplete bilateral hind limb paralysis and/or partial forelimb weakness; 4 complete hind limb paralysis and partial forelimb weakness; 5 moribund state or death. Scores were measured daily for 23 days. The onset of disease was calculated by determining the total number of days from MOG35-55 immunization to the onset of symptoms in individual animals. Maximal motor scores and motor scores at day 14 and 21 were compared as were onset of disease.

Example 3

Stereotactic Intracerebroventricular Injection

Mice were anaesthetized by injection of a ketamine/xylamine cocktail on day 7 after MOG35-55 immunization and mounted in a stereotactic device. A fine hole was drilled through the skull giving access to the surface of the brain 0.7 mm caudal to bregma and 1.0 mm lateral to the sagittal suture. A guarded, 27-gauge 0.5-in needle was stereotactically inserted, targeting the lateral ventricle (3.5 mm depth). A 10.0-ml Hamilton 1700 series gastight syringe was used to inject 2 ml of normal saline, or PTx (500 mg/ml dissolved in normal saline) into the lateral ventricle over a five-minute period.

Example 4

Immunohistochemistry

Mice were euthanized at day 7 14 or day 23 post immunization. Terminally anesthetized mice were intracardiacally perfused with saline followed by 4% paraformaldehyde. The spinal cord and brain were embedded in paraffin and cut into serial 6-mm thick coronal slides. Histological evaluation was performed by staining with hematoxylin and eosin (H&E), Luxol fast blue/periodic acid Schiff agent (LFB/PAS), and Bielschowsky silver impregnation to assess inflammation, demyelination, and axonal pathology, respectively. Histological scores assessing the degree of inflammation, demyelination, and axonal loss in the spinal cord were evaluated using a semi-quantitative system. In brief, the degree of inflammation was assessed by counting the number of cellular infiltrates in the spinal cord. Digital images were collected using an Axoplan microscope (Zeiss, Thornwood, NY) under bright field setting using a 40× objective. Severity of inflammatory cell infiltration on H&E staining was scored using the following scale: 0, no inflammation; 1, cellular infiltrates only around blood vessel and meninges; 2, mild cellular infiltrates in parenchyma (1-10/section); 3, moderate cellular infiltrates in parenchyma (11-100/section); and 4, serious cellular infiltrates in parenchyma (0.100/section). Serial sections of paraformaldehyde-fixed spinal cord were stained with Luxol fast blue for myelin and were assessed in a blinded fashion for demyelination using the following scale: 0, normal white matter; 1, rare foci; 2, a few areas of demyelination; 3, confluent perivascular or subpial demyelination; 4, massive perivascular and subpial demyelination involving one half of the spinal cord with presence of cellular infiltrates in the CNS parenchyma; and 5, extensive perivascular and subpial demyelination involving the whole cord section with presence of cellular infiltrates in the CNS parenchyma. Axonal loss was assessed using the following scale: 0, no axonal loss; 1, a few foci of superficial axonal loss which involves less than 25% of the lateral columns; 2, foci of deep axonal loss and that encompasses over 25% of the lateral columns; and 3, diffuse and widespread axonal loss. At least six serial sections of each spinal cord from each mouse were scored and statistically analyzed by ANOVA. Data were presented as Mean 6 Standard deviation (SD). Immunohistochemistry was performed with rabbit polyclonal antibodies against IL-6 (1:2000, #ab6672, Abcam Inc; Cambridge, MA), and TGF-b (1:3000, #ab66043, Abcam Inc; Cambridge, MA) to identify crucial pro-inflammatory cytokines; and against ionized calcium binding adaptor molecule 1 (Iba-1, 1:2500, Wako Chemicals Inc. LA) for microglia and glia fibrillary acidic protein (GFAP, 1:400, Millipore Corporation, Billerica, MA) for astrocytes. Sections of brain and spinal cord stained with anti-Iba1 allowed quantification of microglia and assessment of its morphology. The inventors performed a morphological analysis of the changes observed and quantified the microglia in sections of cerebral cortex and spinal cord. Th17 cells were identified by double immunostaining for CD4 (1:1600, Chemicon, Temecula, CA), and IL-17 (1:3000, rabbit mAb, #ab40663, Abcam Inc., Cambridge, MA) with two fluorescent conjugated secondary antibodies (FITC conjugated and Texas Red conjugated). Immunolabeling was detected by applying the peroxidase-antiperoxidase procedure with 3, 39-diaminobenzidine (DAB) as cosubstrate. Negative control slides received identical preparations for immunostaining, except that primary antibodies were omitted.

Example 5

Western Blot Protein Analysis

Aliquots of equal amount of proteins were loaded onto a 10% SDS-polyacrylamide gel. After gel electrophoresis, blots were subsequently probed with primary antibodies (anti-IL-6, 1:1000 #ab6672, anti-IL-17, 1:3000 #ab40663, anti-TGF-b 1:1000 #ab66043 Abcam Inc; Cambridge, MA). For detection, horseradish peroxidase-conjugated secondary anti-rabbit antibody was used (1:10,000, #7074, Cell signaling technology; Danvers, MA), followed by enhanced chemiluminescence development (ECL kit, #34077, Thermo Scientific Pierce, Rockford IL). Normalization of results was ensured by running parallel Western blots with b-actin antibody (1:25,000 #ab49900, Abcam Inc; Cambridge, MA). The optical density was quantified using an image densitometer (Model GS-670, BioRad, Hercules, CA). The data are presented as a percentage of target protein relative to b-actin. A value of p,0.05 is considered significant.

Example 6

BBB Studies

Qualitative (immunohistochemistry) and quantitative (Western blot) analyses of exogenous rabbit IgG penetration across the BBB into the CNS were used to evaluate the extent of regional breakdown of the BBB in EAE and EAE+PTx icv mice [20]. Normal and PTx icv (without EAE) were used as controls. Mice were injected intraperitoneally (i.p.) with 100 mg purified rabbit IgG (Ir—Rb-Gf, Innovative research, Novi, MI, USA) on day 7 (four hours after PTx icv in the EAE+PTx icv group) or day 14. Animals were euthanized 18-19 hours after the injection. For immunohistochemistry, paraffin embedded sections were probed directly with biotinylated anti-rabbit IgG (1:100; Vector laboratories, Brulingame, CA). For Western blot, the horseradish peroxidase-labeled anti-rabbit antibody (1:5000, Cell Signaling Technology, Davers, MA) was used.

Example 7

T Cell Proliferation Assays

Animals were sacrificed on day 14. Mononuclear cells were isolated from the spleen and were suspended in culture medium containing DMEM supplemented with 1% penicillin-streptomycin and 10% (v/v) FBS (Invitrogen Life Technologies). Mononuclear cells were then seeded onto 96-well plates at a concentration of 46105 cells/well. Ten microliters of MOG35-55 peptide (10 mg/ml), PLP139-151 peptide (10 mg/ml), or Con A (5 mg/ml; Sigma-Aldrich) were then added in triplicate into the wells. After 3 days of incubation, the cells were pulsed for 18 h with 10-ml aliquots containing 1 mCi of [methyl-3H] thymidine (42 Ci/mmol; Amersham Biosciences). Cells were harvested onto glass fiber filters, and the thymidine incorporation was measured. The results were expressed as Dcpm (DCPM) (mean cpm stimulated cultures—mean cpm unstimulated cultures).

Example 8

Flow Cytometry Analysis

To evaluate the frequency of CD4+, CD8+, CD4+/CD25+, CD32/CD19+, CD45+/CD11b+ cells, spleen mononuclear cell culture was prepared from each group on day 14 (the peak of autoimmune response). Single cell suspensions (26106 cells/5 ml BD tube) were incubated with combinations of fluorescent antibodies, for 30 min at 4 uC: CD3 (17A2), CD19 (1D3), CD4 (GK 1.5), CD8 (53-6.7), CD25 PC61.5), CD11b (M1/70), and CD45 (RA3-6B2). The indicated antibodies were fluorescently tagged with either FITC, PE, allophycocyanin, PE-Cy5, PE-Cy7 or APC-Cy7. All purchased from BD Pharmingen. After incubation, each suspension was washed twice (400 g, 5 min, 4 uC) with PBS containing 2% bovine serum albumin (BSA) and was resuspended in PBS with 0.5% of paraformaldehyde. Appropriate isotype controls were included. All samples were analyzed on Accuri C6 Flow Cytometer (Accuri Cytometers Inc, USA). Data were analyzed on CFlow Plus software. The number of mononuclear cells per mouse spleen was counted on hemocytometer and the absolute number of a cell subset was calculated based on the percentage of cells stained for the appropriate markers.

Example 9

Cytokine Quantification by Enzyme-Linked Immunosorbent Assay (ELISA)

To assess cytokine expression, spleen mononuclear cells were prepared as described above. Suspensions were incubated in RPMI-1640 medium at 37 uC for 2 days (26106 cells/well) with or without antigens (MOG35-55 10 mg/ml or Con A 5 mg/ml, Sigma, USA). Supernatants were collected and aliquoted in 96-well plate precoated with antibodies to Interferon c (IFN-c), Tumor Necrosis Factor a (TNF-α), Interleukin-2 (IL-2), Interleukin-4 (IL-4), Interleukin-6 (IL-6) and Interleukin-10 (IL-10) (ELISA Max™ Set Deluxe, BioLegend Inc. San Diego, CA). Optical density was measured at 450 nm on Model 680 Microplate Reader (Bio-Rad Laboratories, Corston, UK). The optical density was quantified by GraphPad Prism 4 (GraphPad Software, Inc) using the standard curve provided by the manufacturer.

Example 10

Primary Microglia Cell Culture

Cortical tissue was harvested from 0 or 1-day-old C57/BL6 mouse pups (Taconic, Hudson, NY). Meninges and visible vasculature were removed under a dissecting microscope. Cortical tissue was digested in the DMEM/F12 media (Invitrogen Corporation, CA) containing 0.25% trypsin and EDTA (1 mM) at 37 uC for 15 minutes. The digested tissue was resuspended in 20 ml media containing DMEM/F12 supplemented with 15% heat inactivated fetal bovine serum, 5% Horse serum (Sigma, St. Louis, MO) and 1% Penicillin-Streptomycin and filtered through a 70-mm nylon mesh (BD Biosciences, San Jose, CA). The cells were washed and seeded in a 75 cm2 flask in fresh culture medium (3-4 Pups/per flask). The purity of the microglia cultures was assessed by double-immunostaining with microglial special markers anti Ionized calcium binding adaptor molecule 1 (Iba-1, 1:2500, Wako Chemicals Inc. LA) and glia fibrillary acidic protein (GFAP, 1:400, Millipore Corporation, Billerica, MA). The purity of this primary microglia cell culture is about 90-95%.

Example 11

Microglia Migration Assay

The migration of microglia in vitro was determined by using Transwell (pore size 8-mm, Corning, VWR, San Dimas, CA). Cellfree DMEM/F-12 media (0.8 ml) with or without IFN-c (20 ng/ml, BD Biosciences, San Jose, CA) was placed in the lower chamber. Microglia suspension (0.1 ml, 56104 cell/per well) was placed in upper chamber and incubated with or without PTx (100 ng/ml, Campbell, CA) for 24 hours at 37 uC. The inserts were then removed and the upper surface was carefully cleansed with cotton pads. Cells on the lower surface were air dried and stained for microglia. Microglial migration was quantified and compared among the groups by counting the number of cells that migrated through the membrane to the lower chamber. Five random fields at 40× fields were counted for each condition under a phase contrast microscope. Each experiment was repeated three times. Results were shown as the cells counted per 40× field.

Example 12

Statistical Analysis

Data were analyzed with SPSS version 10 for windows. The two way analysis of variance was applied to determine the significance of the difference among the experimental groups. Kruskal-Wallis nonparametric analysis was used for data presented as percentage. The Mann-Whitney U test was used when Kruskal-Wallis showed significance among groups. P,0.05 was considered significant.

Example 13

Results—Table 1

TABLE 1

Splenocytes from EAE and EAE + PTx mice expressed elevated levels of TNF-α, IFN-γ, IL-2, IL-6, and IL-4 compared to WT controls.

| Pg/ml | WT | EAE | EAE + PTx |
|---|---|---|---|
| TNF-α | 3.0 +/− 0.9 | 46.7 +/− 2.0* | 49.3 +/− 1.9* |
| IFN-γ | 9.9 +/− 8.9 | 2385.9 +/− 556.9* | 2636.2 +/− 186.9* |
| IL-2 | 5.4 +/− 0.6 | 105.9 +/− 26.0* | 138.2 +/− 23.1* |
| IL-6 | 14.1 +/− 3.8 | 1144.0 +/− 211.5* | 1047.0 +/− 186.1* |
| IL-4 | 1.3 +/− 0.4 | 170.9 +/− 62.5* | 144.3 +/− 11.3* |

There was no significant differences in cytokine production in EAE and EAE + PTx.
*P, 0.001, compared with WT.
Abbreviation:
WT: wild type,
EAE: experimental autoimmune encephalomyelitis model group,
EAE + PTx: EAE mice with cerebral ventricle injection of Pertussis toxin (PTx).

Example 14

Results—Table 2

TABLE 2

Histopathological analyses of inflammatory parameters, demyelination and axonal damage in the spinal cord of C57BL/6 mice at 7, 14, and 23 days after MOG$_{35-55}$ EAE induction.

| | EAE | EAE + PTx icv | P value |
|---|---|---|---|
| Inflammation (H and E) | | | |
| day 7 | 0.25 +/− 0.27 | 0.08 +/− 0.20 | 0.260 |
| Day 14 | 3.33 +/− 0.75 | 1.33 +/− 0.75 | 0.001* |
| Day 23 | 3.42 +/− 0.58 | 1.33 +/− 0.68 | <0.001* |
| Demyelination (Fast blue) | | | |
| Day 7 | 0.25 +/− 0.27 | 0.08 +/− 0.20 | 0.260 |
| Day 14 | 3.66 +/− 0.98 | 0.83 +/− 0.98 | 0.001* |
| Day 23 | 3.75 +/− 0.93 | 1.16 +/− 0.98 | 0.001* |

TABLE 2-continued

Histopathological analyses of inflammatory parameters, demyelination and axonal damage in the spinal cord of C57BL/6 mice at 7, 14, and 23 days after MOG$_{35-55}$ EAE induction.

| | EAE | EAE + PTx icv | P value |
|---|---|---|---|
| Axonal loss (silver staining) | | | |
| Day 7 | 0.83 +/− 0.20 | 0.04 +/− 0.10 | 0.664 |
| Day 14 | 2.42 +/− 0.86 | 0.66 +/− 0.51 | 0.002* |
| Day 23 | 2.58 +/− 0.97 | 0.58 +/− 0.49 | 0.001* |

Data presented as Mean +/− SD

Example 15

PTx Icv Prevents Against Dissemination of Motor Deficits in EAE and has a Dose Effect PTx icv (1000 ng) delayed the onset of motor symptoms (11.660.64 versus 8.560.75, p, 0.05) and decreased the severity of motor impairment (maximal clinical score 0.3560.07 vs. 3.2560.37, p,0.01) (FIG. 1). The inventors evaluated whether there was a dose effect associated with administration of PTx icv (200 ng, 400 ng, and 1000 ng). There was a significant dose effect. The 1000 ng group provided a significantly greater therapeutic response than the 400 ng, and the 400 ng greater than the 200 ng (p,0.05) which also provided a significant therapeutic response relative to EAE (p,0.05) (FIG. 1). To control for potential effects of icv administration, EAE mice were treated with same volume of normal saline icv (EAE+NS icv). Motor deficits were unchanged compared to EAE alone (FIG. 1). To determine whether the effects of the spinal cord lesion could be alleviated following symptom onset, PTx icv was administered immediately after the onset of measurable motor deficits (clinical score. 0.5; day 9+ post MOG35-55 inoculation). The delayed administration did not alter the clinical course of EAE (n=6).

Example 16

Figure 2:
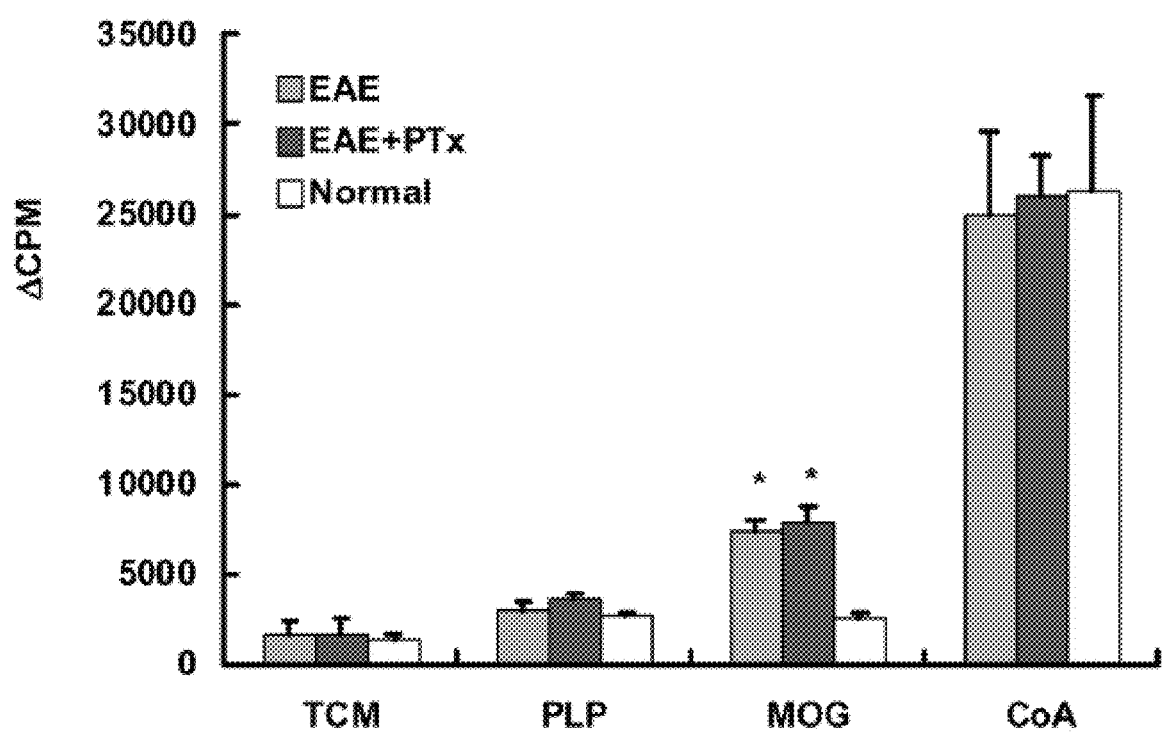
FIG. 2 depicts T cell proliferation responses to the Ag (MOG35-55 peptide) were assessed in triplicate wells for each experiment. It showed a significant difference in PTx+ EAE and EAE versus control (*p,0.01). But there was no difference between PTx+ EAE and EAE mice. Results are expressed as Dcpm (mean cpm stimulated cultures−mean cpm unstimulated cultures). N=6/group.
Figure 3:
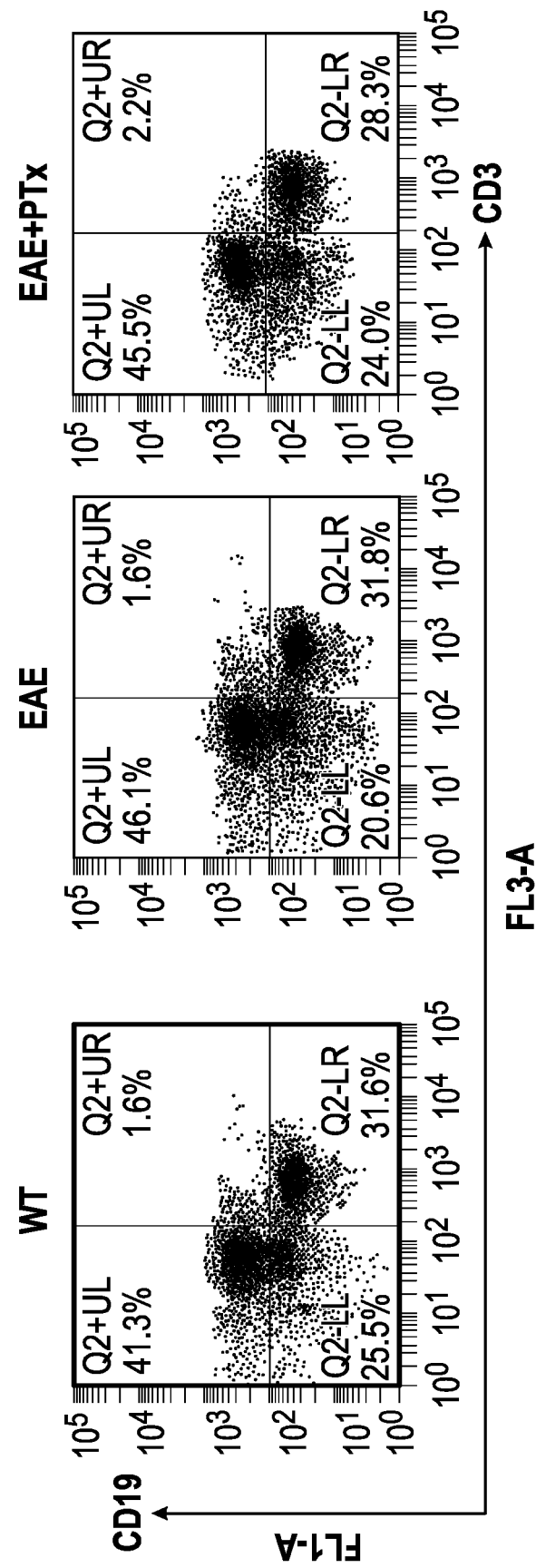
FIG. 3 depicts flow cytometry analysis of mononuclear cells from the spleen on day 14. PTx icv does not alter the peripheral lymphocyte subpopulation in acute EAE. Dot plots of flow cytometry results generated after gating on lymphocytes (by forward and versus side scatter) are shown for T (CD3+, CD4+, CD8+, CD4+/CD25+ and B (CD32/CD19+) cells. WT=wild type group. Absolute numbers of lymphocyte subpopulation, macrophage/microglia cells are shown in the following table. n=6/group. *p<0.05 compared with WT, **p<0.01 compared with WT.
Figure 3:
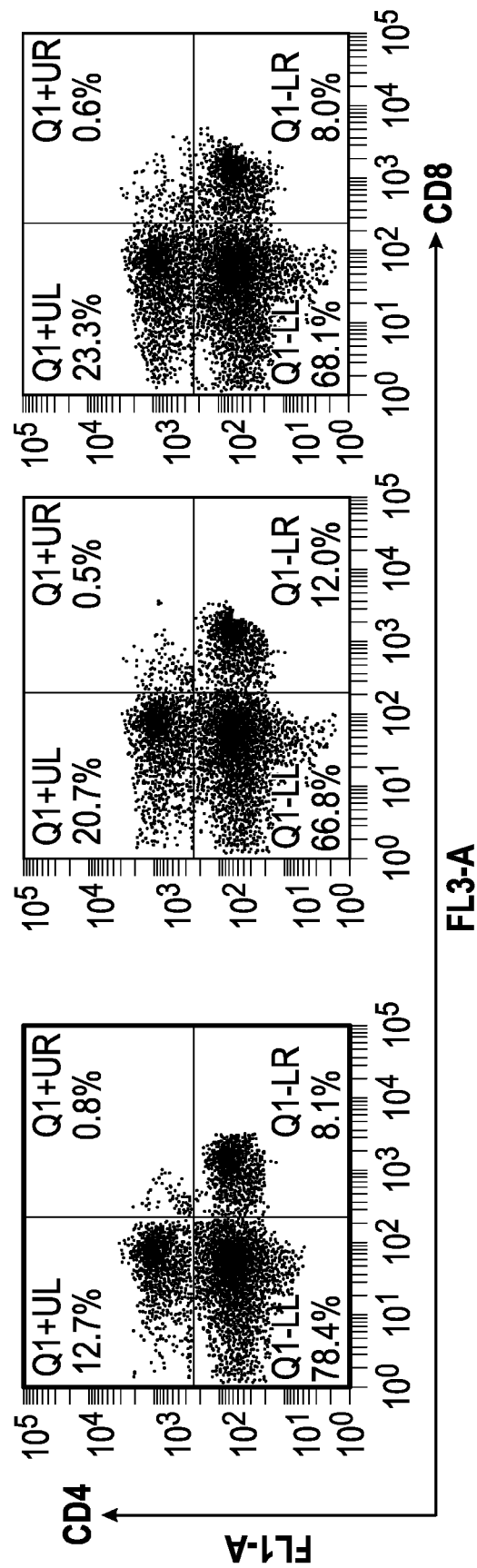
Figure 3:
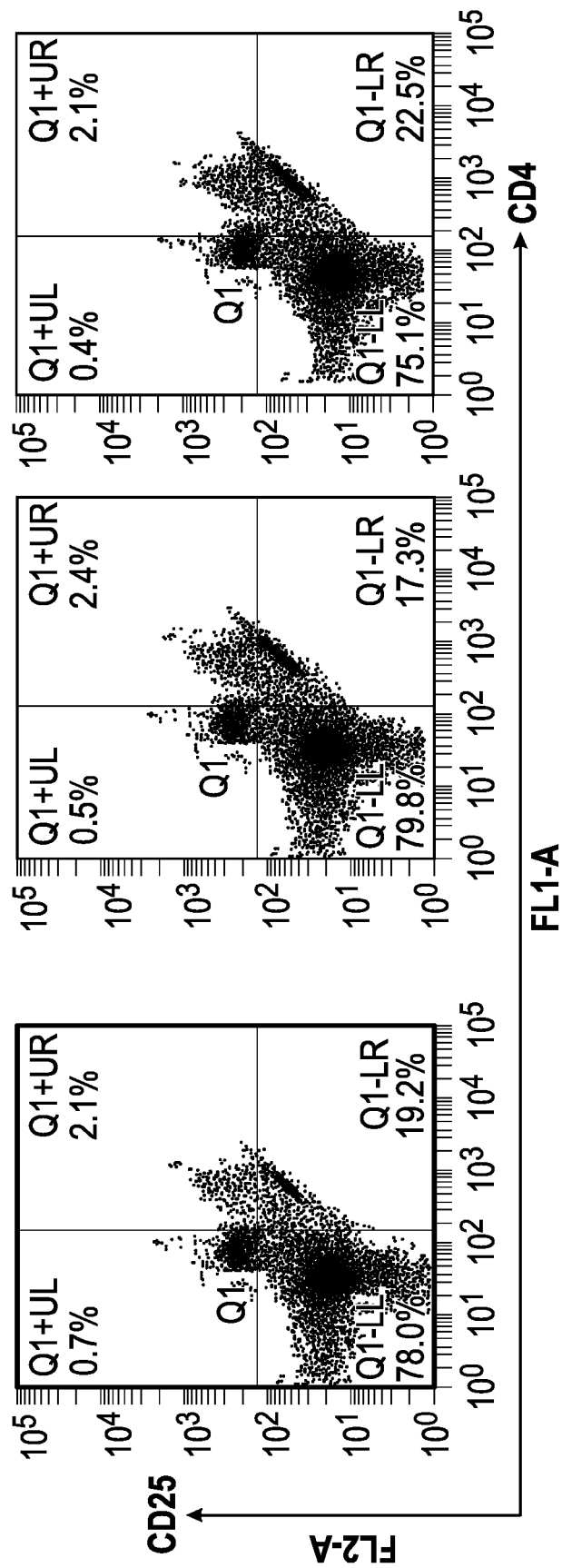

The Variation in Clinical Disease is not Due to Differences in Auto-Reactive T Cell Priming To investigate whether an enhanced expansion of auto-reactive T cells could be responsible for the observed clinical differences in EAE versus EAE+PTX icv, T cells were re-challenged with MOG35-55 in vitro. No differences were observed between EAE and EAE+PTX icv regarding the capacity of T cells to proliferate in response to recall antigen (FIG. 2). Furthermore there was no difference in T cell subpopulations (CD4+, CD8+, CD4+/CD25+), B cell (CD32/CD19+), and macrophage/microglia (CD45+/CD11b+) (FIG. 3). Nor is there a pattern shift in Th1/Th2 between the two groups (Table 1).

Example 17

PTx Icv Attenuates Spinal Cord Leukocyte Infiltration and Demyelination in EAE

Figure 4:
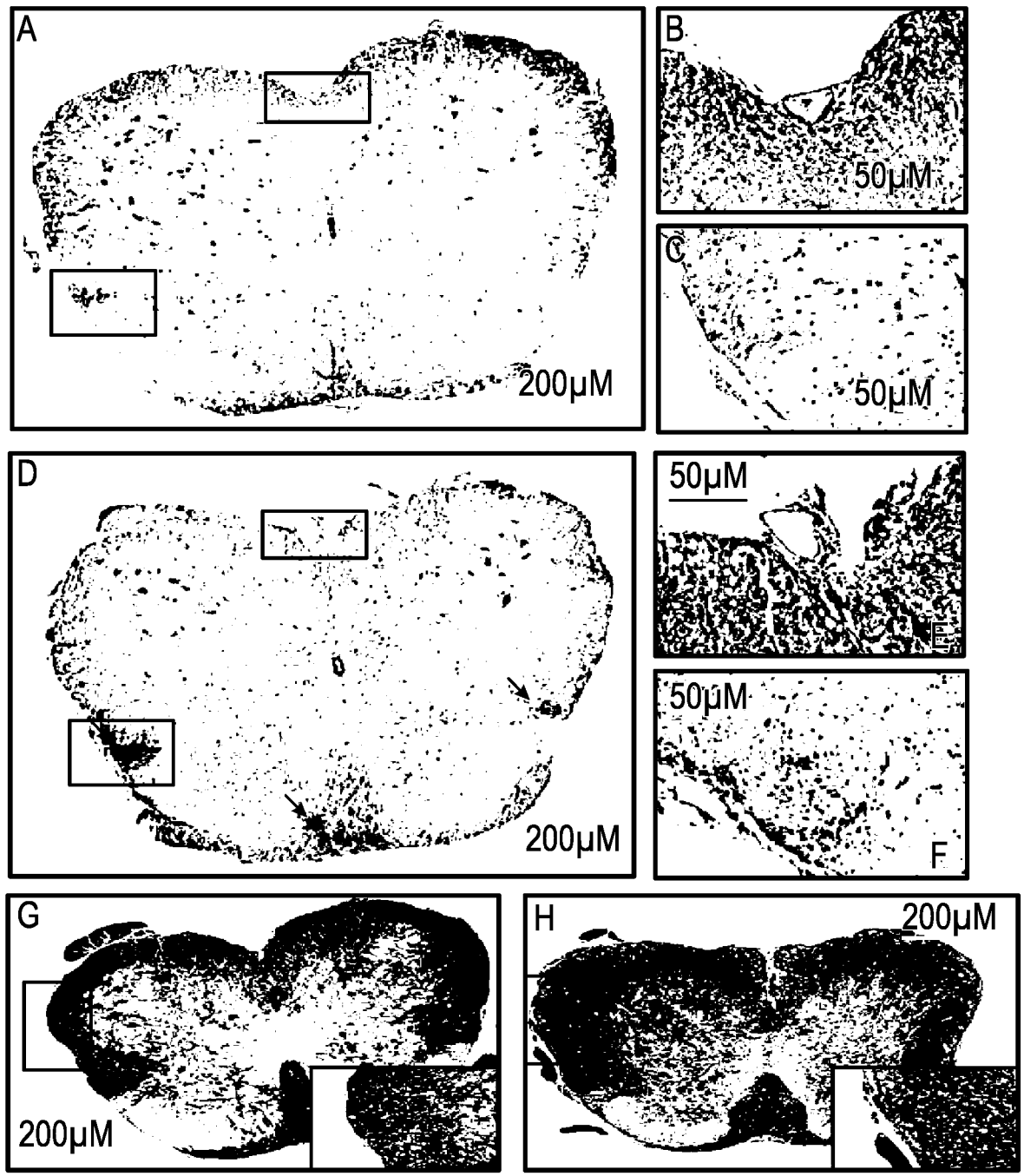
FIG. 4 depicts attenuation of the progression of inflammation and tissue injury in the CNS of mice that received PTx icv. Pathological examination of spinal cord sections from EAE+PTx icv and EAE mice were performed at 7, 14, and 23 days post EAE induction to evaluate CNS inflammation, demyelination and axonal damage. In EAE+PTx icv mice, the number of immune-cell infiltrates (H&E staining, FIG. 4A-C) and demyelination (Luxol fast blue staining, FIG. 4G) were both significantly reduced at day 14 and 23 post EAE induction. Representative day 14 images of H&E staining (A-F) and LFB/PAS staining (G, H). B and C were inserts in A; E and F were inserts in D. Original magnification 640 in A, D, G and H; 6200 in B, C, E, F, and inserts in G and H.

On day 14 and 23, H&E staining in the cross-sectional of the spinal cord of EAE mice showed widespread infiltration of inflammatory cells in the spinal cord (FIG. 4D-F). In contrast, EAE+PTx icv mice exhibited markedly decreased infiltration of inflammatory cells in the spinal cord on day 14 and 23. (FIG. 4A-C, Table 2). To determine the degree of demyelination, we stained sections of spinal cord with Luxol fast blue and observed widespread demyelination zones in the white matter of the spinal cord of EAE mice on day 14 and 23 (FIG. 4H). In contrast, on day 14 and 23, mice that received PTx icv had minimal evidence of demyelination indicated by a markedly attenuated course of disease (FIG. 4G, Table 2). Marked axonal loss characterizes the MOG35-55 model of EAE, and this is evident in the spinal sections of the EAE mice assessed with Bielschowsky silver impregnation. Attenuation of axonal injury is evidenced in EAE+PTx icv mice (Table 2).

Example 18

PTx Icv Increases BBB Permeability in EAE

Figure 5:
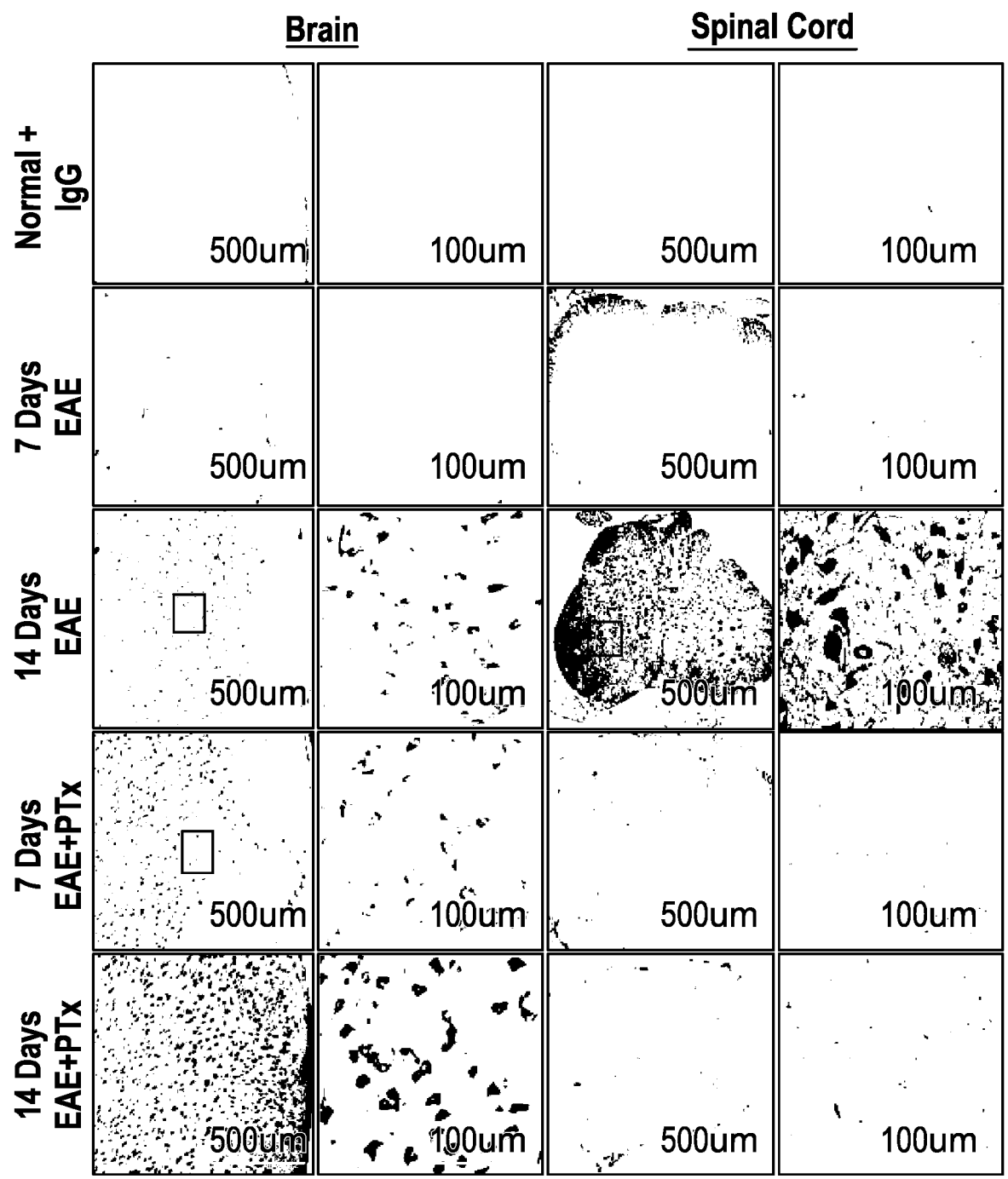
FIG. 5 depicts rabbit immunoglobulin G (IgG) penetration into the frontal lobe parenchyma and thoracolumbar spinal cord in control, EAE, and EAE+PTx icv (n=7/group). Normal +IgG: age-controlled normal mice without EAE receiving a single i.p. injection of rabbit IgG (100 mg/mouse). 7 days EAE: EAE mice on day 7 post immunization; no penetration of rabbit IgG observed in the brain or spinal cord. 14 days EAE: EAE mice on day 14; marked penetration of rabbit IgG noted in both brain and spinal cord. 7 days EAE+PTx: EAE+PTx icv mice on day 7 post immunization; marked penetration of the brain, but no penetration of the spinal cord. 14 days EAE+PTx: EAE+PTx icv mice on day 14 post immunization, continued evidence of brain penetration, no penetration of the spinal cord. Note the dramatic opening of the BBB on Days 7 in EAE+PTx icv group relative to EAE on day 7.
Figure 6:
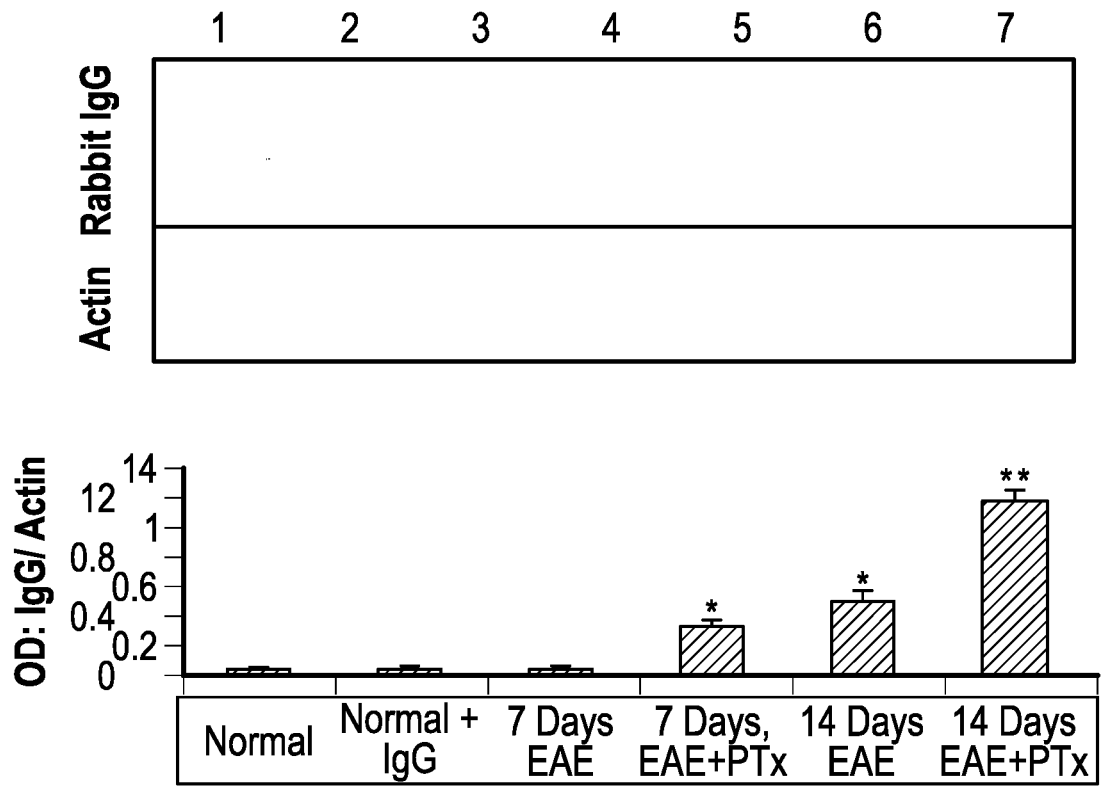
FIG. 6 depicts western blot depicts measures of rabbit IgG. Lane 1: purified rabbit Ig G as the positive control; lane 2-7 correlates the plotted graph below. Statistical evaluation of optic density (OD) normalized to b-actin was obtained for each group. Mean 6 SD are depicted (n=7 per group). *P<0.01, compared with normal control; **P<0.01, compared with normal control group and EAE.
Figure 6:
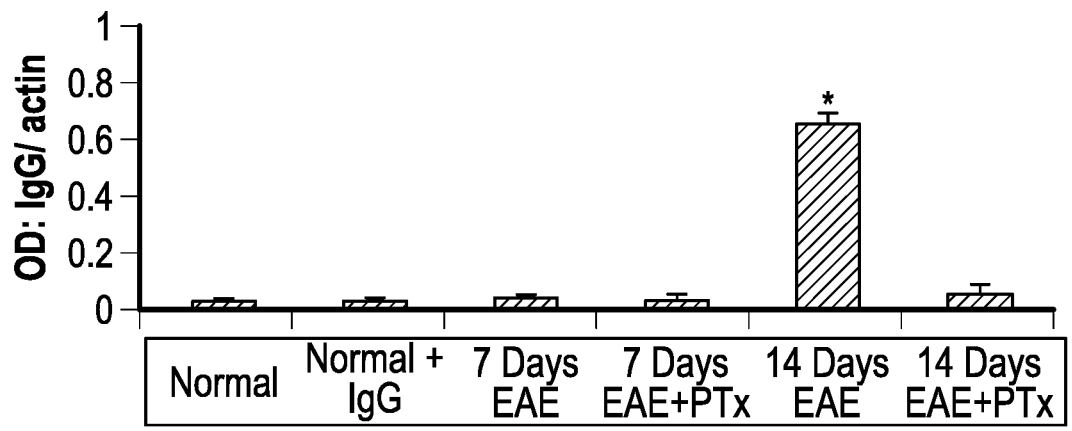

The inventors determined BBB integrity by localizing rabbit IgG in the CNS in EAE and EAE+PTx icv before (day 7) and during the peak (day 14) of symptomatic disease. On day 7, rabbit IgG immunoreactivity was observed in the brains of EAE+PTx icv but not in EAE mice (FIG. 5, 6). In the spinal cord no immunoreactivity was observed in either group. On day 14, EAE mice demonstrated immunoreactivity diffusely throughout the parenchyma of the spinal cord with minimal evidence of reactivity in the brain. EAE+PTx icv mice showed rabbit IgG immunoreactivity in the brain, but not in the spinal cord (FIG. 5, 6). To control for potential effects of PTx on BBB integrity, separate from its exacerbation of EAE related inflammation, mice were treated with 1000 ng PTx icv but were not exposed to MOG35-55. In contrast to EAE+PTx icv mice (FIG. 5, 6), mice that received only PTx icv exhibited no accumulation of rabbit IgG in the brain or the spinal cord. Thus, the BBB breakdown described above was caused by the effect of PTx icv in the context of EAE.

Example 19

Figure 7:
FIG. 7 depicts inflammatory cytokines and cells in the spinal cord of EAE and EAE+PTx icv mice (n=6/group). IL-17+/CD4+ cells were detected in the meninges of the spinal cord in the EAE+PTx icv mice (A-C), whereas these cells were diffusely identified in the spinal parenchyma in the EAE mice (D-F). Original magnification 6400. The western blot depicts measures of IL-17 (G), IL-6 (H) and TGF-b (I). In the spinal cord, elevated levels of all three were identified in the EAE mice relative to the EAE+PTx icv mice. Statistical evaluation of optic density (OD) normalized to b-actin was obtained. Mean 6 SD are depicted (n=6 per group). *P<0.05, compared with normal control group; #P<0.05, compared with EAE group.
Figure 7:
Figure 7:
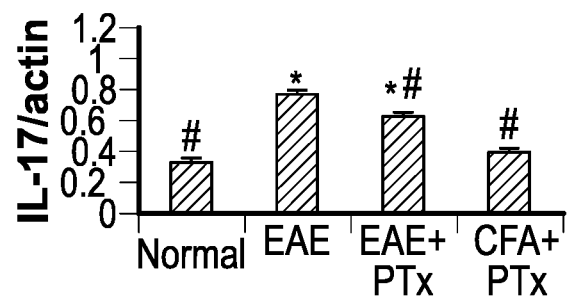
Figure 7:
Figure 7:
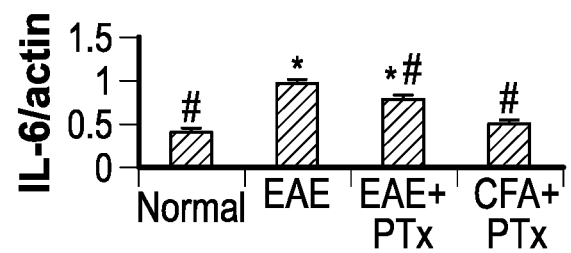
Figure 7:
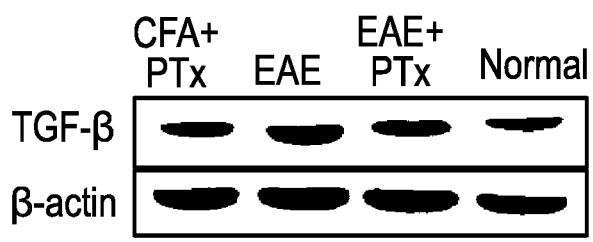
Figure 7:
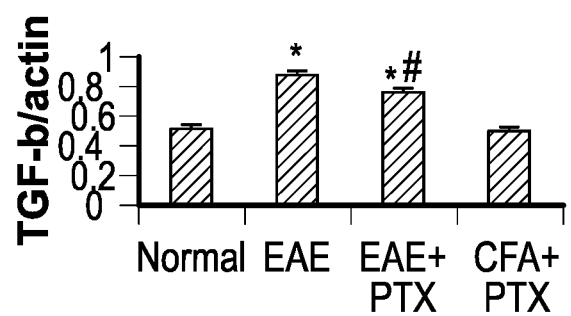

PTx Icv Preferentially Induces the Development of Myelin-Reactive Th-17 Cells in the Brain T helper cell lineage development depends on local cytokine milieus and specific immune factors. Emerging evidence supports the pathonogmonic role of Th-17 cells in EAE and the role of PTx in the induction of Th-17 [28]. For the Th-17 cells, TGF-b and IL-6 drive the initial lineage commitment. The inventors quantified the Th-17 cell concentration in our model after PTx icv was administered. In the spinal cord, the presence of IL-17 CD4 cells was rare and limited to the meninges in the EAE+PTx icv mice (FIG. 7A-C), whereas a considerable number of Th-17 cells were identified in the spinal parenchyma of the EAE mice (FIG. 7D-F). The protein levels of IL-17, IL6 and TGF-b (FIG. 7G-I) were significantly elevated in the spinal cord of the EAE relative to the EAE+PTx icv mice (p,0.05), correlating the spinal cord pathology in EAE mice.

Figure 8:
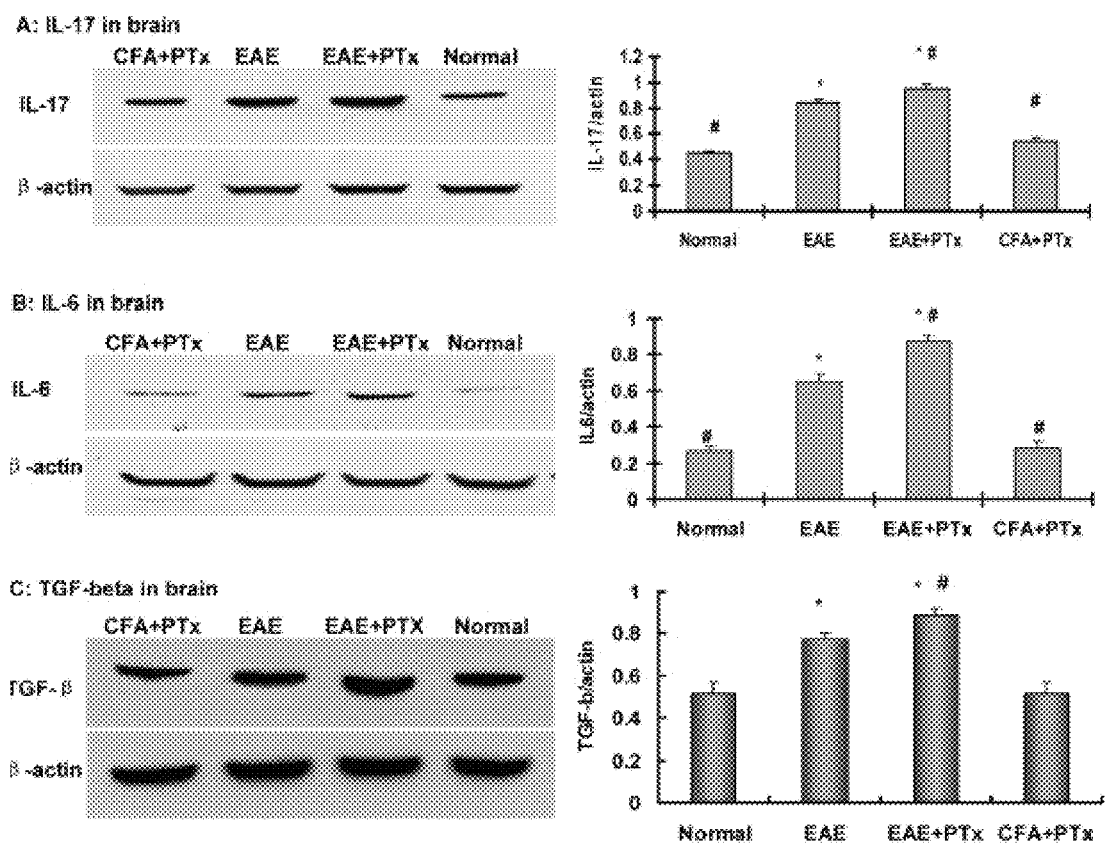
FIG. 8 depicts western blot measures of IL17 (A), IL6 (B) and TGF-b (C) in the brain of EAE+PTx icv compared with in EAE alone mice as well as controls. Statistical evaluation of optic density (OD) normalized to b-actin was obtained. Mean+/2 SD are depicted (n=6 per group). *P<0.05, compared with normal control group; #P<0.05, compared with EAE group.

In the brain, the EAE+ PTX icv mice exhibited infiltrating leucocytes which stained positive for CD 4 and IL-17. The majority of these colocalized cells were in the periventricular white matter, confirming the infiltration of proinflammatory Th-17 cells induced by PTx icv. Whereas, in the EAE alone mice, the presence of Th-17 cells in the brain was limited to the meninges. The protein level of IL-17, IL-6, and TGF-b were significantly elevated in the brain of EAE+PTx icv mice, relative to the controls and the EAE alone mice (FIG. 8) (p,0.05). In normal control and CFA+ PTx icv groups, no IL-17+ cells were detected in brain.

Example 20

Figure 9:
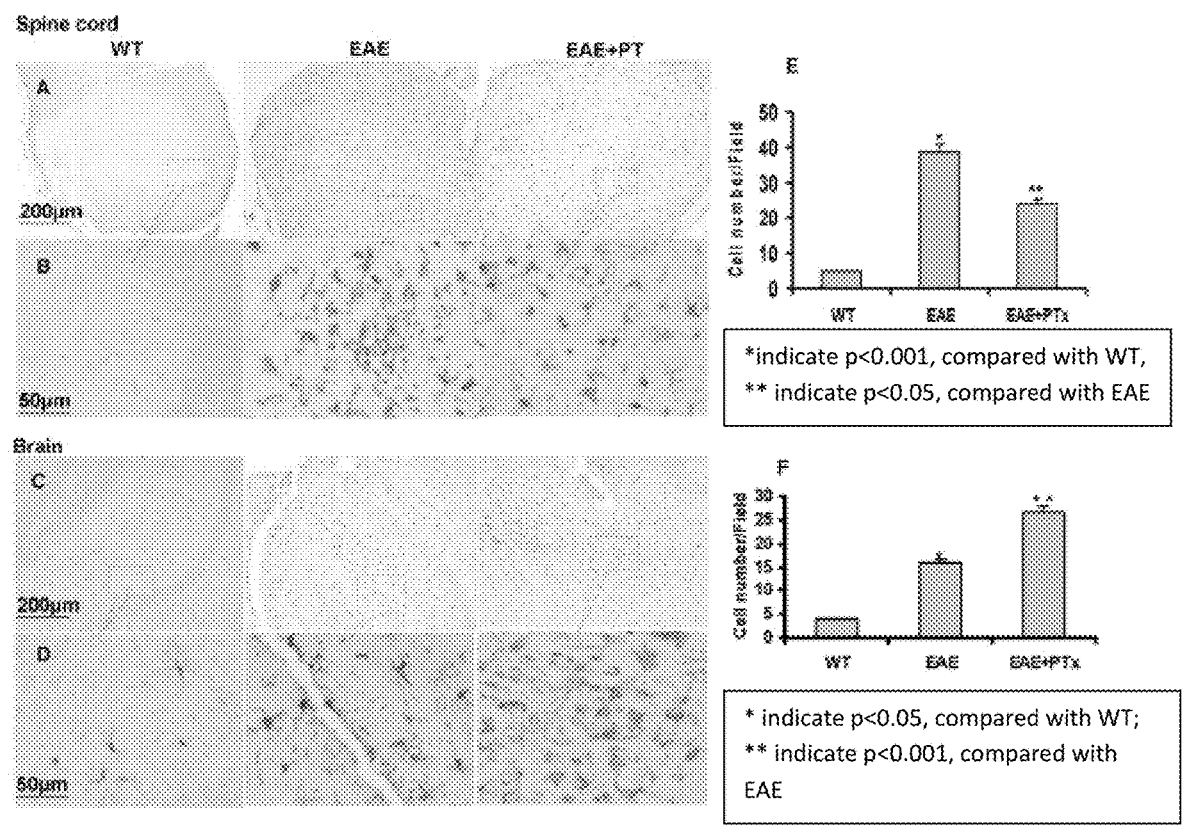
FIG. 9 depicts anti-Iba1 immunostaining of spinal cord and brain of WT, EAE and EAE+PTx icv mice. Brain and spinal cord sections were immuno-stained at 7 days post MOG immunization with the anti-Iba1 antibody. A: Low-magnification image of spinal cord section (Scale bar=200 mm). The anti-Iba1 antibody reacted strongly with amoeboid-shaped cells, corresponding to activated microglia in the spinal cord of EAE mice. This was significantly less prominent in the EAE+PTx icv mice. In WT controls, the antibody also effectively, but rather weakly, recognized ramified or resting microglia; these cells have small bodies and finely branched processes. B: High-magnification image of the spinal cord sections (Scale bar=50 mm). C: Low-magnification image of cerebral cortex (Scale bar=200 mm). The anti-Iba1 antibody reacted strongly with amoeboid shaped cells, corresponding to activated microglia in the brain of EAE+PTx icv mice. WT controls manifest ramified or resting microglia; whereas EAE mice manifest an intermediate stage. D: High-magnification image of the brain sections (Scale bar=50 mm). E-F. Microglia were quantified and compared among the groups by counting the number of cells in the field. Five random fields at 40× fields were counted for each condition under a digital axoplan microscope. Results were shown as the cells counted per 40× field. *p<0.05 compared with wt; **p<0.01, Compared with EAE.
Figure 10:
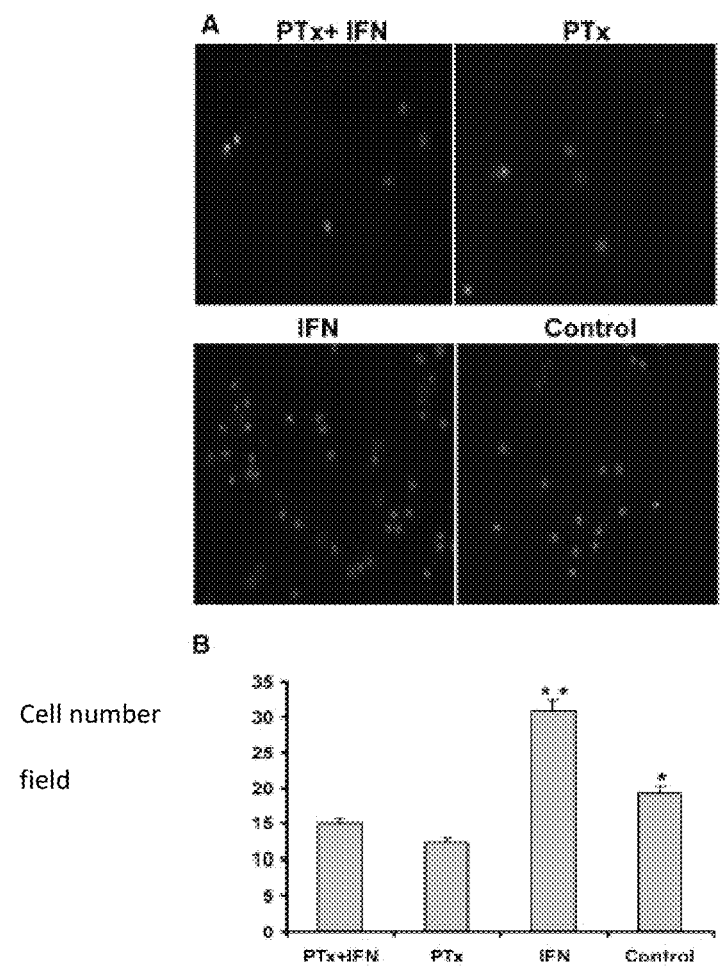
FIG. 10 depicts PTx significantly reduced migration of stimulated microglia. Microglia migration was quantified and compared among the groups by counting the number of cells that migrated through the membrane to the lower chamber. Five random fields at 40× fields were counted for each condition under a phase contrast microscope. Results were shown as the cells counted per 40× field (A and B). In PTx treated groups, cell migration was significantly reduced. *p<0.05 compared with PTx; **p<0.01, Compared with PTx+ IFN, PTx and Control groups.

PTx Icv Retains Macrophage/Microglia and to a Lesser Degree T Cell Infiltration to the Brain Preventing Dissemination to the Spinal Cord The most salient finding of PTx icv on day 7 post immunization was the parenchymal infiltration of macrophage/microphage (Iba1), and to a lesser magnitude T cell (CD4), in the brain (FIG. 9). In the brain of EAE+PTx icv mice, anti-Iba1 antibody reacted strongly with amoeboid-shaped cells, corresponding to activated microglia on day 7. Wild type controls manifest ramified or resting microglia; whereas EAE mice manifest intermediate responsiveness and ramification (FIG. 9-C, D, F). In contrast, the spinal cord of EAE mice showed amoeboid-shaped cells that stained strongly with anti-Iba1 antibody, corresponding to activated microglia (FIG. 9-A, B, E). To further determine the effect of PTx on microglia migration, the inventors utilized the Transwell to assess in vitro migration. PTx significantly inhibited the migration of microglia with and without IFN-c stimulation (FIG. 10).

Example 21

Therapeutic Effect of PTx

PTx results in evidence of: 1) dose and time course dependent attenuation of motor clinical symptoms; 2) In the spinal cord, typically the most affected region in the traditional EAE model, evidence of minimal T cell infiltration, and the marked absence of axonal loss and demyelination; 3) abrogation of the migration of microglia as well as T cells to the lesion target and 4) modulation blood brain barrier (BBB) integrity. These results indicate that PTx icv/ip results in a therapeutic response in the EAE model.

The data demonstrates that neurodegenerative changes in the spinal cord are directly impacted by the therapeutic effects of PTx. PTx is recognized as an immunoadjuvent and has been used to increase disease severity; however, in this case it has a therapeutic effect, demonstrating the therapeutic effect of PTx given in a single dose on EAE. Successful demonstration of the mechanism of its dichotomous effect also provide a clearer understanding of its role in autoimmune diseases. Secondly, the inventors demonstrate the concept of a therapeutic lesion. Though the concept of a therapeutic lesion, with actual placement of a lesion in humans, has been seen in the neurodegenerative disorder, such as Parkinson's, disease, in that situation the mechanism is thought to be neurotransmitter driven. Data described herein has shown that PTx administered through the ventricle as well as ip results in a therapeutic brain lesion which is mediated immunologically i.e. increased adhesion molecule activity and local infiltration but decreased migrational activity in EAE, and the results support this.

PTx icv:
1. PTx icv prevents against dissemination of motor deficits in EAE and has a dose effect,
2. The variation in clinical disease is not due to differences in auto-reactive T cell priming.
3. PTx icv attenuates spinal cord leukocyte infiltration and demyelination in EAE
4. PTx icv increases BBB permeability in EAE
5. PTx icv preferentially induces the development of myelin-reactive Th-17 cells in the brain.
6. PTx icv retains macrophage/microglia and to a lesser degree T cell infiltration to the brain preventing dissemination to the spinal cord.

Figure 11:
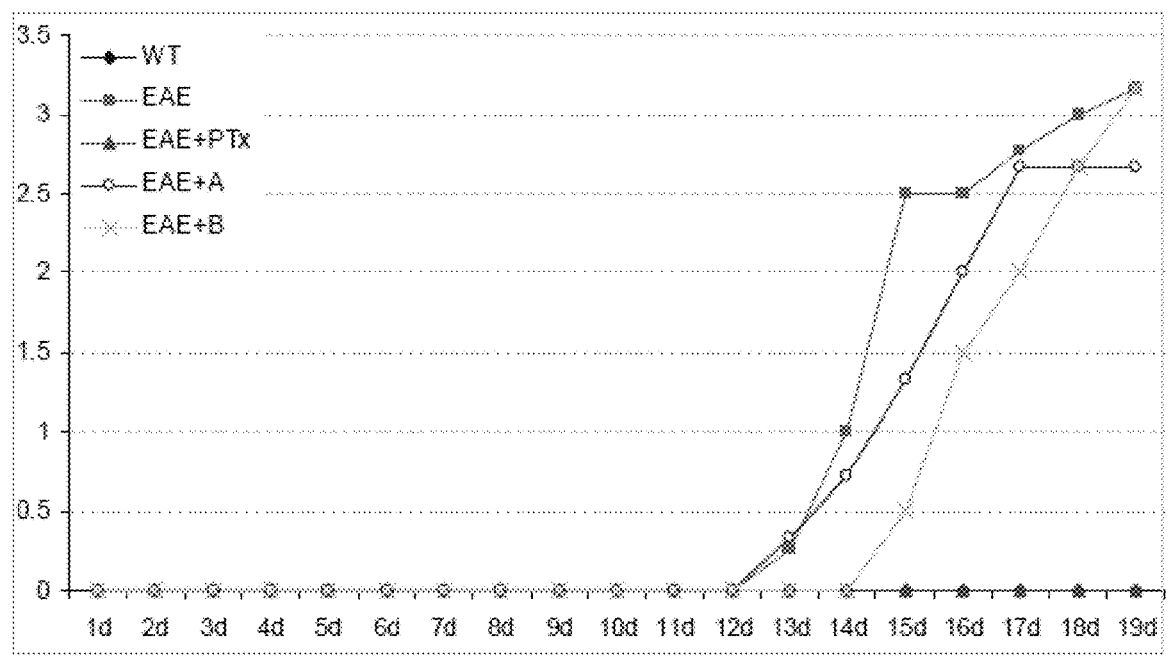
FIG. 11 depicts PTx ip (1000 ng) delayed the onset of motor symptoms and decreased the severity of motor impairment (p<0.01) (FIG. 11). The inventors evaluated whether A or B subunit alone was effective with equivalent dosage. Neither of them showed therapeutic effect. B subunit alone showed a trend in delaying the onset of motor deficits.
Figure 12:
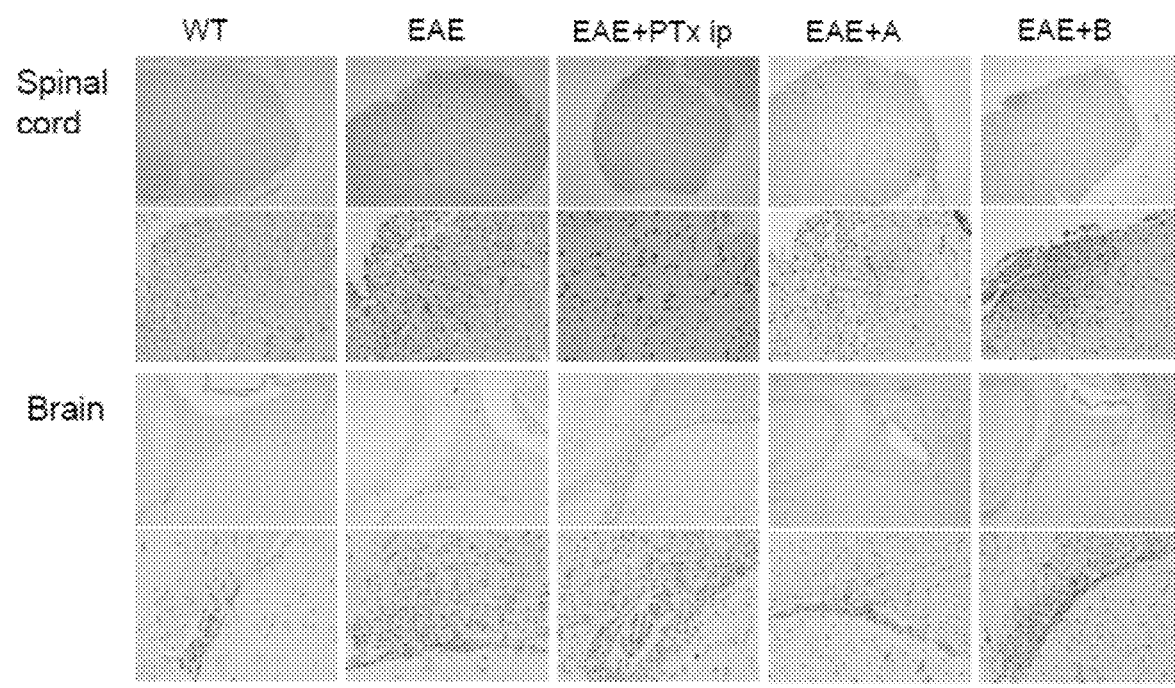
FIG. 12 depicts EAE+PTx ip mice exhibited markedly decreased infiltration of inflammatory cells in the spinal cord.
Figure 13:
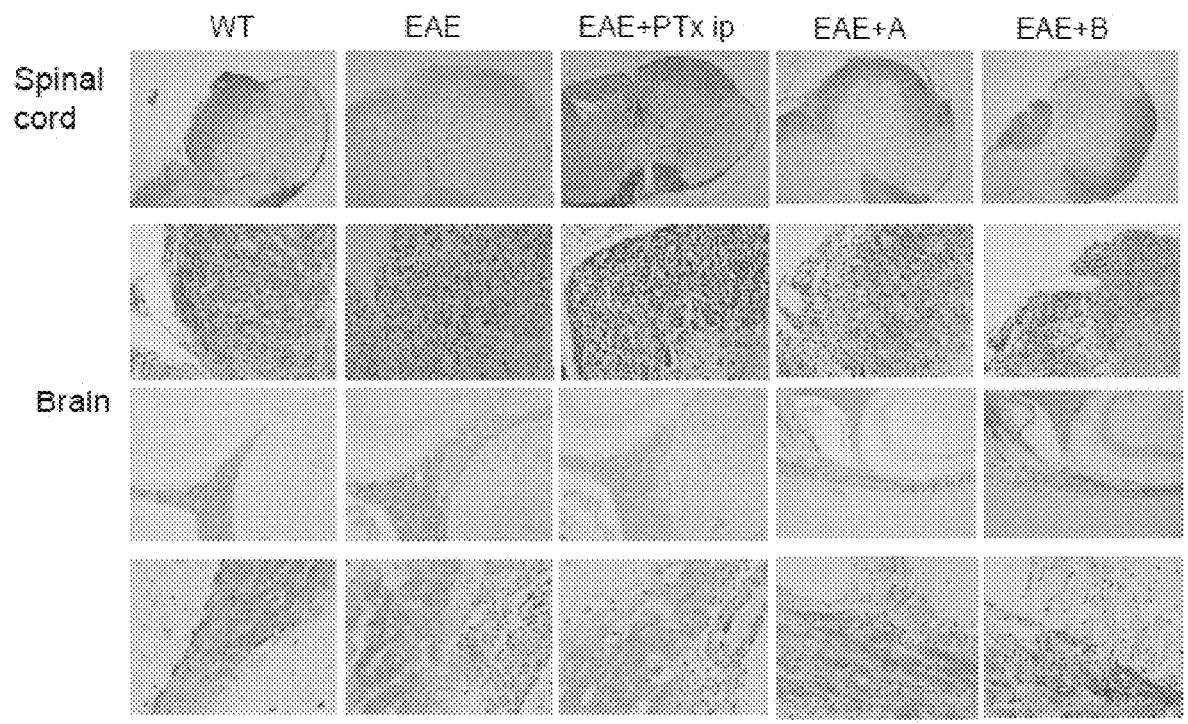
FIG. 13 depicts luxol fast blue staining which observed widespread demyelination zones in the white matter of the spinal cord of EAE mice compared to EAE+PTx ip mice.
Figure 14:
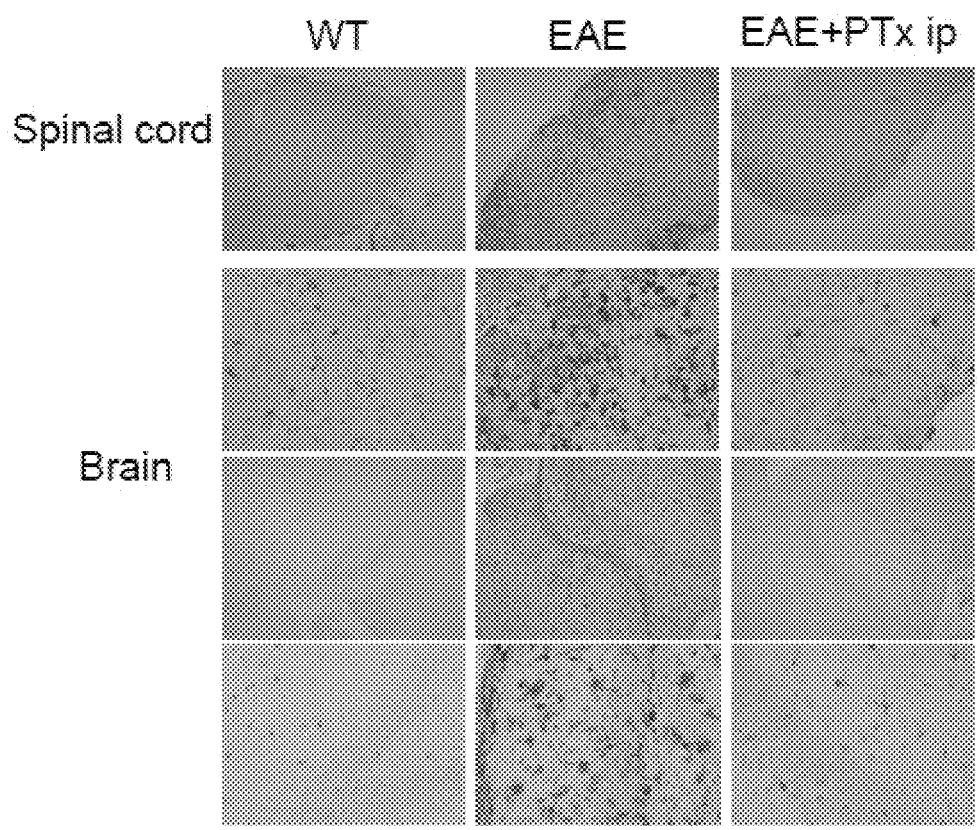
FIG. 14 depicts PTx ip attenuates macrophage/microglia infiltration to the CNS. In the brain and spinal cord of EAE mice, anti-Iba1 antibody reacted strongly with amoeboid-shaped cells, corresponding to activated microglia. Wild type controls manifest ramified or resting microglia; whereas EAE+PTx ip mice manifest intermediate responsiveness and ramification.
Figure 15:
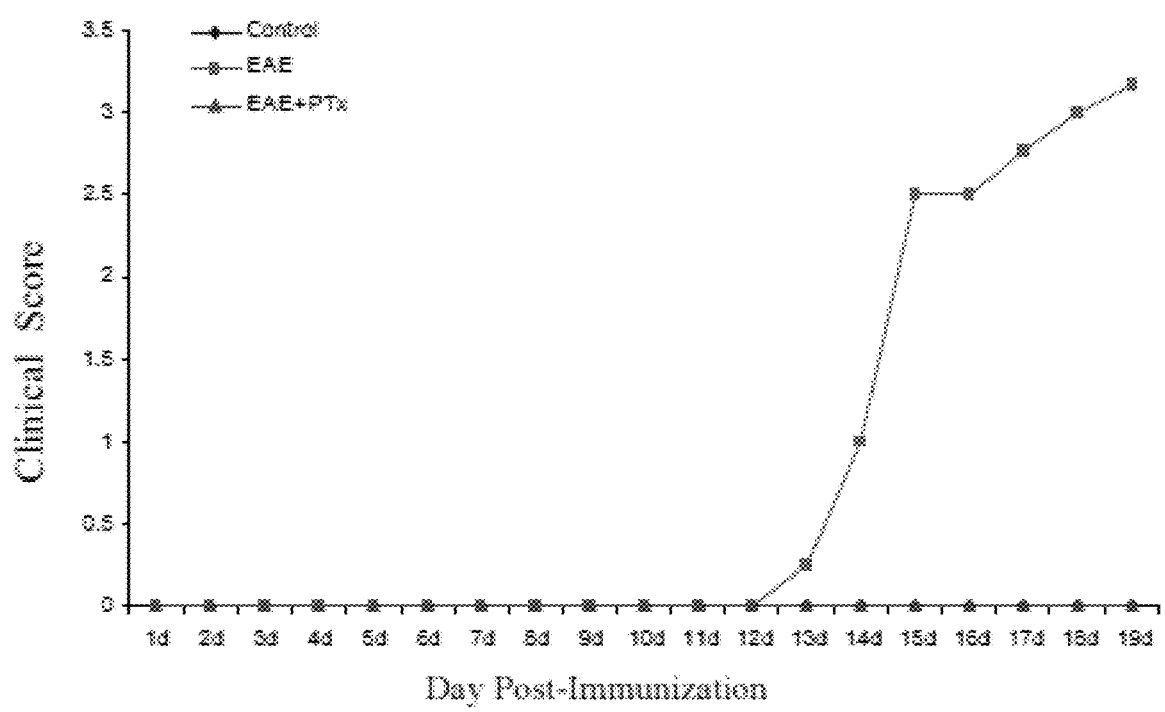
FIG. 15 depicts PTx attenuated clinical deficits of EAE. Clinical scores were plotted as the mean±SD (n=12/group). Clinical signs began on day 13 post-immunization and continued to worsen on day 19 in the EAE group. In PTx treatment group, no clinical sign was observed.
Figure 16:
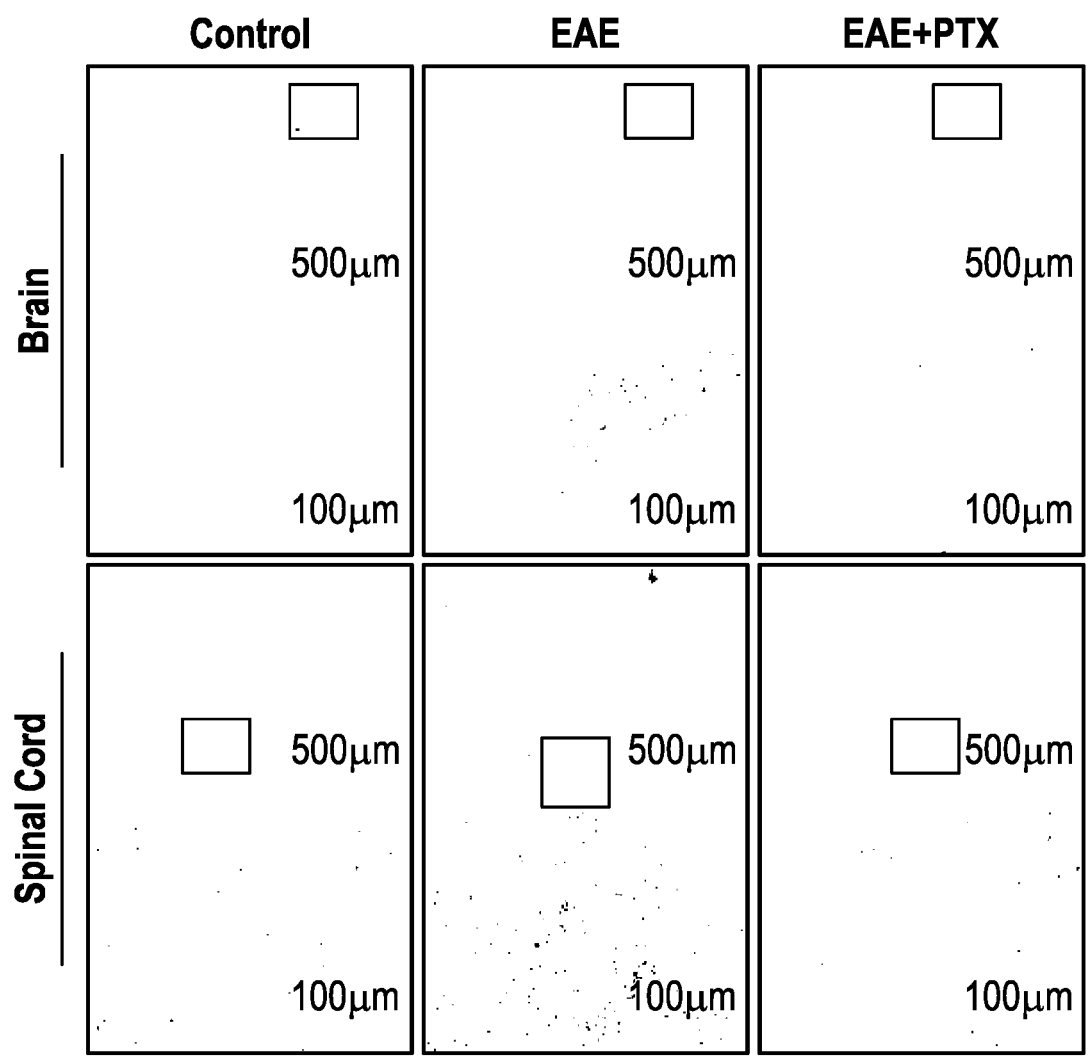
FIG. 16 depicts PTx attenuated inflammation in EAE. Pathological examination of brain and spinal cord sections were performed at day 19 post EAE induction to evaluate CNS inflammation. Abundant infiltrating inflammatory cells around blood vessels and in the parenchyma of brain and spinal cord were shown in the EAE group. They were significantly reduced in the PTx treatment group. Representative images of H&E staining were shown. Original magnification ×40; inserts ×200.
Figure 17:
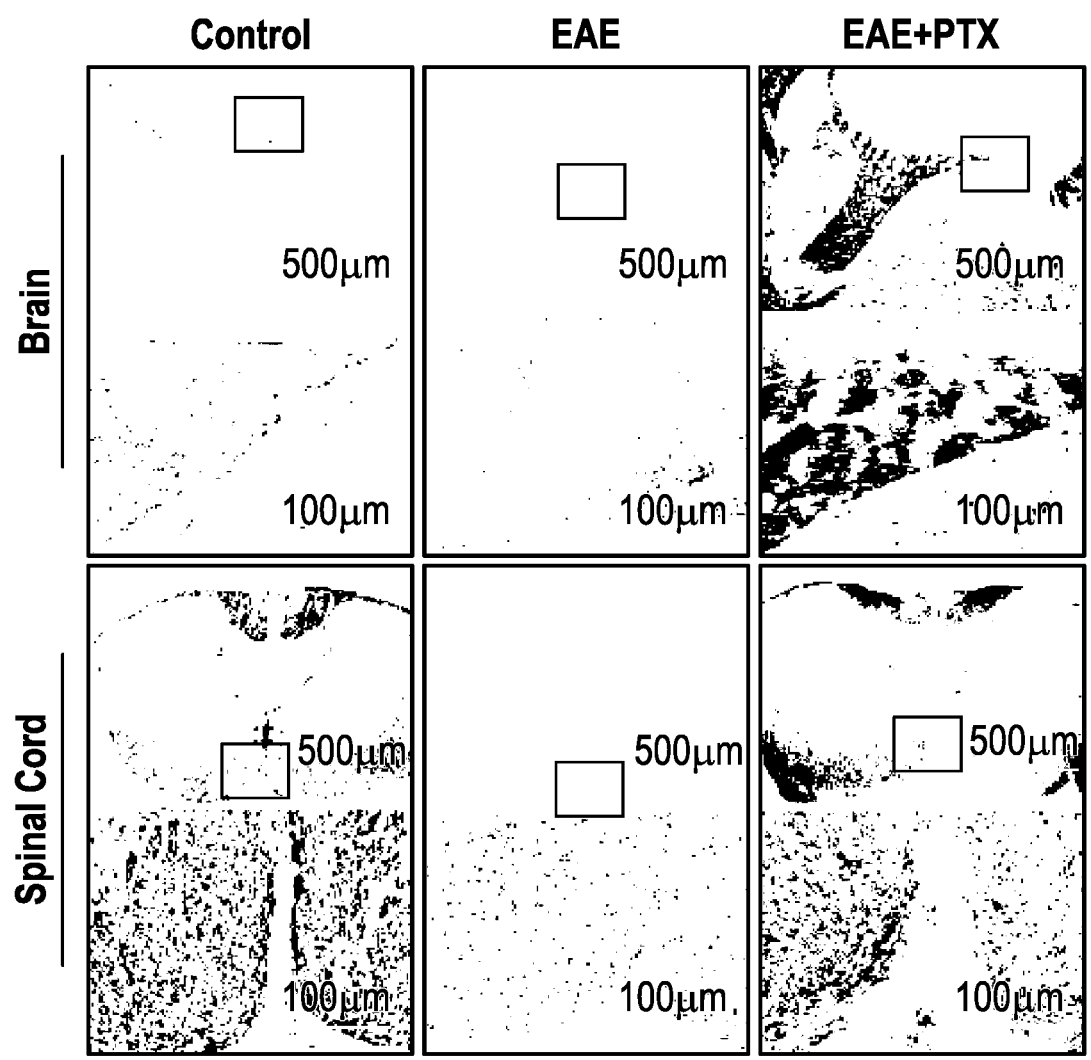
FIG. 17 depicts PTx attenuated demyelination in EAE. Pathological examination of brain and spinal cord sections were performed at day 19 post EAE induction to evaluate CNS demyelination. Massive subpial demyelination with inflammatory cells infiltrating in parenchyma were seen in both brain and spinal cord in EAE, especially in the spinal cord. They were significantly reduced in the PTx treatment group. Representative images of Luxol fast blue staining/ PAS staining were shown. Original magnification ×40; inserts ×200.
Figure 18:
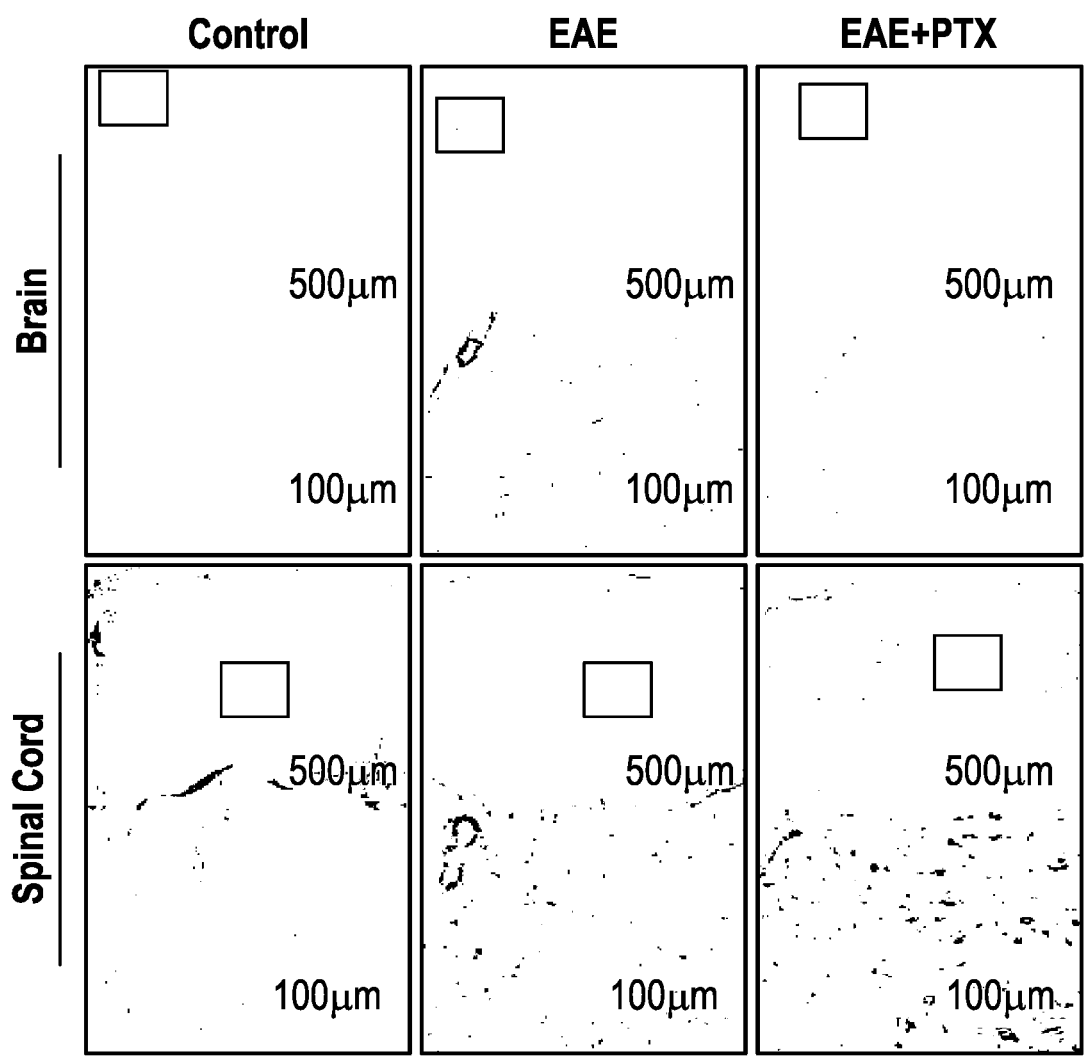
FIG. 18 depicts PTx increased VEGF expression. Immunohistochemistry of brain and spinal cord sections were performed at day 19 post EAE induction. The expression of VEGF was increased significantly by PTx treatment. The morphology of these cells is suggestive of neurons. Representative images of immunostaining were shown. Original magnification ×40; inserts ×200.
Figure 19:
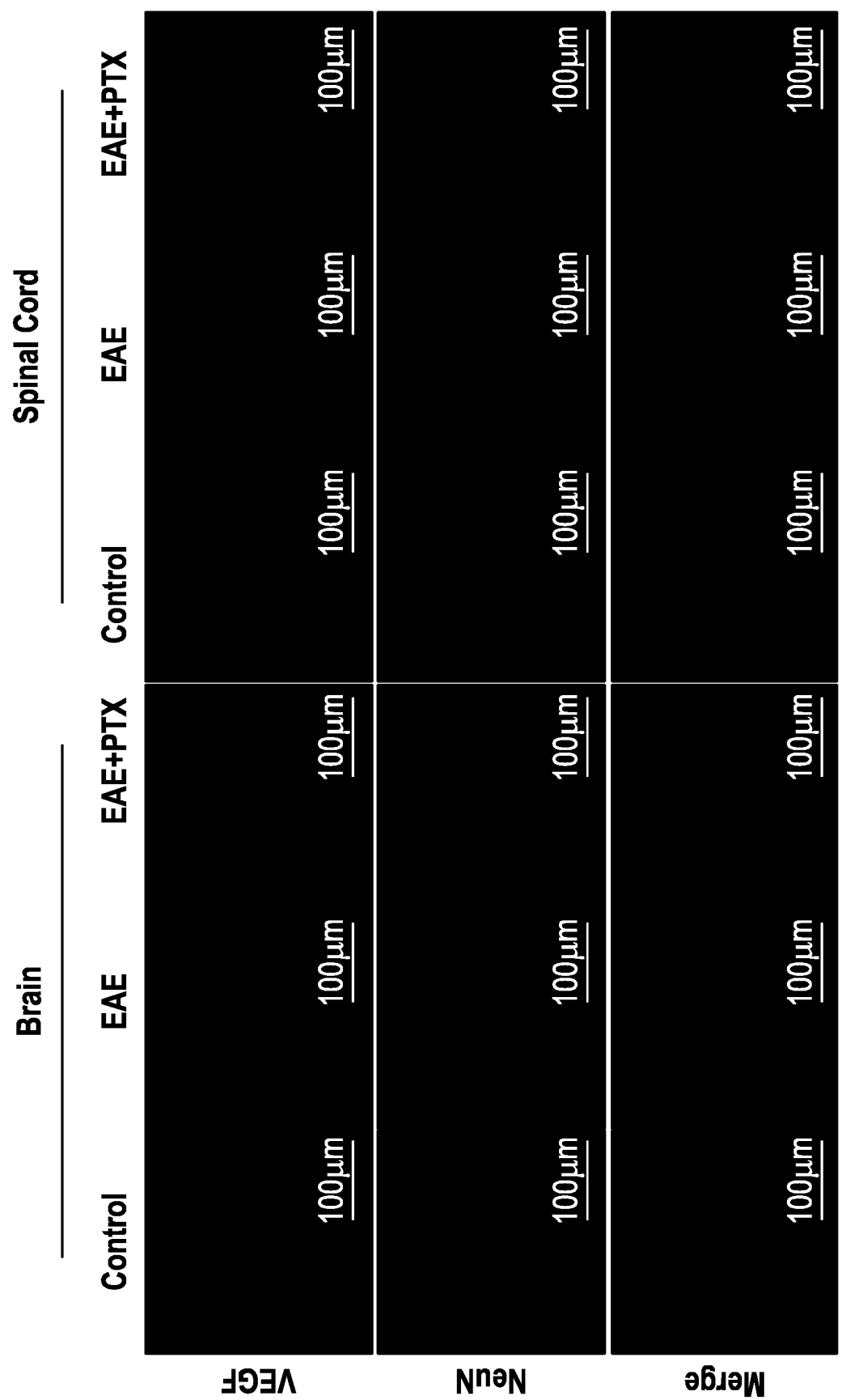
FIG. 19 depicts PTx increased VEGF expression on neurons. Double staining of brain and spinal cord sections with VEGF and NeuN antibodies confirmed VEGF expression on neurons. PTx significantly increased the expression of VEGF on neurons. Original magnification ×200.
Figure 20:
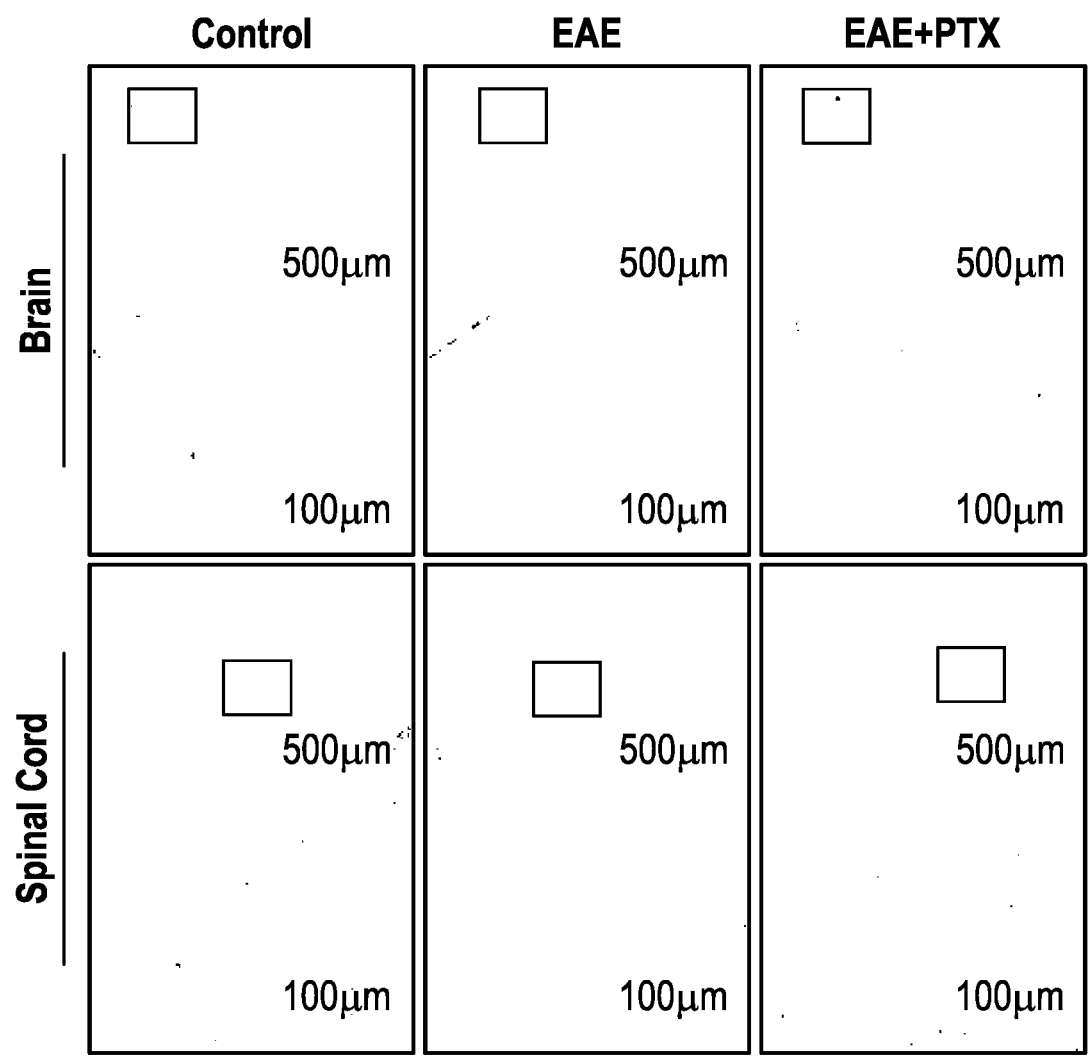
FIG. 20 depicts PTx increased angiogenesis. Brain and spinal cord sections were stained by Collagen IV to count the vessels. PTx treatment increased the vessel counts significantly versus EAE and control. Original magnification ×40; inserts ×200.
Figure 21:
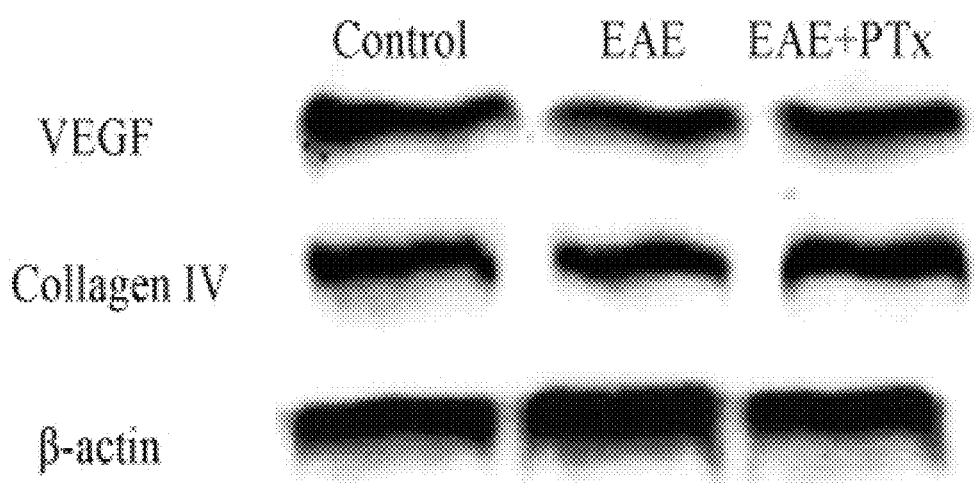
FIG. 21 depicts PTx increased protein levels of VEGF and Collagen IV in the brain. Shown is the representative western blot depicting VEGF and Collagen IV from brain homogenate. Statistical evaluation of optic density (OD) normalized to (3-actin was obtained. Both VEGF and collagen type IV were decreased in EAE (*P<0.05) and increased in the PTx treatment group (**p<0.01).
Figure 22:
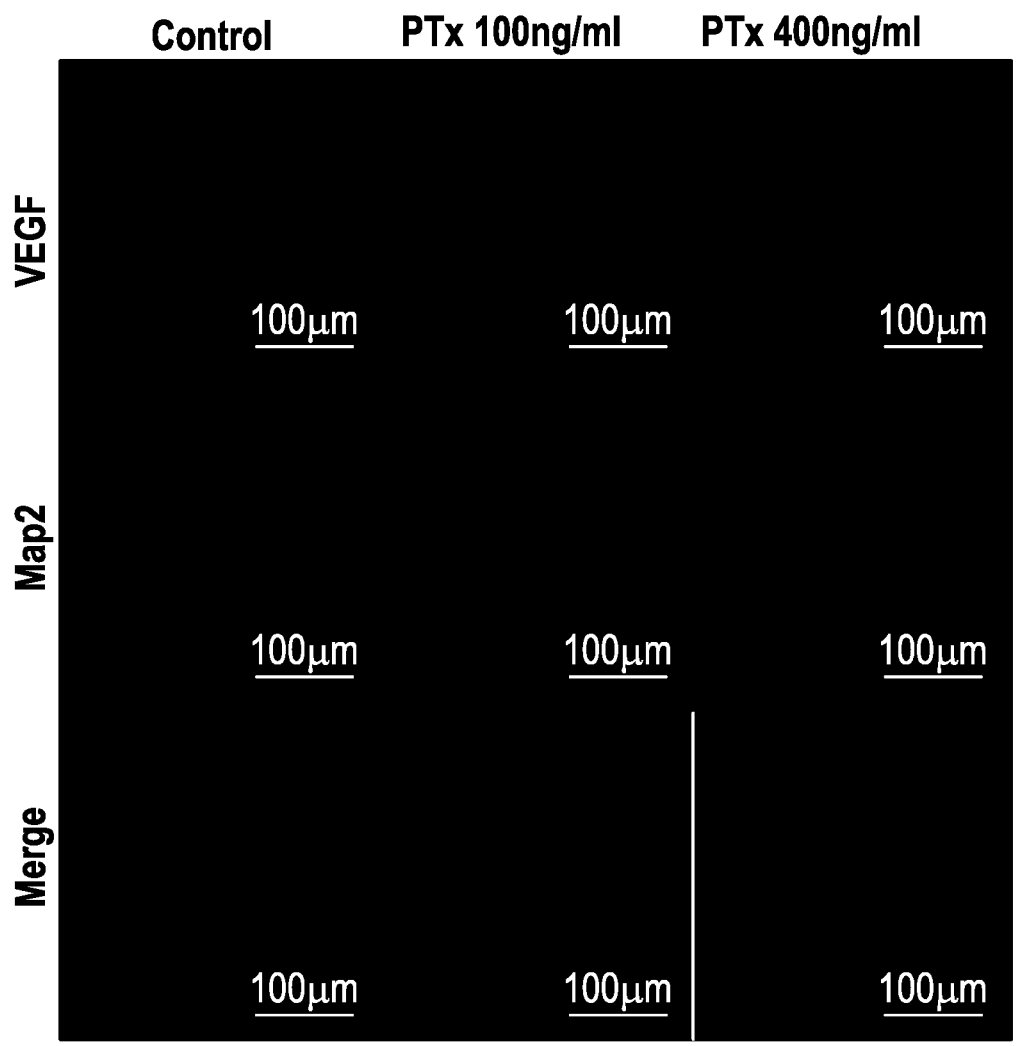
FIG. 22 depicts PTx increased the expression of VEGF. Primary neurons were cultured for 7 days and treated with PTx at the concentration of 100 and 400 ng/ml for one day. Double staining with VEGF and Map2 antibodies showed the expression of VEGF on PTx treated primary neurons. The VEGF was increased in a dose-dependent patent (*P<0.01). Original magnification ×200.

PTx ip:
1. PTx ip has similar effects on motor deficits in EAE: PTx ip (1000 ng) delayed the onset of motor symptoms and decreased the severity of motor impairment ($p<0.01$) (FIG. 11). The inventors evaluated whether A or B subunit alone was effective with equivalent dosage. Neither of them showed therapeutic effect. B subunit alone showed a trend in delaying the onset of motor deficits, but it was not significant (FIG. 11).
2. PTx ip attenuates spinal cord leukocyte infiltration and demyelination in EAE: H&E staining in the cross-sectional of the spinal cord of EAE mice showed widespread infiltration of inflammatory cells in the spinal cord. By contrast, EAE+PTx ip mice exhibited markedly decreased infiltration of inflammatory cells in the spinal cord (FIG. 12). This is consistent with Luxol fast blue staining which observed widespread demyelination zones in the white matter of the spinal cord of EAE mice compared to EAE+PTx ip mice (FIG. 13).
3. PTx ip attenuates macrophage/microglia infiltration to the CNS: In the brain and spinal cord of EAE mice, anti-Iba1 antibody reacted strongly with amoeboid-shaped cells, corresponding to activated microglia. Wild type controls manifest ramified or resting microglia; whereas EAE+PTx ip mice manifest intermediate responsiveness and ramification (FIG. 14).

Example 22

VEGF and Angiogenesis—Generally

Vascular endothelial growth factor (VEGF) and angiogenesis play an important role in the pathophysiology of experimental autoimmune encephalomyelitis (EAE) and multiple sclerosis (MS). The inventors investigated whether PTx can increase VEGF expression and angiogenesis which in turn lead to beneficial effects in EAE model. EAE was induced as by MOG 35-55 in C57BL/6 mice. Clinical scores of EAE were evaluated daily for 19 days. Brain and spinal cord samples were stained by hematoxylin and eosin (H&E), Luxol fast blue/periodic acid Schiff agent (LFB/PAS) and immunohistochemistry for VEGF, NeuN and Collagen IV. Western blot protein analysis was used to assess the protein levels of VEGF and collagen IV. In vitro study on primary neuronal culture was done to assess the effect of PTx on VEGF expression on neurons. The inventors found that the treatment of PTx attenuates inflammation and demyelination and therefore the clinical deficits in EAE. PTx increases VEGF expression and angiogenesis in vivo and in vitro. The findings suggest that upregulation of endogenous VEGF on neurons plays a protective role in EAE and it is a potential target in treatment for multiple sclerosis.

Example 23

VEGF and Angiogenesis—Animals and EAE Induction

All experimental procedures were approved by the Institutional Animal Care and Use Committee of the Barrow Neurological Institute and performed according to the Revised Guide for the Care and Use of Laboratory Animals.

The animals were kept in groups on a 12:12 h light/dark cycle with food and water ad libitum.

EAE was induced. Briefly, female C57BL/6 mice (6-8 weeks old, Taconic Laboratory, New York, USA) were subcutaneously injected with 200 µg myelin oligodendrocyte glycoprotein (MOG35-55; ME V G W Y R S PFS RV V H L Y R N G K, Bio-synthesis Inc. Lewisville, TX), dissolved in an emulsion of 50 µl of complete Freund's adjuvant containing 0.5 mg of heat killed *Mycobacterium tuberculosis* (CFA, Difco Laboratories, Detroit, MI) and 50 µl of phosphate buffered saline (PBS). On the day of immunization (day 0) and 48 h later (day 2), PTx (List Biological laboratories Inc.) 200 ng in PBS was injected intraperitoneally (ip). An additional 1000 ng PTx was administered ip on day 7 in the PTx treatment group.

Neurological functional tests were performed by an examiner blinded to the treatment status of each animal. Clinical grades of EAE were assessed using a five-point standardized rating scale: 0=no deficit; 1=tail paralysis; 2=unilateral hind limb weakness; 3=incomplete bilateral hind limb paralysis and/or partial forelimb weakness; 4=complete hind limb paralysis and partial forelimb weakness; 5=moribund state or death. Functional data were collected on 3 mouse groups (n=12/group): normal control group, EAE group and PTx treatment group. Scores were recorded daily.

Example 24

VEGF and Angiogenesis—Immunohistochemistry

Mice were euthanized at day 19 post immunization. Terminally anesthetized mice were perfused intracardiacally with saline followed by 4% paraformaldehyde. The fixed spinal cord and brain were embedded in paraffin and cut into serial 6 µm thick coronal slides. Histological evaluation was performed by staining with hematoxylin and eosin (H&E), Luxol fast blue/periodic acid Schiff agent (LFB/PAS) to assess inflammation and demyelination respectively.

Histological scores assessing the degree of inflammation and demyelination in the spinal cord and brain were evaluated using a semi-quantitative system. In brief, the degree of inflammation was assessed by counting the number of cellular infiltrates in the spinal cord. Digital images were collected using an Axoplan microscope (Zeiss, Thornwood, NY) under bright field setting using a 40× objective. Severity of inflammatory cell infiltration on H&E staining was scored using the following scale as described (Okuda et al., 1999): 0=no inflammation; 1=cellular infiltrates only around blood vessel and meninges; 2=mild cellular infiltrates in parenchyma (1-10/section); 3=moderate cellular infiltrates in parenchyma (11-100/section); and 4=severe cellular infiltrates in parenchyma (>100/section).

Serial sections of paraformaldehyde-fixed spinal cord and brain were stained with Luxol fast blue for myelin and were assessed in a blinded fashion for demyelination using the following scale: 0=normal white matter; 1=rare foci; 2=a few areas of demyelination; 3=confluent perivascular or subpial demyelination; 4=massive perivascular and subpial demyelination involving one half of the spinal cord or brain with presence of cellular infiltrates in the CNS parenchyma; and 5=extensive perivascular and subpial demyelination involving the whole cord section or brain with presence of cellular infiltrates in the CNS parenchyma. At least six serial sections of each spinal cord from each mouse were scored and statistically analyzed by ANOVA. Data were presented as Mean±Standard deviation (SD).

Immunohistochemistry was performed with antibodies against VEGF (NG1651636, Millipore Corporation, Billerica, MA) to identify pro-angiogenesis factors; and against Nestin (LV1634942, Millipore Corporation, Billerica, MA) and Collagen IV (ab19808, Abcam Inc., Cambridge, MA) to identify the density of blood vessels. Immunolabeling was detected by applying the peroxidase-antiperoxidase procedure with 3,3'-diaminobenzidine (DAB) as cosubstrate.

For double fluorescent staining, antibodies against NeuN (MAB377, Millipore Corporation, Billerica, MA) and VEGF (NG1651636, Millipore Corporation, Billerica, MA) were used to identify the expression of VEGF on neurons. The sections were incubated in 5% FBS in PBST for 1 hour, and then incubated in the mixture of two primary antibodies for 1 hour at room temperature, followed by incubation with two fluorescent conjugated secondary antibodies (FITC conjugated and Texas Red conjugated) in PBST for 30 min at room temperature. Adjacent sections were used to detect co-localization. Respective negative controls that omit primary antibodies and positive controls were applied for each case.

Example 25

VEGF and Angiogenesis—Western Blot Protein Analysis

Aliquots of equal amount of proteins were loaded onto an 8% SDS-polyacrylamide gel. After gel electrophoresis, blots were subsequently probed with primary antibodies (VEGF, collagen IV). For detection, horseradish peroxidase-conjugated secondary antibody was used (7074, Cell signaling technology; Danvers, MA), followed by enhanced chemiluminescence development (ECL kit, 34077, Thermo Scientific Pierce, Rockford IL).

Normalization of results was ensured by running parallel Western blots with (3-actin antibody (sc-47778, Santa Cruz Biotechnology, Inc., Santa Cruz, CA). The optical density was quantified using an image densitometer (Model GS-670, BioRad, Hercules, CA). The data are presented as a percentage of target protein relative to (3-actin. A value of $p<0.05$ is considered significant.

Example 26

VEGF and Angiogenesis—In Vitro

To prepare primary neuronal culture, cells were collected from cerebral cortices of 0 or 1-day-old C57/BL6 mouse pups (Taconic, Hudson, NY). Pups were dipped in 95% ethanol inside a cell culture hood. The whole brains were exposed and the meninges were removed under a dissecting microscope. Both sides of cortex were removed and put into dish with Neurobasal Medium (Invitrogen Corporation, CA). The cortices were cut and minced mechanically. Tissues were incubated in Papain digestion solution (Worthington, Biochemical, Lakewood) at 37° C. for 20 minutes with continuous shaking (150 rpm). Digestion was stopped by addition of 10% FBS (Sigma, St. Louis, MO) and filtered through a 70 um cell strainer. It was centrifuged for 3 min (1500 rpm) and the supernatant was discarded. 2 ml Neurobasal Medium supplemented with 0.5% L-glutamine and 2% B27 serum-free supplement (Invitrogen Corporation, CA) was added to re-suspend the cells in a flask. Cells were plated into Poly-D-lysine covered dishes. They were cultured in 5% CO2 atmosphere at 37° C. Medium was replaced every 3-4 days.

On day 7, primary neuronal cells were treated with PTx at the concentration of 100 ng/ml or 400 ng/ml. 24 hours after treatment, the cells were fixed with 4% paraformaldehyde. Cells were double stained with antibodies VEGF (NG1651636, Millipore Corporation, Billerica, MA) and Map2 (3-1103, Gainesville, FL) to measure the expression of VEGF on neurons. The expression of PTx on neurons was evaluated by calculating the mean density with the VisionWorks LS Image Acquisition and Analysis Software.

Example 27

VEGF and Angiogenesis—the Treatment of PTx Attenuated Clinical Deficits of EAE

To investigate whether the treatment of PTx alleviated clinical deficits of EAE, clinical scores were evaluated daily in each group (control, EAE and PTx). After MOG induction, motor symptoms were observed on day 13 and continued to worsen up to day 19 in the EAE group. In the PTx treatment group, no clinical signs were observed during the same period.

Example 28

VEGF and Angiogenesis—the Treatment of PTx Attenuated Inflammation and Demyelination in EAE At day 19 after immunization, mice were sacrificed to detected the inflammation and demyelination by H&E and Luxol fast blue staining. Infiltrating inflammatory cells were abundant around blood vessels and in the parenchyma of brain and spinal cord in the EAE group. In the PTx treatment group, the number of inflammatory cells were markedly reduced (FIG. 2). Massive perivascular and subpial demyelination with inflammatory cells infiltrating the parenchyma were seen especially in the spinal cord in the EAE group. In the PTx treatment group, few foci of demyelination were observed. Semi-quantitative analysis showed there was a significant difference in the degree of inflammation and demyelination in the brain and spinal cord between EAE and PTx treatment groups (Table 3).

Example 29

VEGF and Angiogenesis—PTx Increased VEGF Expression and Angiogenesis

Sections were stained with antibodies of VEGF and collagen IV to detect change of angiogenesis in different groups. Expression of VEGF on the cells located in brain cortex and spinal gray matter was increased significantly in the PTx treatment group. Double staining with VEGF and NeuN antibodies confirmed these cells were neurons. Consistently, blood vessel counts by collagen IV staining were increased significantly in the PTx treatment group. In the inflammatory cell infiltrating sites and demyelination lesion areas in the EAE group, the expression of VEGF and blood vessel counts were increased, but the overall protein levels of VEGF and collagen type IV by Western blot were decreased ($p<0.05$).

Example 30

VEGF and Angiogenesis—PTx Increased the Expression of VEGF In Vitro

To further delineate the effect of PTx on VEGF expression in vitro, the inventors cultured primary neurons. On day 7, neuronal cells were treated with PTx at the concentration of 100 and 400 mg/ml. The expression of VEGF after 24-hour treatment was significantly increased and this increase was dose-dependent ($p<0.01$).

Example 31

VEGF and Angiogenesis—Table 3

Table 3 depicts semi-quantification analysis of inflammation and demyelination in the brain and spinal cord at 19 days after immunization.

TABLE 3

|  | EAE | EAE + PTx | P value |
| --- | --- | --- | --- |
| Inflammation (H and E) | | | |
| Brain | 3.4 +/− 0.55 | 1.2 +/− 0.45 | 0.0001 |
| Spinal cord | 3.6 +/− 0.55 | 1.4 +/− 0.55 | 0.0002 |
| Demyelination (Fast Blue) | | | |
| Brain | 3.6 +/− 0.55 | 1.0 +/− 0.71 | 0.0002 |
| Spinal cord | 4.2 +/− 0.84 | 1.4 +/− 0.55 | 0.0002 |

Example 32

VEGF and Angiogenesis

As described herein, the inventors demonstrated that PTx treatment increases VEGF expression and angiogenesis. They have also shown that the increase of VEGF is from neurons and blood vessel density is increased in brain cortex and spinal gray matter. In vitro study has further established the dose-dependent effect of PTx on VEGF expression. Importantly, the inventors found that angiogenesis plays a protective role in EAE and that improving angiogenesis is one of the mechanisms of PTx preventing central nervous system autoimmune disease in the EAE model.

VEGF and angiogenesis play a role in EAE. Although the inventors found an upregulation of VEGF and vessel counts in the lesion areas in EAE, this transient increase is likely local and reactive to inflammation. It doesn't alert the overall decrease in VEGF and angiogenesis in EAE. This would explain the seemingly contradictory results in previous studies.

Neuronal VEGF plays a protective role in most CNS diseases. Studies demonstrated that VEGF has neuroprotective effects and can stimulate neuron outgrowth and survival. Neuron degeneration in motor system diseases has been linked to down regulation of endogenous VEGF, such as amyotrophic lateral sclerosis (ALS) and Kennedy disease. It also has been demonstrated that down regulated VEGF by genetic manipulation results in degeneration of motor neurons. Interestingly, it has been previously reported that within the spinal cord in the course of autoimmune encephalomyelitis not only myelin but also neurons are subject to lymphocyte attack and may degenerate. Loss of neurons has been demonstrated in EAE. The inventors found the expression of VEGF on neurons was up regulated significantly after PTx treatment, and administration of PTx prevented the inflammation and demyelination in EAE. This supports that up regulation of neuronal VEGF play a protective role in EAE.

In summary, the inventors have shown that administration of PTx attenuates the inflammation and demyelination in EAE through up regulating endogenous VEGF on neurons and angiogenesis. The findings support that endogenous VEGF on neurons plays a protective role in EAE and it is a potential target in treatment for multiple sclerosis.

Example 33

Materials and Methods for Examples 34-38

All methodologies contained herein are from Z. Tang et al., *Pertussis toxin reduces calcium influx to protect ischemic stroke in a middle cerebral artery occlusion model*. J. of Neurochemistry 2015, vol. 135, 998-1006. This reference is incorporated by reference in its entirety for all purposes.

C57BL/6 mice were purchased from Taconic (Oxnard, CA, USA). All animals were housed in pathogen free conditions at the animal facilities of the Barrow Neurological Institute. All experimental procedures were approved by the Institutional Animal Care and Use Committee of the Barrow Neurological Institute and performed according to the Revised Guide for the Care and Use of Laboratory Animals.

Thirty (30) C57BL/6 male mice (age 10-14 weeks) were randomly divided into either a PTx-treatment group or a control group, i.e. 15 mice in each group. The average weight was 25.3±1.4 g in the PTx-treatment group and 24.4±1.8 g in the control group. Randomization was based on alternating selection of mice whoever came the next upon arrival. People who performed the surgery, immunohistochemistry and magnetic resonance imaging (MRI) were blinded to the randomization.

Mice were under Ketamine/Xylazine anesthesia (80 mg/kg Ketamine and 10 mg/kg Xylazine, injected intraperitoneal, i.p.). Standard aseptic surgical procedures were used throughout the procedure. The animals were kept warm with a carefully monitored heating lamp to maintain body temperature at 37° C. during surgery and recovery after surgery. Following the induction of anesthesia, the surgical site was cleaned, and the hair was shaved with an electric razor. The exposed skin was then disinfected. Ophthalmic ointment was applied to the eyes to prevent drying during the procedure. A 6-0 surgical nylon monofilament with a rounded tip was introduced into the right internal carotid artery through the external carotid stump. It was then advanced 10-11 mm past the carotid bifurcation until a slight resistance was felt. At this point, the intraluminal filament blocked the origin of the middle cerebral artery. After the permanent middle cerebral artery occlusion (pMCAO) procedure, mice were monitored carefully to assure temperature regulation while recovering from anesthesia. Mice was housed one per cage for recovery. Food, water, and hydrating gel were made available on the floor of the cage. Mice were monitored daily for any signs of infection, and antibiotics would be administered as needed. In our experience, surgical site infections were uncommon. Analgesics would be administered for any signs of distress, as per animal care facility guidelines.

MRI was performed on a 7T small animal MRI, 30-cm horizontal-bore magnet, and a BioSpec Avance III spectrometer (Bruker Daltonics Inc., Fremont, CA, USA) with a 116-mm high power gradient set (600 mT/m) and a 72-mm whole-body mouse transmit/surface coil configuration. Isoflurane anesthesia was induced and maintained for each animal at 3% and 1.5% respectively. It was delivered with medical air at 1.5 L/min. During MRI scan, the animal's respiration was continually monitored by a small animal monitoring and gating system (SA Instruments, Stoney Brook, NY, USA) via a pillow sensor positioned under the abdomen. Mice were placed on a heated circulating water blanket (Bruker, Billerica, MA, USA) to maintain body temperature at 36-37° C. T2-weighted images were acquired 24 h after pMCAO to assess the infarct volume, using a Rapid Acquisition with Refocused Echoes sequence with parameters: TR=3000 ms, effective TE=60 ms, Rapid Acquisition with Refocused Echoes factor=8.20 slices were acquired with thickness=0.5 mm, field of view 2.56×2.56 cm, matrix 128×128, total scan time 3 min 12 s. In order to assess the cerebral blood flow (CBF) in the MCA territory, images were acquired 24 h after pMCAO, using a Continuous Arterial Spin Labeling sequence with parameters: TR=3000 ms, TE=6.95 ms, segments=4, slice thickness=1.5 mm, field of view 2.0×2.0 cm, matrix 64×64, total scan time 20 min. MRI data were analyzed using the MEDx3.4.3 software package (Medical Numerics, Germantown, MD, USA) on a LINUX workstation.

Mice were euthanized with isoflurane anesthesia at 24 h after inducing pMCAO. They were then perfused intracardiacally with saline followed by 4% paraformaldehyde for a total of 30 min. The fixed brain was embedded in paraffin and cut into serial 6 μm thick coronal slides. Immunohistochemistry was performed with antibodies against caspase-3 (#9662S; Cell Signaling Technology, Beverly, MA, USA). Immunolabeling was detected by applying the peroxidase-antiperoxidase procedure with 3,3'-diaminobenzidine as a co-substrate. Respective negative controls that omit primary antibodies and positive controls were applied for each case. Digital images were collected by using a microscope (Bx53; Olympus America Inc., Center Valley, PA, USA) under the bright field setting. The number and the density of positively stained cells were counted at 40× magnification in matched sections. Results were presented as positive cells per $mm^2$, with areas measured from 40× images using Image J.1.34vi software (National Institutes of Health, Bethesda, MD, USA).

To prepare primary neuronal culture, cells were collected from cerebral cortices of 0 or 1-day-old C57/BL6 mouse pups (Taconic, Hudson, NY, USA). Pups were dipped in 95% ethanol inside a cell culture hood at 23-25° C. The meninges were removed under a dissecting microscope on top of ice. The cortices were cut and minced mechanically in the Neurobasal Medium (#21103-049; Life technologies, Grand Island, NY, USA). Tissues were incubated in Papain digestion solution (#LS003124; Worthington Biochemical Corporation, Lakewood, NJ, USA) at 37° C. for 20 min with continuous shaking (150 rpm, ThermoScientific MaxQ5000 shaker, Waltham, MA, USA). Digestion was stopped by adding 10% Fetal Bovine Serum (#f2442; Sigma-Aldrich Co, St Louis, MO, USA). The solution was filtered through a 70 μm cell strainer. It was centrifuged for 3 min (250 g) to remove the supernatant at 23-25° C. Re-suspended cells were placed into Poly-D-lysine covered dishes in the Neurobasal Medium supplemented with 0.5% L-glutamine and 2% B27 serum-free supplement (#17504-001; Life Technologies). They were cultured in the 5% $CO_2$ atmosphere at 37° C. Medium was replaced every 3-4 days.

Glutamate excitotoxicity was measured using the lactate dehydrogenase (LDH)-based CytoTox96-non-radioactive cytotoxicity assay kit (TOX7; Sigma-Aldrich Co) in accordance with the manufacturer's protocol. The absorbance was measure at 490 nm. Each assay was tested in triplicate. Percentage of specific lysis was determined as: (Experimental release—target spontaneous release)/(Target maximum release—target spontaneous release)×100. The maximum release was determined by detecting the absorbance of the target cells lysed with LDH assay lysis solution. Viability of glutamate-treated neurons was tested by 3-(4,5-dimethylthiazol-2-yl)-2,5-diphenyl-tetrazolium bromide (MTT) assay. Data were expressed as percentage of viable cells compared with the control culture.

On day 10, primary neurons on coverslips were washed in warmed Hank's balanced salt solution (HBSS). They were then incubated in a 35 mm dish containing 2 mL Fluo-3/AM work solution (3 µM Fluo-3/AM in HBSS) for 20 min at 37° C. Coverslips were washed again in HBSS and placed on the stage of laser scanning confocal microscope (LSM710; Carl Zeiss Inc. Oberkochen, Germany). For live cell calcium imaging, cells were excited with 488 nm light from an argon laser. The emission was detected at 530 nm. The cells were scanned once per second for 240 s. After 60 s of baseline recording in HBSS, cells were exposed to glutamate (50 µM glumatatme+10 µM glycine) in HBSS for 180 s. The intensity of the fluorescence in each cell was recorded, which represented the concentration of intracellular calcium. The intensity of baseline was normalized to 1, and data were presented as folds increased than the baseline.

Power analysis was performed by using online tool developed by Statistical Solutions LLC. According to human PET studies, a normal CBF was averaged 22 mL and the critical neuronal damage CBF was 12-14 mL with a variance of approximate 12 mL. We stratified each group into three subgroups according to relative CBF (rCBF)<0.4, 0.4-0.6, and >0.6. Based on our previous studies, we needed a minimum of four mice in each of the six subgroups to have a power of 0.8 for statistics. We also knew that the mortality rate was about 20% in this model. Therefore, we decided to have a total of 30 mice for the study.

Results are presented as the means±standard deviation. Regression analysis was performed by GraphPad-prism 5 software (GraphPad Software Inc. La Jolla, CA, USA). For exponential regression, the formula is presented as: Y=(Y0−Plateau)×exp (−K×X)+Plateau. Unpaired Student's t-test was used for comparison between two groups, while one way analysis of variance (ANOVA) for multiple groups to determine the significance of the difference.

Example 34

Correlation of CBF and Infarct Volume

Perfusion MRI allows early assessment of CBF during ischemia. We used perfusion MRI to limit variations in infarct size that were caused by variations in cerebrovasculature. The region of interest for perfusion was at the center of MCA territory (FIGS. 23 (a) and (b)). It was represented by three 0.5 mm-thick slices. The infarct volume was measured in these three slices and in all slices, while perfusion was measured in the ipsilateral and contralateral hemispheres in three slices. The rCBF was defined as ipsilateral/contralateral in corresponding regions. Infarction is caused by a reduction in CBF (FIG. 23 (b)). The infarct size was correlated with the degree of reduced CBF. When the rCBF was decreased under 0.4, the infarct volume was the largest: 29.0±5.85 mm$^3$ in the three center slices and 105.7±21.12 mm$^3$ in all slices. When the rCBF was between 0.4 and 0.6, the infarct volume was 5.1±1.08 mm$^3$ in the three center slices and 12.3±3.8 mm$^3$ in all slices. When the rCBF was more than 0.6, no infarction was observed.

Figure 23:
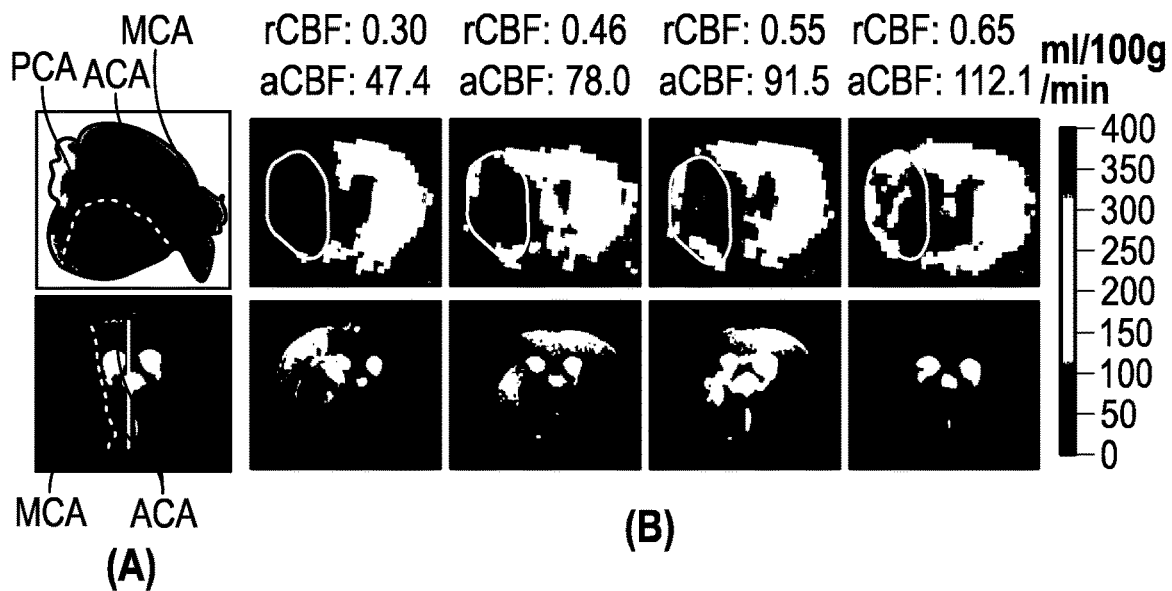
FIG. 23 depicts a correlation of cerebral blood flow (CBF) and infarct volume. (*a*) Shown is the region of interest for CBF (upper panel) and infracted areas (lower panel). (*b*) Representative CBF and T2 weighted magnetic resonance imaging images showing that CBF determines the infarct volume. (*c*1) the correlation between absolute CBF (aCBF) and infarct volume in three slices. (*c*2) the correlation between relative CBF (rCBF) and infarct volume in three slices. (*d*1) the correlation between infarct volume in three slices and all slices. (*d*2) the correlation between rCBF and infarct volume in all slices. Scale bar=1 mm.
Figure 23:
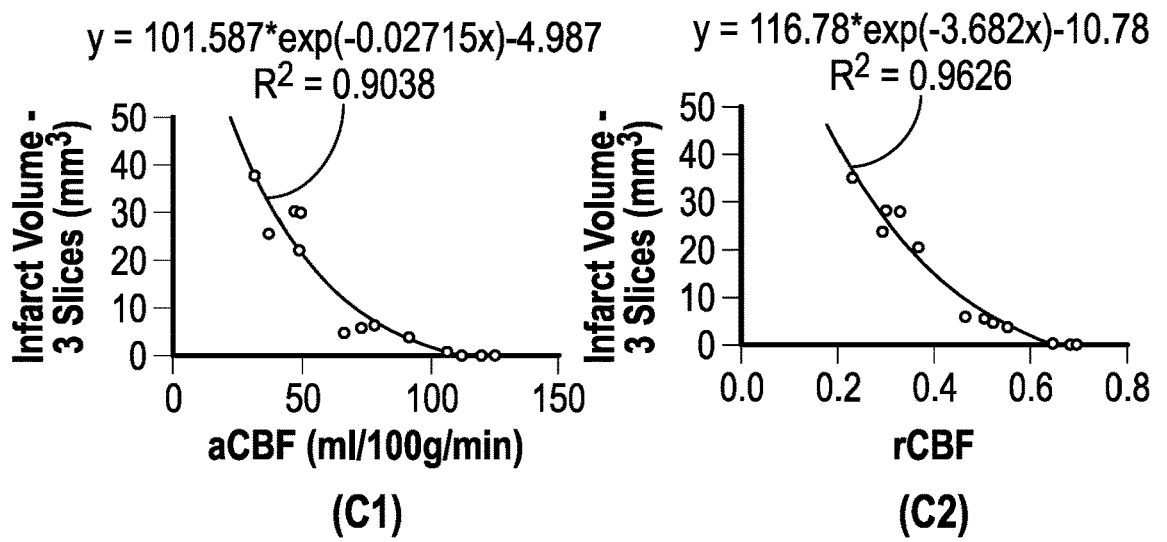
Figure 23:
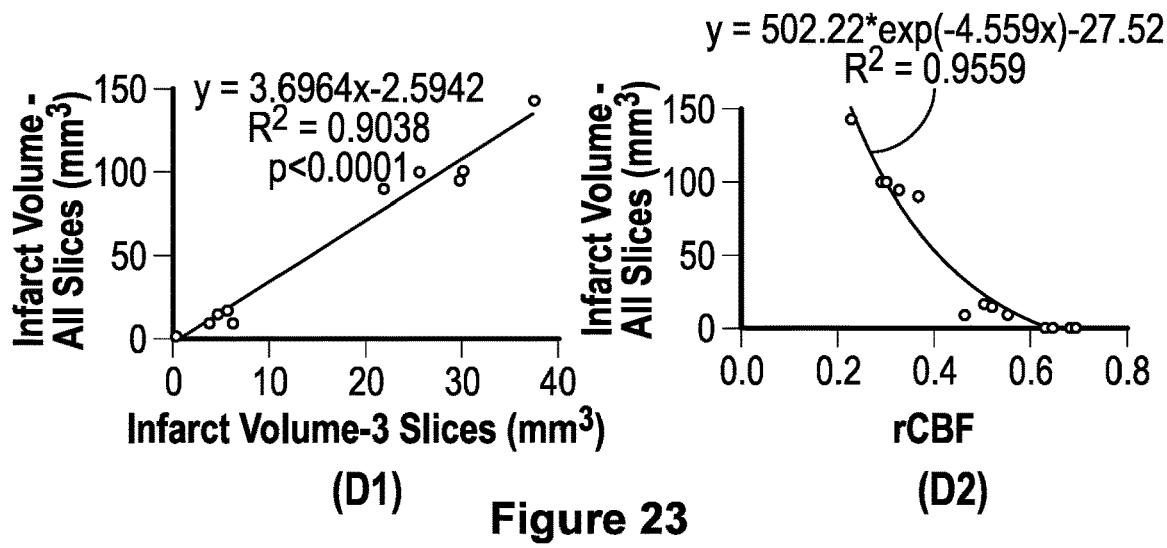

Linear regression was performed to assess infarct volume in the three center slices and in all slices (FIG. 23 (d1)). The correlation coefficient R$^2$ was high (0.9802, p<0.0001), suggesting the three center slices could be used to represent the whole brain involved in MCA stroke. Regression analysis was performed to assess the correlation between CBF and infarct volume. Absolute CBF in the MCA territory was correlated with infarct volume in the three center slices (R$^2$=0.9038) (FIG. 23 (c1)). rCBF showed a slightly better correlation coefficient (R$^2$=0.9626) (FIG. 23 (c2)). Consistently, rCBF was correlated well with infarct volume in all slices (R$^2$=0.9559) (FIG. 23 (c2)).

Example 35

PTx Treatment Attenuated Infarct Volume after pMCAO

Figure 24:
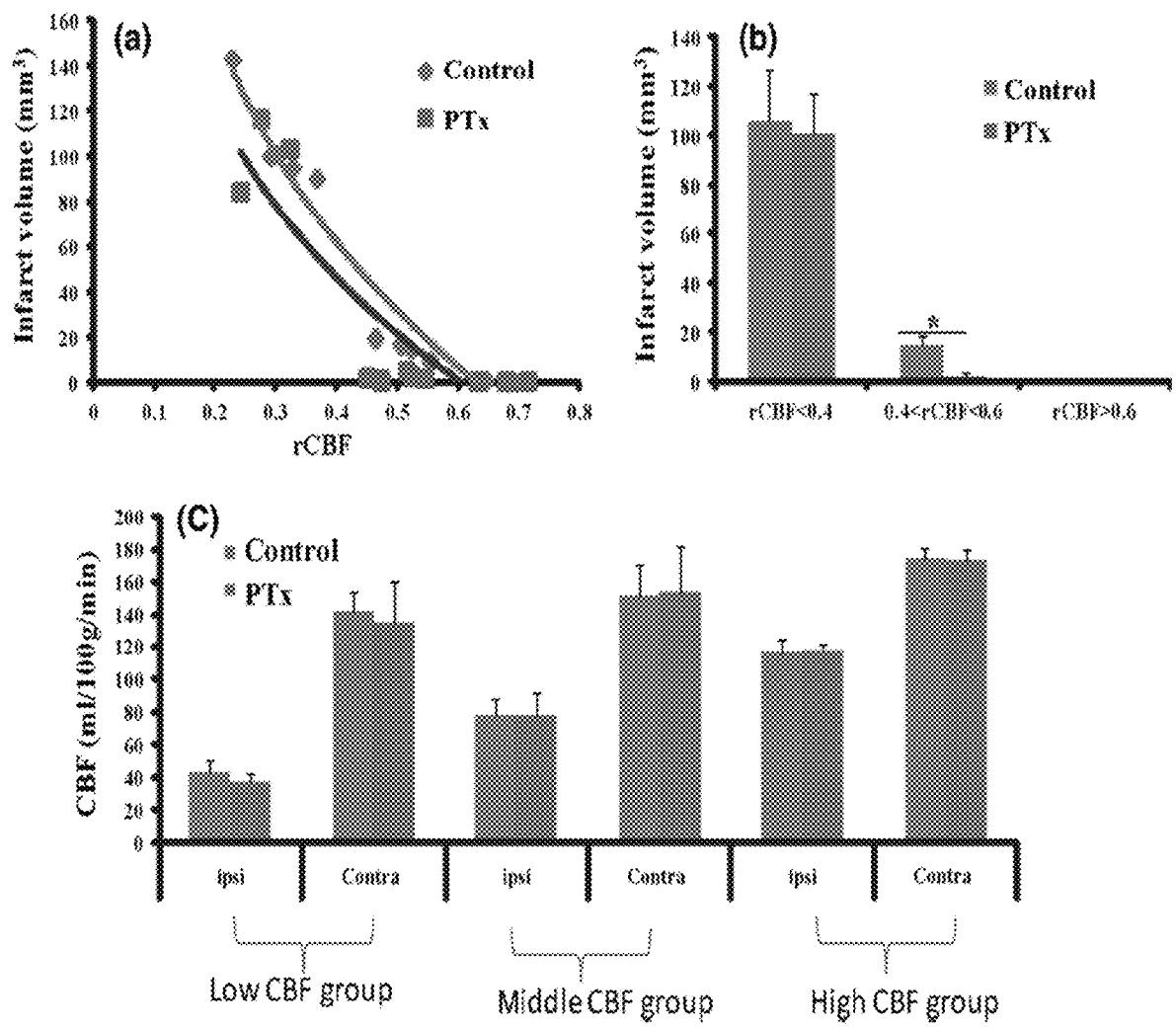
FIG. 24 depicts the fact that PTx treatment attenuated infarct volume after permanent middle cerebral artery occlusion. (*a*) Infarct volume was exponentially dependent on relative cerebral blood flow (rCBF) in both control (blue line, the same data as FIG. 1*d*2) and PTx treated mice (red line). Notice that the exponential model remained valid in predicting infarct volume based on rCBF after PTx treatment. (*b*) When rCBF was between 0.4 and 0.6 (the middle CBF group), PTx treatment attenuated infarct volume (n=5, *p<0.01); PTx treatment did not attenuate the infarct volume when rCBF was lower than 0.4 (the low CBF group); or higher than 0.6 (the high CBF group, virtually no infarction were observed). (*c*) absolute CBF (aCBF) was measured in both ipsilateral and contralateral hemispheres, no significant difference was seen in control and PTx treated mice when they were divided into 3 groups according to the rCBF level.

The mortality rate was 16.7% in the PTx-treatment group and 13.3% in the control group. During the study, two animals died from anesthesia overdose and one from massive stroke in the PTx-treatment group; while one died from anesthesia overdose and one from massive stroke in the control group. We excluded them from the study. The 25 survived mice (12 in PTx group and 13 in the control group) were scanned with MRI to measure the CBF and infarction volume. Regression analysis showed that PTx treatment shifted the exponential model predicting infarct volume based on rCBF (FIG. 24 (a)). When the rCBF was decreased under 0.4, the infarct volume was the largest: 105.7±21.12 mm$^3$ in the control group (n=5) and 101.0±16.01 mm$^3$ in PTx group (n=3, p=0.751). When the rCBF was between 0.4 and 0.6, the infarct volume was reduced by PTx treatment (12.3±3.8 mm$^3$ in the control group, n=4 and 2.12±1.58 mm$^3$ in PTx group, n=5, p<0.01). When the rCBF was more than 0.6 (n=4 each), no lesion was observed in either group (FIG. 24 (b)). Absolute CBF was measured in both ipsilateral (ischemic) and contralateral (non-ischemic) hemispheres in two groups. According to the rCBF, they were divided into three groups: high CBF, middle CBF, and low CBF (FIG. 24 (c)). In the low CBF group, the absolute CBF (aCBF) in the ipsilateral hemisphere was 42.9±7.8 mL/100 g/min in the control group and 37.4±4.4 mL/100 g/min in the PTx treatment group; in the contralateral hemisphere, it was 141.4±12.7 versus 134.7±25.8 mL/100 g/min. In the middle CBF group, it was 77.2±10.6 versus 77.0±14.5 mL/100 g/min in the ipsilateral hemisphere and 151.3±19.3 versus 153.6±28.1 mL/100 g/min in the contralateral hemisphere. In the high CBF group, it was 115.9±8.4 versus 117.4±3.8 mL/100 g/min in the ipsilateral hemisphere and 174.4±6.2 versus 173.3±6.4 mL/100 g/min in the contralateral hemisphere. Thus, PTx treatment did not change the aCBF in either ischemic or non-ischemic sides, suggesting the outcome of PTx treatment as we described next was not a direct effect from enhanced blood flow, but a consequence of neuroprotection in the presence of reduced blood flow.

Example 36

Figure 25:
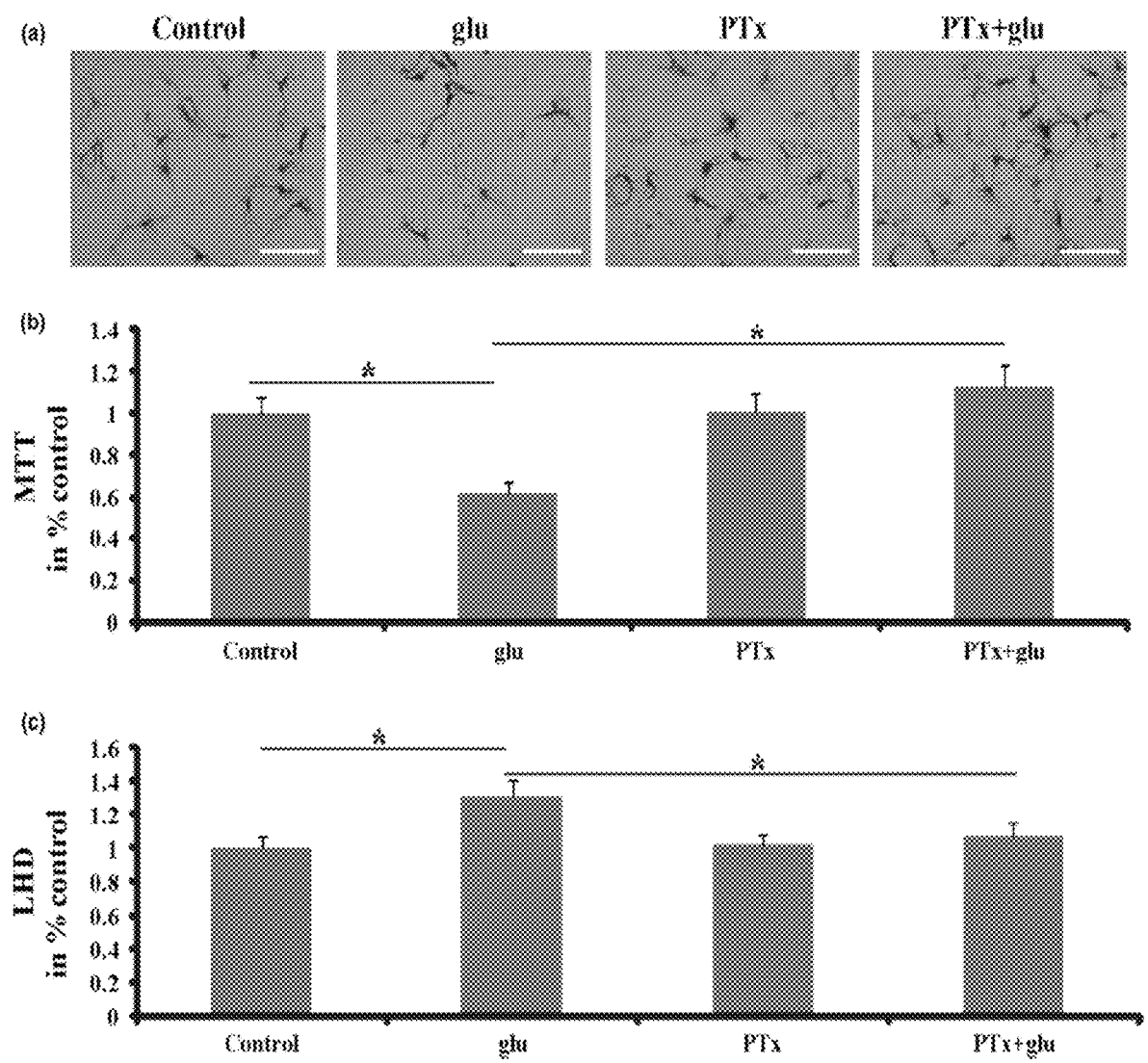
FIG. 25 depicts the fact that PTx treatment protected neurons against glutamate in vitro. (*a*) Representative images of live neurons after 3-(4,5-dimethylthiazol-2-yl)-2,5-diphenyl-tetrazolium bromide (MTT) treatment in four groups, glutamate damaged most neurons and PTx protected neurons against this damage. (*b*) MTT assay was performed to evaluate the neurons survival after glutamate treatment. PTx treatment reduced the neuronal death caused by glutamate. (*c*) lactate dehydrogenase (LDH) release from neurons was calculated in all groups. Glutamate increased the LDH release, while PTx treatment attenuated the increase of LDH (n=6, *p<0.01). Representative images were shown, scale bars=50 μm.

PTx Treatment Increased Neurons Survival after Glutamate-Induced Cell Death In Vitro Primary culture neurons were used to test whether PTx treatment could protect neurons against glutamate excitotoxicity as it often occurs during ischemic stroke. MTT assay showed that glutamate treatment reduced the survival of neurons, while PTx treatment saved them. The survived neurons were reduced to 0.618±0.06 after glutamate treatment (the baseline control was normalized to 1, p<0.01). When PTx was added before the glutamate treatment, the survived neurons increased to 1.1±0.12 (p<0.01, FIGS. 25 (*a*) and (*b*)). LDH is a soluble cytosolic enzyme that is released into the culture medium following loss of membrane integrity. Its release correlates with cell lysis. Glutamate increased LDH release to 1.31±0.11 (the baseline control was normalized to 1, p<0.01). PTx treatment reversed this increase (0.76±0.08, p<0.01, FIG. 25 (*c*)).

Example 37

PTx Treatment Decreased Glutamate-Induced Calcium Influx into Neurons

Figure 26:
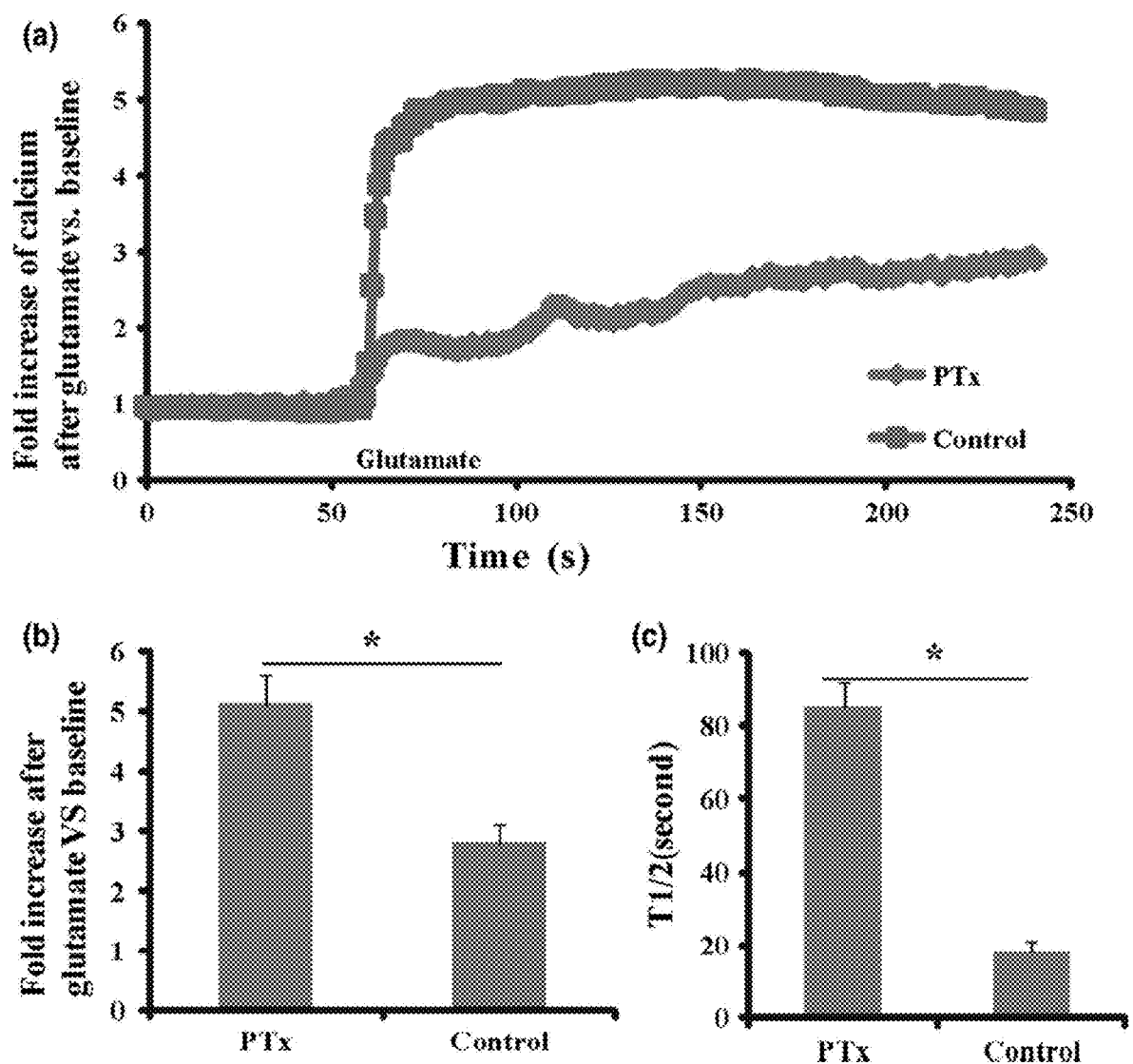
FIG. 26 depicts the fact that PTx treatment reduced calcium influx in neurons. (*a*) Calcium influx in neurons was recorded. Calcium influx in neurons occurred soon after glutamate treatment and reached the peak fast, while PTx treatment decreased the influx dramatically. (*b*) Fold increase of calcium was calculated, which represented the volume of calcium influx. Calcium was increased more than five folds in the control group, while less than three folds were seen in the PTx treatment group. (*c*) Time to reach the half of the peak calcium concentration was recorded, which represented the speed of calcium influx. PTx treatment decreased the speed of calcium influx significantly (n=20, *p<0.01).

Calcium imaging was performed to measure the intracellular calcium. The intensity of fluorescence which represented the concentration of intracellular calcium increased sharply and reached the peak quickly after glutamate was administered. PTx treatment slowed down this rapid increase (T1/2: 18.5±2.5 s in glutamate vs. 85.4±10.2 s in PTx) (FIGS. 26 (*a*) and (*c*)). The peak value represented the maximum amount of calcium influx. It was increased 5.1±0.5 folds compared to the baseline after glutamate stimuli, whereas PTx treatment reduced this increase (2.8±0.3 folds, p<0.01, FIGS. 26 (*a*) and (*b*)).

Example 38

PTx Treatment Prevented Neurons from Apoptosis after pMCAO

Figure 27:
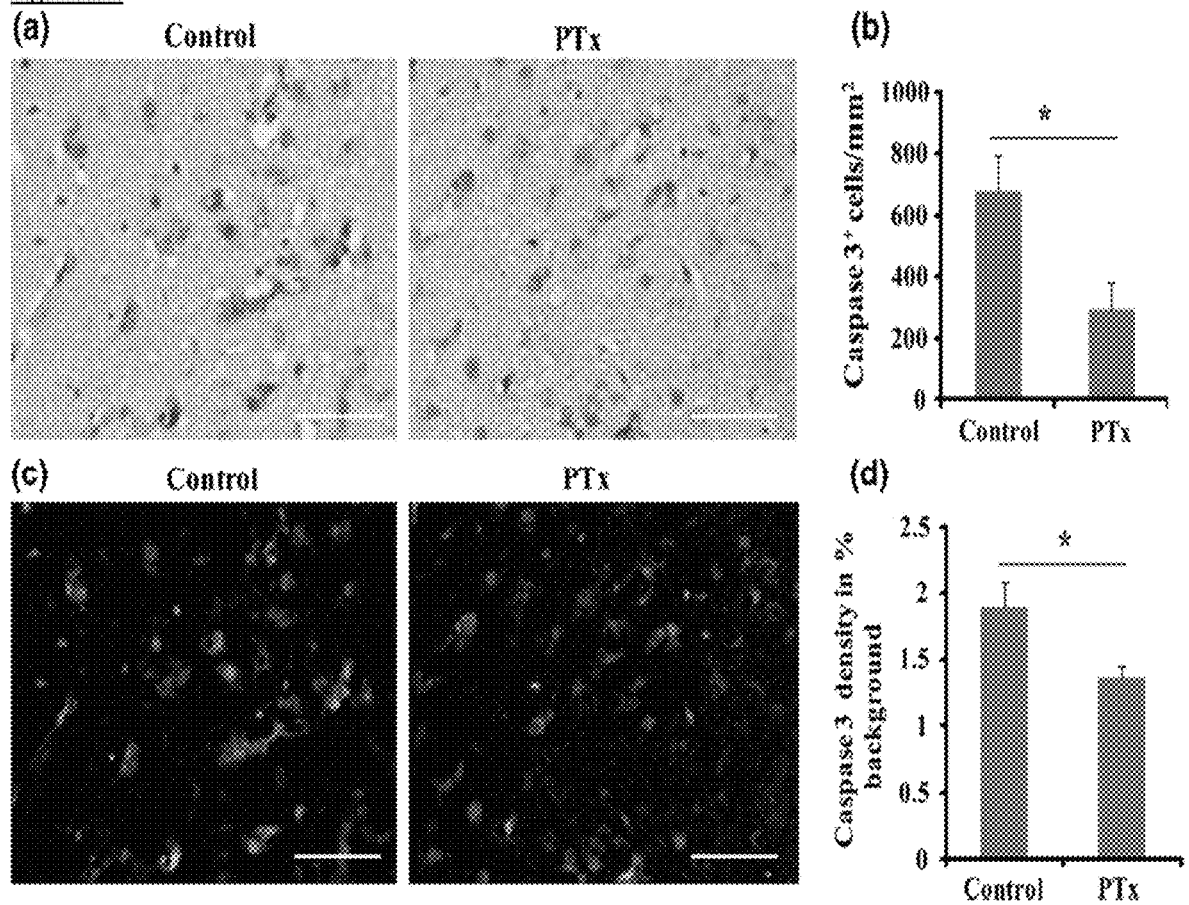
FIG. 27 depicts the fact that PTx treatment decreased the caspase-3 positive cells after permanent middle cerebral artery occlusion. (*a*) Staining with caspase-3 antibody in the ischemic area 24 h after pMCAO, (*b*) semi-quantification analysis of the number of caspase-3 positive cells showing PTx treatment decreased the apoptosis (n=4, *p<0.01), (*c*) Invert images with Image J software to measure the density of caspase-3 positive cells, (*d*) semi-quantification analysis of the density of caspase-3 positive cells showing PTx treatment decreased the caspase-3 density (n=4, *p<0.01). Representative images were shown, scale bars=50 μm.

Cleaved caspase-3 is a marker of apoptosis. PTx treated mice had less cleaved caspase-3 positive cells at 24 h after pMCAO (297.5±83.6/mm$^2$ vs. 677.7±117.8/mm$^2$ in control mice, p<0.01, FIGS. 27 (*a*) and (*b*)). PTx also reduced the density of caspase-3 positive cells (1.36±0.05 vs. 1.89±0.2 in controls, p<0.01, FIGS. 26 (*c*) and (*d*)).

Example 39

Materials and Methods for Examples 40-45

All methodologies contained herein are from Z. Tang et al., *CX3CR1 deficiency suppresses activation and neurotoxicity of mieroglia/macrophage in experimental ischemic stroke*, J. of Neuroinflammation 2014, 11:26. This reference is incorporated by reference in its entirety for all purposes.

Breeding pairs of CX3CR1$^{-/-}$ mice were obtained from The Jackson Laboratory (Bar Harbor, ME, USA). Knockouts were generated by replacing the second exon of the CX3CR1 gene with the enhanced green fluorescent protein (CFP) reporter gene, and backcrossed for more than 10 generations to C57BL/6, Cells under control of the endogenous CX3CR1 locus (that is, microglia, macrophages, dendritic cells, and so forth) in homozygote CX3CR1$^{-/-}$ mice are labeled with GFP and also lack CX3CR1 receptor function, Wild-type (WT) C57BL/6 mice were purchased from Taconic (Oxnard, CA, USA). All animals were housed in pathogen-free conditions at the animal facilities of the Barrow Neurological Institute, Phoenix, AZ. USA. All experimental procedures were approved by the Institutional Animal Care and Use Committee of the Barrow Neurological Institute and performed according to the Revised Guide for the Care and Use of Laboratory Animals.

Adult male mice (aged 10 to 14 weeks, weight 24 to 27 g) were exposed to transient (90 minutes) local cerebral ischemia induced by occlusion of the right middle cerebral artery using an intraluminal filament method. The production of an infarct was confirmed by 2,3,5-triphenyltetrazolium chloride (TTC).

Daily neurological deficit assessment was performed by investigators blinded to the control and MCAO groups as described previously. Rating scale: 0=no deficit, 1=failure to extend left forepaw, 2=decreased grip strength of left forepaw, 3=circling to left by pulling the tail, and 4=spontaneous circling.

Magnetic resonance imaging (MRI) was performed on a 7-T small animal MRI, 30-cm horizontal-bore magnet, and BioSpec Avance III spectrometer (Bruker Daltonics Inc Fremont, CA, USA). In order to assess whether the ischemia and reperfusion were induced successfully, single slice cerebral blood flow (CBE) images were acquired before MCAO, 1 hour after MCAO and 24 hours after reperfusion, using a Continuous Arterial Spin Labeling sequence. Multiple Segments Echo Planer Imaging sequences were used to acquire apparent diffusion coefficient (ADC) values 30 minutes after MCAO to assess the damage volume. T2-weighted images were acquired 24 and 72 hours after MCAO to evaluate the development of ischemic lesions, using a Rapid Acquisition with Refocused Echoes sequence. MRI data were analyzed using the MEDx3.4.3 software package (Medical Numerics Inc., Germantown, MA, USA) on a LINUX workstation.

Reactive oxygen species (ROS) generated in the brain were assessed in live mice by using the Xenogen IVIS200 imager (Caliper Life Sciences, Alameda, CA, USA). Briefly, mice were intraperitoneally injected with 200 mg/kg Luminol (Invitrogen, Carlsbad, CA, USA). After 10 minutes, bioluminescence images were captured with exposure time of 3 minutes. A region of interest tool was used to measure the chemiluminescent intensity of the whole brain, Data were collected as photons per second per centimeter squared using the Living image software (Caliper Life Sciences).

Terminally anesthetized mice were perfused intracardially with saline followed by 4% paraformaldehyde. The fixed brains were embedded in paraffin and cut into serial 6 μm thick coronal slides. Immunohistochemistry was performed with antibodies against Iba-1 (Wako Chemicals USA Inc., Richmond, VA, USA) to identify macrophages and microglia; 4-hydroxy-2-nonenal (4-HNE; Abeam, Cambridge, MA. USA) and 8-hydroxy-2-deoxyguanosine (8-OHdG; Abeam) to identify lipid peroxidation and damaged DNA of oxidative impairment. Immunolabeling was detected by applying the peroxidase-antiperoxidase procedure with 3,3'-diaminobenzidine as a co-substrate. For double immunofluorescent staining, antibodies against NeuN (Millipore, Billerica, MA, USA) and cleaved Caspase-3 (Cell Signaling, Danvers, MA. USA) were used to identify apoptotic neurons. Respective negative controls that omit primary antibodies and positive controls were applied for each case. The positive cells were counted at 20× magnification in matched sections. Results are presented as Iba-1$^+$, 4-HNE$^+$, 8-OHdG$^+$ or cleaved-Caspase-3$^+$/NeuN$^+$ cells per mm$^2$ within areas measured from 20× images using image J.1.34vi software (National Institutes of Health).

Brain homogenates were prepared from WT and CX3CR1$^{-/-}$ mice 72 hours after MCAO. Animals were anesthetized and the brains were removed and immediately frozen in liquid nitrogen. The ipsilateral or contralateral hemisphere was homogenized in RIPA buffer (10 μl/mg brain, Sigma, St. Louis, MO, USA). Protein concentration was measured with bicinchoninic acid Protein Assay kit (Pierce, Appleton, WI, USA). The total protein concentration was adjusted to 1 mg/ml protein extract. The concentrations of IL-1β, IL-6, and TNF-α in brain homogenates were quantified by enzyme-linked immunosorbent assay (ELISA) kits (BioLegend, San Diego, CA, USA) and converted into pg/mg protein extract.

In order to visualize proliferating mononuclear cells in CNS, mice were injected intraperitoneally with 5-bromo-2-deoxyuridine (BrdU) (50 μg/g of mouse weight in saline, Sigma) immediately before the MCAO procedure and again 24, 48, and 60 hours after surgery. At 72 hours after surgery, mice were anesthetized with isoflurane and transcardially perfused with PBS. Brains were removed, and microglia and invading leukocyte isolation was performed according to the standardized protocol described below.

The isolation of microglia and invading leukocytes are based on discontinuous percoll gradients. Briefly, fresh brain tissues were removed from mice and cut into ~2 mm pieces and incubated in 10 mM Hepes/NaOH buffer (10 mM HEPES, 150 mM NaOH, 7 mM KCL, 1 mM $MgCl_2$, 1 mM $MgCl_2$, 0.36 mM $CaCl_2$) containing 1 mg/ml collagenase (Sigma) for 1 hour at 37° C. The tissues were dispersed with a syringe, filtered through a 100-mm wire mesh, and centrifuged at 2,000 rpm for 5 minutes at 4° C. After centrifugation, cell pellets were resuspended in 15 ml 30% Percoll (Amersham Biosciences, Piscataway, NJ, USA), and centrifuged against 70% Percoll in a 50-ml tube for 15 minutes. The cell monolayer at the 30 to 70% Percoll interface was collected and washed once for further staining.

The number of microglia/macrophage, their proliferation properties and inflammatory cytokine secretion were analyzed by flow cytometry. Single cell suspensions prepared from brain tissues were stained with fluorescently labeled antibodies: APC-CD45, PerCP-Cy5.5-CD45, PE-Ly6G, BV421-Ly6G, PE-Cy7-CD11b, PerCP-Cy5.5-BrdU, PE-IL-1β, V450-IL-6, or APC-TNF-a at designed combination. All antibodies and the isotype controls were purchased from BD Biosciences, San Jose, CA, USA. The staining was performed according to the manufacturer's instructions. After staining, samples were analyzed using a FACSAria I flow cytometer (BD Biosciences). To avoid the interference of GFP expressed on CX3CR1$^{-/-}$ microglia/macrophage, fluors such as FITC and Alexafluor 488 that excite in the same spectrum at the same filter sets as GFP were excluded and the proper compensation was performed in flow cytometry. Subsequent data analyses were completed using FACSDiva software or FCS Express 4 software (BD Biosciences).

Microglia/macrophages were enriched from the single-cell suspension of the ischemic hemisphere of MCAO mice using CD11b MicroBeads (Miltenyi Biotec, Auburn, CA, USA), and then sorted via APC-45/PE-Cy7-CD11b/BV421-Ly6G makers from the remaining cells by FACSAria I using Diva software (BD Biosciences). Purity of microglia and macrophages obtained by this approach reached 99%.

Total RNA was extracted from the sorted microglia/macrophages using the RNeasy Micro Kit (Qiagen, Germantown, MD, USA) according to the manufacturer's instructions; 1 μg was used to synthesize the first strand of cDNA using the Superscript First-Strand Synthesis System for real-time PCR (Invitrogen). PCR was performed on the Opticon 2 Real-Time PCR Detection System (Bio-Rad, Hercules, CA, USA) using corresponding primers (Table 1) and iQ™ SYBR Green Supermix (Bio-Rad). Cycle conditions included heating for 5 minutes at 95° C., followed by 40 cycles of 30 seconds at 95° C., 30 seconds at 60° C., and 60 seconds at 72° C. A melt curve analysis was performed to ensure specific amplification. For each target gene, relative levels of expression were normalized against housekeeping gene GAPDH of the same sample. The relative expression levels of the mRNAs were then reported as fold changes versus sham controls.

Results are presented as the means±SEM. Statistical differences between two groups were evaluated by the two-tailed unpaired Student's t-test. Multiple comparisons were performed with two-way analysis of variance accompanied by Bonferroni post-hoc test. Values of P<0.05 were considered significant.

Example 40

Reduction of Infarct Volume and Neurological Deficit by Cx3CR1 Deficiency after Middle Cerebral Artery Occlusion To ensure the success of the MCAO model, CBF of right middle cerebral artery territory was examined at 24 hours before MCAO, and 1 hour and 24 hours following MCAO using high-field MRI. Animals wherein ischemia and reperfusion were induced successfully were selected for further analysis. No significant difference in CBF at baseline (WT, 171.3±9.5 vs CX3CR1$^{-/-}$, 174.2±10.1 ml/100 g/min, P>0.05), ischemia (WT, 33.5±14.3 vs CX3CR1$^{-/-}$, 31.2±13.1 ml/100 g/min, P>0.05) and reperfusion (WT, 160.1±15.1 vs CX3CR1$^{-/-}$, 155±12.3 ml/100 g/min, P>0.05) was observed between WT and CX3CR1$^{-/-}$ mice. Furthermore, ADC (measuring the magnitude of diffusion of water molecules within cerebral tissue) was acquired 30 minutes after MCAO to assess the damage volume of ipsilateral hemisphere. No significant differences in damage volume were observed between CX3CR1$^{-/-}$ and WT mice (WT, 122.2±8.3 mm$^3$; CX3CR1$^{-/-}$, 119.1±6.7 mm$^3$).

Figure 28:
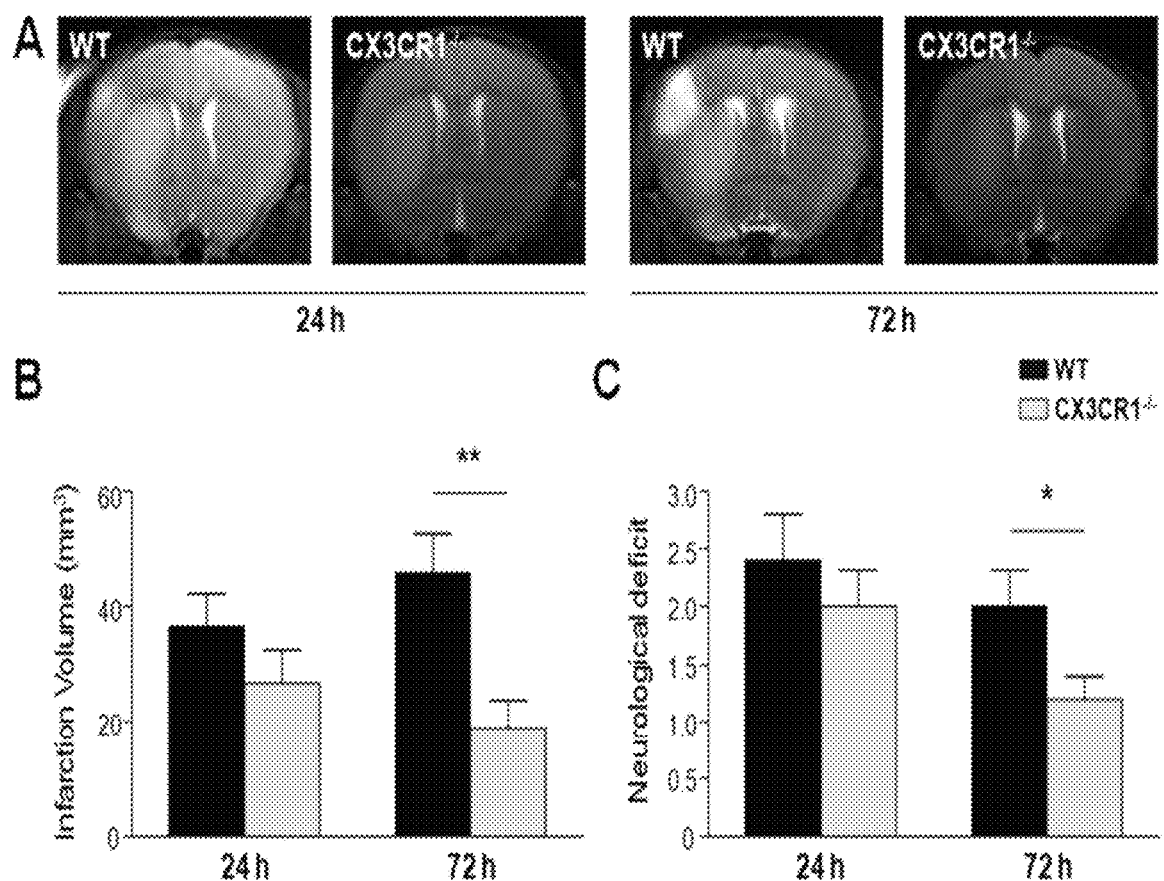
FIG. 28 depicts that CX3CR1 deficiency attenuates infarct volume and neurological deficit after middle cerebral artery occlusion. (A) Infarct volume was assessed by T2-weighted images at 24 and 72 hours post-ischemia. (B) Quantification of T2 images shows that the infarct volume was attenuated by CX3CR1 deficiency 72 hours after middle cerebral artery occlusion (MCAO). P<0.0001 for genotype, P=0.0194 for time point, and P=0.0011 for interaction by two-way analysis of variance. **P<0.01 by Bonferroni post-hoc tests. (C) Clinical assessment demonstrated that CX3CR1$^{-/-}$ mice have better neurological deficit scores than wild-type (WT) mice 72 hours after MCAO. P=0.0049 for genotype, P=0.0262 for time point, and P=0.0062 for interaction by two-way analysis of variance. *P<0.05 by Bonferroni post-hoc tests. n=6 per group.

To assess the infarct volume, T2-weighted images were acquired at 24 and 72 hours following MCAO. The infarct volume in WT mice was 36.5±5.7 mm$^3$ at 24 hours and increased to 45.8±6.8 mm$^3$ at 72 hours. Within CX3CR1$^{-/-}$ mice, infarct volume was 26.9±5.7 mm$^3$ at 24 hours, and a modest but significant decrease (to 19.0±4.9 mm$^3$) was observed at 72 hours (FIG. 28 (A)). Although there was no significant difference in infarct volume at 24 hours between the two groups, CX3CR1$^{-/-}$ mice showed markedly smaller infarct volume at 72 hours relative to WT mice (P<0.01, FIG. 28 (B)). The infarct observed in MRI scan was confirmed by TTC staining.

To further assess the differential response to MCAO in CX3CR1$^{-/-}$ and WT mice, the neurological deficit was assessed daily following MCAO. WT mice had an average clinical score of 2.4±0.4 at 24 hours and 2.0±0.3 at 72 hours, while CX3CR1$^{-/-}$ mice had clinical scores of 2.0±0.3 at 24 hours and 1.2±0.2 at 72 hours indicative of the beginning of recovery at 72 hours in CX3CR1$^{-/-}$ mice but not in WT mice (FIG. 28 (C)).

Example 41

Figure 29:
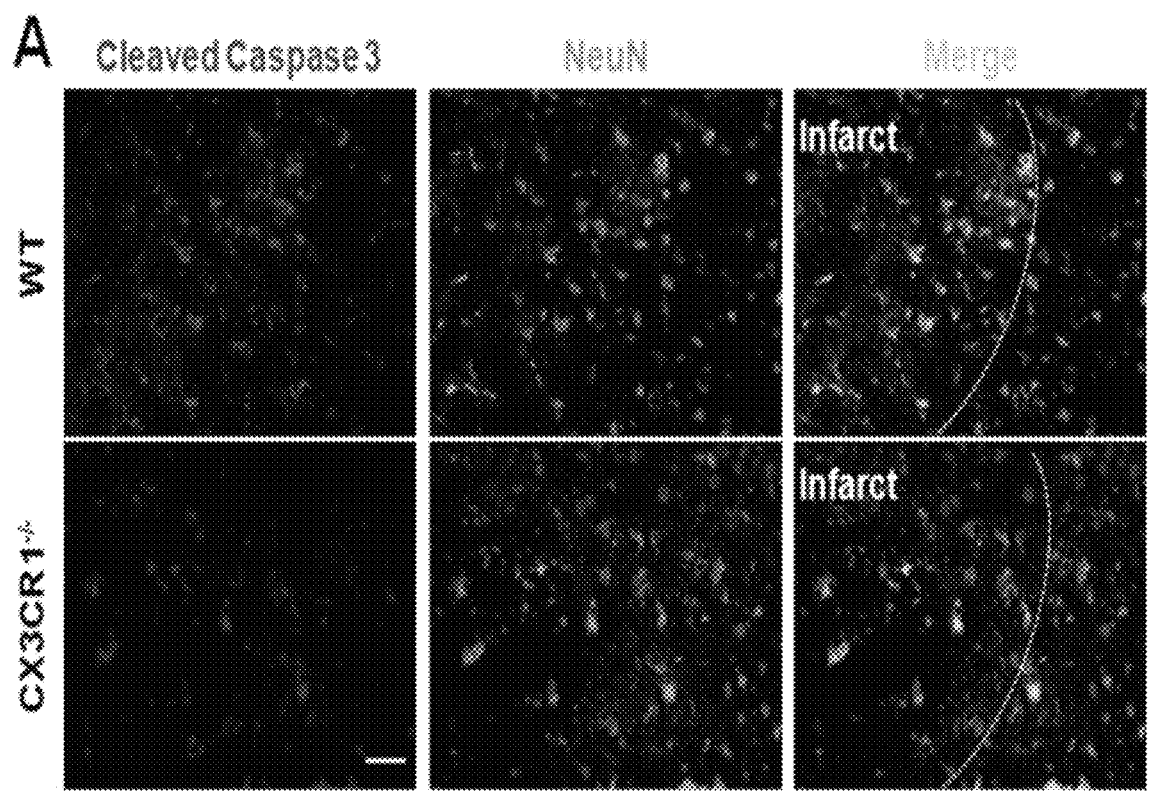
FIG. 29 depicts that CX3CR1 deficiency attenuates neuronal apoptosis after middle cerebral artery occlusion. (A) Double staining with cleaved Caspase 3 (red) and NeuN (green) antibodies in peri-infarct area of wild-type (WT) and CX3CR1$^{-/-}$ mice 72 hours after middle cerebral artery occlusion. (B) Quantification of Cleaved-Caspase 3/NeuN positive cells. CX3CR1$^{-/-}$ mice have fewer Cleaved-Caspase 3$^+$NeuN$^+$ cells in the peri-infarct zone. **P<0.01 by Student's t-test. n=4 per group. Scale bars=50 μm.
Figure 29:
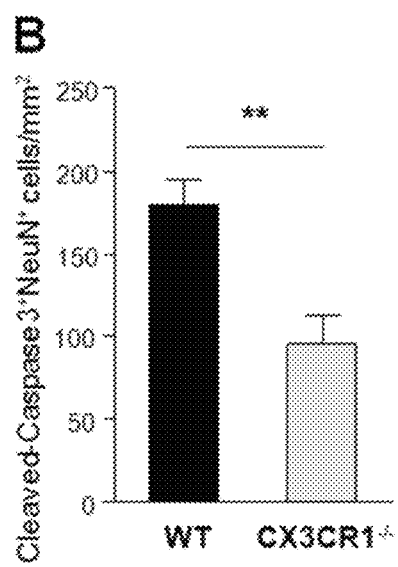

CX3CR1 Deficiency Attenuates Neuronal Apoptosis after Middle Cerebral Artery Occlusion Double staining with NeuN (neuron marker) and cleaved Caspase-3 (apoptotic marker) was performed to investigate whether CX3CR1-dependent differences observed in the size of ischemic damage at 72 hours following MCAO were associated with differential neuronal apoptosis in peri-infarct areas. More cleaved Caspase-3 positive cells were observed in WT mice compared to CX3CR1$^{-/-}$ mice and co-localized with NeuN in most apoptotic cells (FIG. 29 (A)). The number of cleaved Caspase-3 positive neurons was 179.3±15.6/mm$^2$ in WT mice and 95.1±16.9/mm$^2$ in CX3CR1$^{-/-}$ mice 72 hours after MCAO (P<0.01, FIG. 29 (B)). To reveal the phenotype of the other apoptotic cells, double staining of cleaved Caspase-3 with Iba-1 Or GFAP markers, respectively, were employed. These experiments revealed cleaved Caspase-3 positive staining within some microglia and astrocytes (data not shown).

Example 42

Fewer Microglia and Macrophages in Ipsilateral Hemisphere of CX3CR1$^{-/-}$ after Middle Cerebral Artery Occlusion Microglia activation plays an important role in the pathological progression after stroke, and is regulated by CX3CR1. To investigate the effects of CX3CR1 deficiency upon these processes, expression of microglia/macrophage activation marker Iba-1 was examined at different sites of the brain in WT and CX3CR1$^{-/-}$ mice 72 hours following MCAO (FIG. 30 (A)). In the ipsilateral hemisphere of WT mice, the numbers of Iba-1 positive cells in hippocampus, striatum, cortex and peri-infract area (666.1±50.0, 1132.8±96.1, 730.9±68.1, 489.4±56.1/mm$^2$) were significantly higher than those in CX3CR1$^{-/-}$ mice (424.6±43.1, 492.7±42.3, 230.1±20.1, 262.5±29.8/mm$^2$) (FIG. 30 (B)). In the contralateral hemisphere, the numbers of Iba-1 positive cells in the hippocampus, striatum and cortex were similar (307.9±15.5 vs 316.0±14.6, 110.2±11.5 vs 111.8±9.7, 94.0±8.6 vs 92.4±13.1, WT vs CX3CR1$^{-/-}$) regardless of genotype (FIG. 30 (B)).

Figure 30:
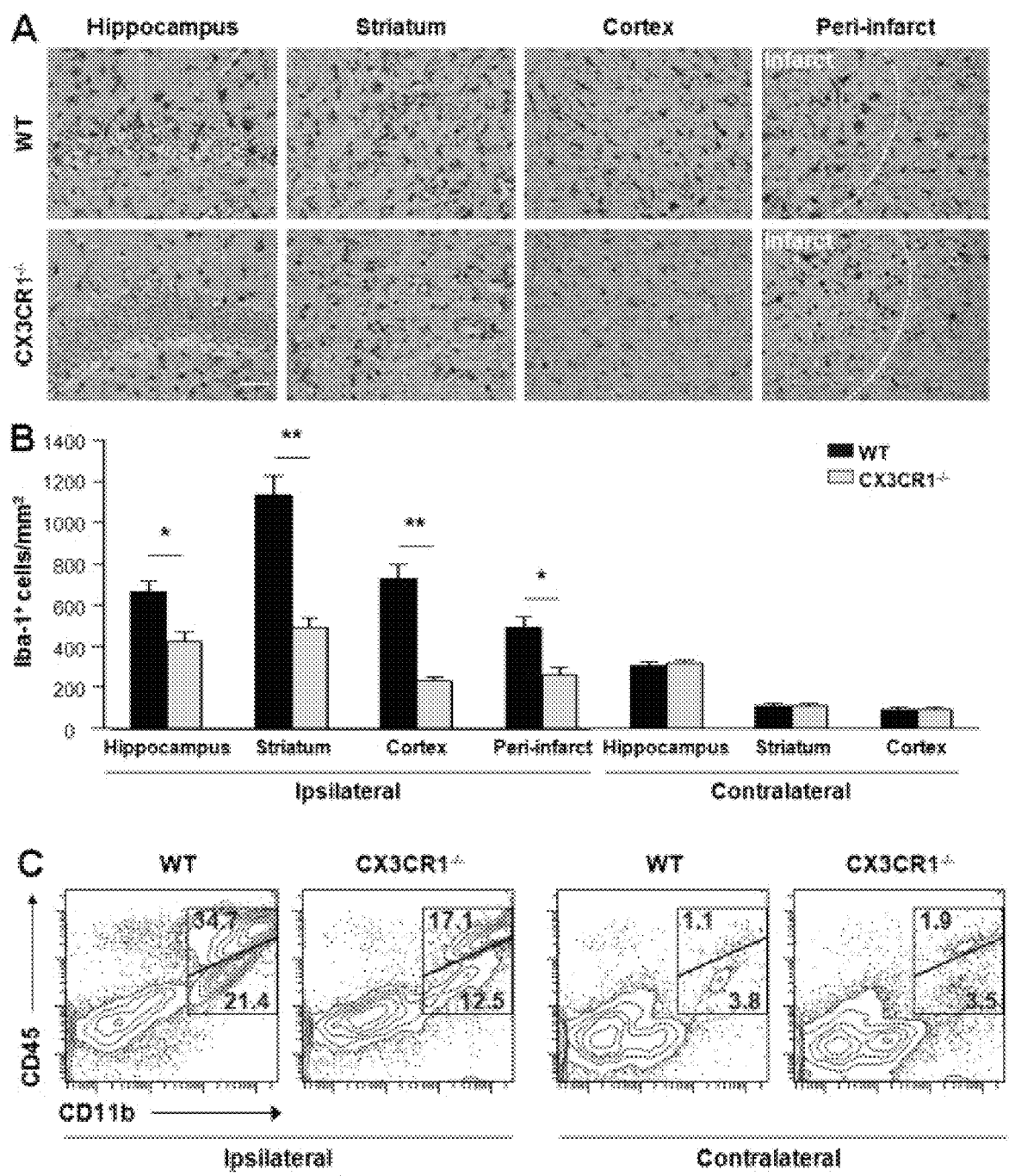
FIG. 30 depicts that CX3CR1 deficiency attenuates infiltration and leads to a different M1/M2 polarization pattern on microglia/macrophages in ipsilateral hemisphere of middle cerebral artery occlusion mice. (A) Staining with anti-Iba-1 antibody in the ipsilateral hippocampus, striatum, cortex and peri-infarct zone of CX3CR1$^{-/-}$ and wild-type (WT) mice 72 hours after middle cerebral artery occlusion (MCAO). (B) Quantification of Iba-1 positive cells. CX3CR1$^{-/-}$ mice have fewer Iba-1 positive cells (macrophages/microglia) in the ipsilateral hippocampus, striatum, cortex and peri-infarct zone, while no differences are observed in these sites of the contralateral hemisphere. P<0.0001 by two-way analysis of variance for genotype, localization and interaction. *P<0.05, P<0.01 by Bonferroni post-hoc tests. n=4 per group. Scale bars=50 μm. (C) Flow cytometry analysis of CD45$^{hi}$/CD11b$^+$ and CD45$^{low}$/CD11b$^+$ cells isolated from the ipsilateral and contralateral hemispheres of CX3CR1$^{-/-}$ and WT mice 72 hours after MCAO by gating on Ly6G$^-$ events (Ly6G vs FSC). (D) Quantification of the number of events in the CD45$^{hi}$/CD11b$^+$/Ly6G$^-$ (left) and CD45$^{low}$/CD11b$^+$/Ly6G$^-$ (right) gate. Statistical analysis shows CX3CR1$^{-/-}$ mice have fewer CD45$^{hi}$/CD11b$^+$/Ly6G$^-$ as well as CD45$^{low}$/CD11b$^+$/Ly6G$^-$ cells in the ipsilateral hemisphere. CD45$^{hi}$/CD11b$^+$/Ly6G$^-$: P=0.0001 for genotype, P<0.0001 for localization and interaction by two-way analysis of variance. CD45$^{low}$/CD11b$^+$/Ly6G$^-$: P=0.0112 for genotype, P<0.0001 for localization, and P=0.0152 for interaction by two-way analysis of variance. P<0.01 by Bonferroni post-hoc tests. n=4 per group. (E) Microglia/macrophage in ischemic hemisphere of CX3CR1$^{-/-}$ brain polarize toward the M2 phenotype. Real-time reverse-transcription polymerase chain reaction was performed using total RNA extracted from sorted CD45$^+$/CD11b$^+$/Ly6G$^-$ microglia/macrophage at 72 hours after MCAO. Data are expressed as fold change vs sham-operated controls. **P<0.01 with Student's t-test for Ym1, Mcr1, and iNOS, respectively. n=4 per group.
Figure 30:
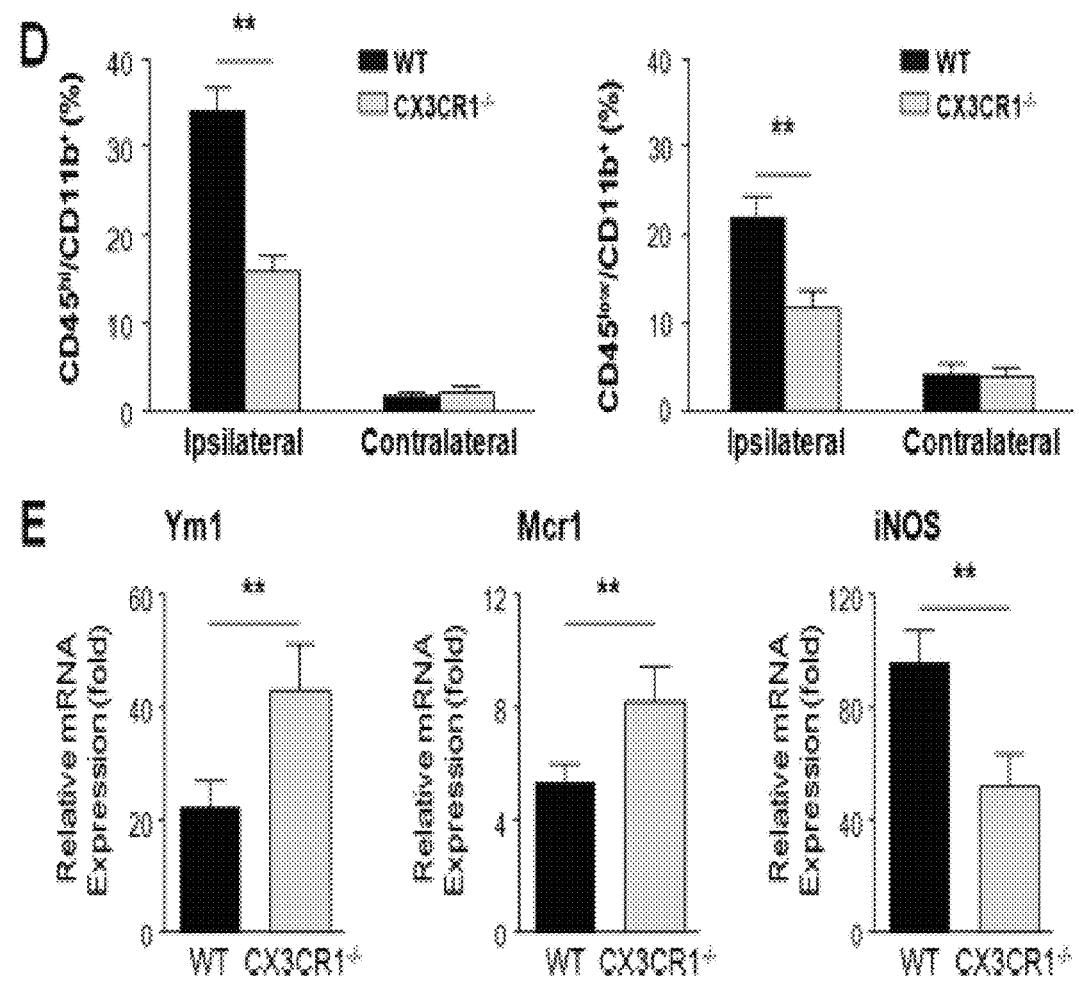

To further distinguish microglia from macrophages within the Iba-1 positive cell population, flow cytometry was used to delineate CD45$^{low}$/CD11b$^+$/Ly6G$^-$ (microglia) and CD45$^{hi}$/CD11b$^+$/Ly6G$^-$ (macrophage/activated microglia) sub-populations within ischemic lesions of WT and CX3CR1$^{-/-}$ mice. As shown in FIGS. 30, (C) and (D), more macrophages/activated microglia infiltrated in the ischemia lesions in WT mice compared to CX3CR1$^{-/-}$ mice (34.1±2.5% vs 15.9±1.8%). In addition, WT mice displayed more CD45$^{low}$ microglia than CX3CR1$^{-/-}$ mice (22.1±2.3% vs 11.7±2.1%, FIGS. 30 (C) and (D)). Both cell populations were similar in WT and CX3CR1$^{-/-}$ mice in the control (non-ischemic) contralateral hemisphere (FIGS. 30 (C) and (D)).

Following ischemia, activated microglia/macrophage can potentially exert either a protective or detrimental effect, suggesting that these cells may acquire different phenotypes belonging to the classical (M1) or to the alternative (M2) active status. We found that activated M1-like Iba-1$^+$ cells, which have shorter and thicker processes and bigger cell bodies, were visualized in the WT brain section, while ramified M2-like Iba-1$^+$ cells were predominantly located in the CX3CR1$^{-/-}$ brain (FIG. 30 (A)). To evaluate their M1/M2 polarization, we sorted and purified microglia/macrophages (CD45$^+$/CD11b$^+$/Ly6G$^-$) from the ischemic hemisphere of CX3CR1$^{-/-}$ and WT MCAO mice brain. Using real-time PCR, we found that the levels of tested M1- and M2-type genes in Fluorescence Activated Cell Sorter (FACS)-sorted microglia/macrophages from WT mice were increased starting from 1 day after MCAO and further elevated by 3 days post-MCAO (data not shown). Within CX3CR1$^{-/-}$ microglia/macrophages, the M2-type genes (Ym1, Mcr1) were significantly increased, whereas the M1-type gene (iNOS) was notably decreased compared to WT microglia/macrophages when isolated at 72 hours after MCAO (FIG. 30 (E)). These results suggest that deficiency of CX3CR1 may facilitate the alternative activation (M2 state) of microglia/macrophages in stroke.

Example 43

Figure 31:
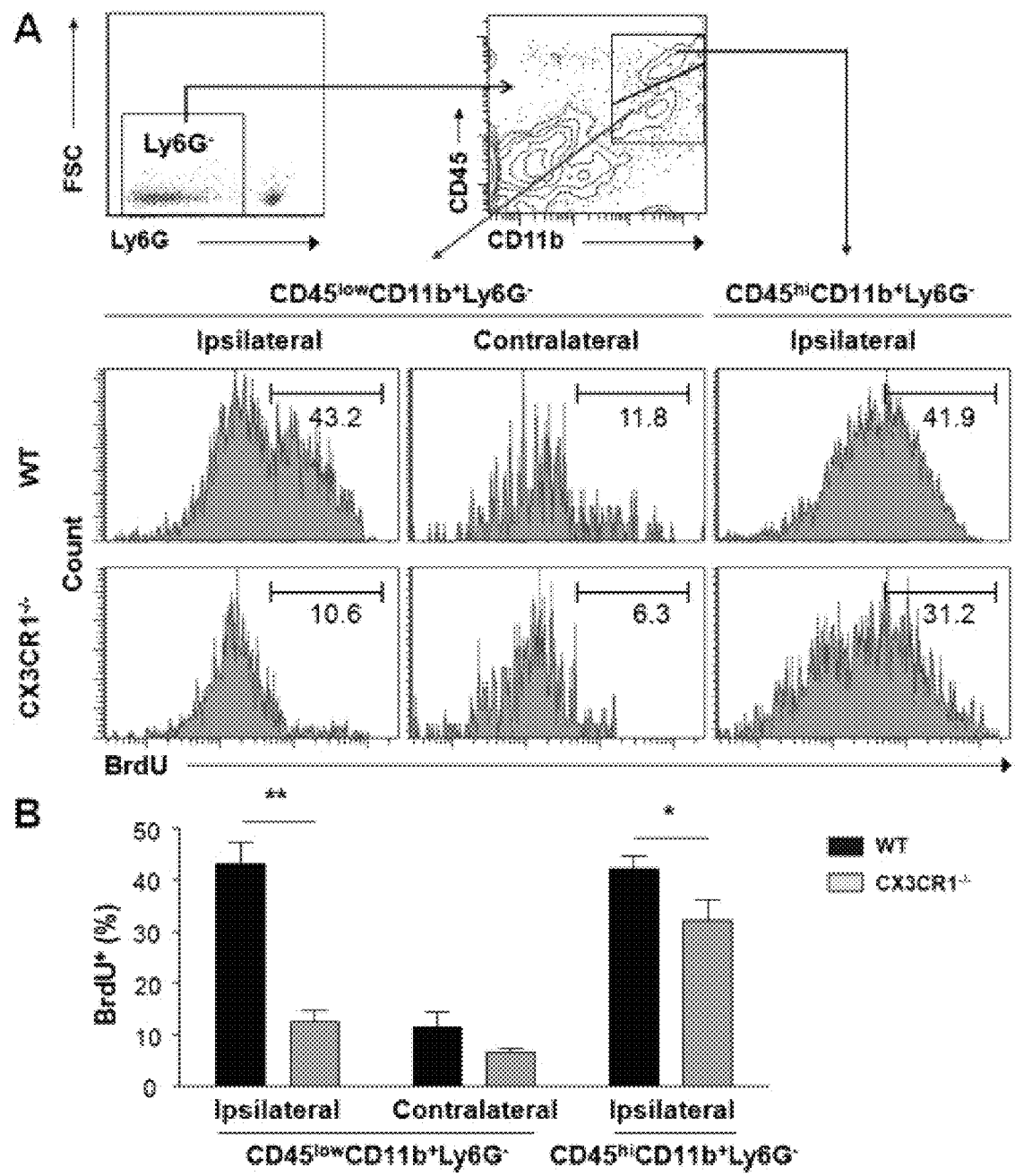
FIG. 31 depicts that suppressed proliferation of CD45$^{low}$/CD11b$^+$/Ly6G$^-$ and CD45$^{hi}$/CD11b$^+$/Ly6G$^-$ cells in the ipsilateral hemisphere of CX3CR1$^{-/-}$ mice after middle cerebral artery occlusion. (A) Flow cytometry analysis of proliferation of Ly6G$^-$ gated CD45$^{low}$/CD11b$^+$ (microglia) and CD45$^{hi}$/CD11b$^+$ (macrophages/activated microglia) population with 5-bromo-2-deoxyuridine (BrdU) incorporation in the ipsilateral hemisphere of wild-type (WT) and CX3CR1$^{-/-}$ mice 72 hours after middle cerebral artery occlusion (MCAO), compared to their contralateral (unlesioned) hemisphere controls. CD45$^{hi}$/CD11b$^+$/Ly6G$^-$ cell proliferation was not shown in the contralateral due to their very low to undetectable presence. (B) Graph presents quantification of microglia/macrophage proliferation measured by flow cytometry. Data indicate a marked reduction in CD45$^{low}$/CD11b$^+$/Ly6G$^-$ cell proliferation and a modest but significant reduction in CD45$^{hi}$/CD11b$^+$/Ly6G$^-$ cell proliferation in the ipsilateral hemisphere of CX3CR1$^{-/-}$ mice compared to WT mice 72 hours after MCAO. P<0.0001 for genotype and localization, P=0.0017 for interaction by two-way analysis of variance. *P<0.05, **P<0.01 by Bonferroni post-hoc tests. n=4 per group.

Reduced Proliferation of Macrophages and Microglia in Ipsilateral Hemisphere of CX3CR1$^{-/-}$ Mice after Middle Cerebral Artery Occlusion To determine whether the decrease in CD11b$^+$Ly6G$^-$ cells observed in ischemic lesions of CX3CR1$^{-/-}$ MCAO mice, in addition to decreased chemotaxis of monocytes, was due to suppressed expansion of microglia/macrophage, we assessed proliferation of CD11b$^+$Ly6G$^-$ cells. Proliferation analysis was performed on populations of CD45$^{low}$/CD11b$^+$/Ly6G$^-$ cells (microglia), and CD45$^{hi}$/CD11b$^+$/Ly6G$^-$ cells (macrophage/activated microglia) obtained from CX3CR1$^{-/-}$ and WT mice injected with BrdU (FIG. 31 (A)). Quantitative analysis revealed a significant 3-fold increase in the number of CD45$^{low}$/CD11b$^+$/Ly6G$^-$/BrdU$^+$ cells in the ipsilateral relative to the contralateral hemisphere in WT mice 72 hours after stroke (FIG. 31 (B)). A significant reduction (71.1%) in the number of proliferating CD45$^{low}$/CD11b$^+$/Ly6G$^-$ cells was observed in the ipsilateral hemisphere in CX3CR1$^{-/-}$ compared to WT mice (WT, 43.3±4.1%; CX3CR1$^{-/-}$, 12.5±2.2%, P<0.01, FIG. 31 (B)). There were no significant differences in the numbers of CD45$^{low}$/CD11b$^+$/Ly6G$^-$/BrdU$^+$ cells in the contralateral hemisphere between the two experimental groups, although CX3CR1$^{-/-}$ mice showed a lesser trend (WT, 11.5±2.9%; CX3CR1$^{-/-}$, 6.7±0.7%, P>0.05, FIG. 31 (B)). We also observed a modest but significant reduction (23.2%) in the number of proliferating CD45$^{hi}$/CD11b$^+$/Ly6G$^-$ cells in the ipsilateral hemisphere in CX3CR1$^{-/-}$ compared with WT mice (WT, 42.1±2.7%; CX3CR1$^{-/-}$, 32.3±3.9%, P<0.05). Collectively, these results indicate that CX3CR1 deficiency affects ischemic injury-induced proliferation of resident microglia and recruited macrophages.

Example 44

Figure 32:
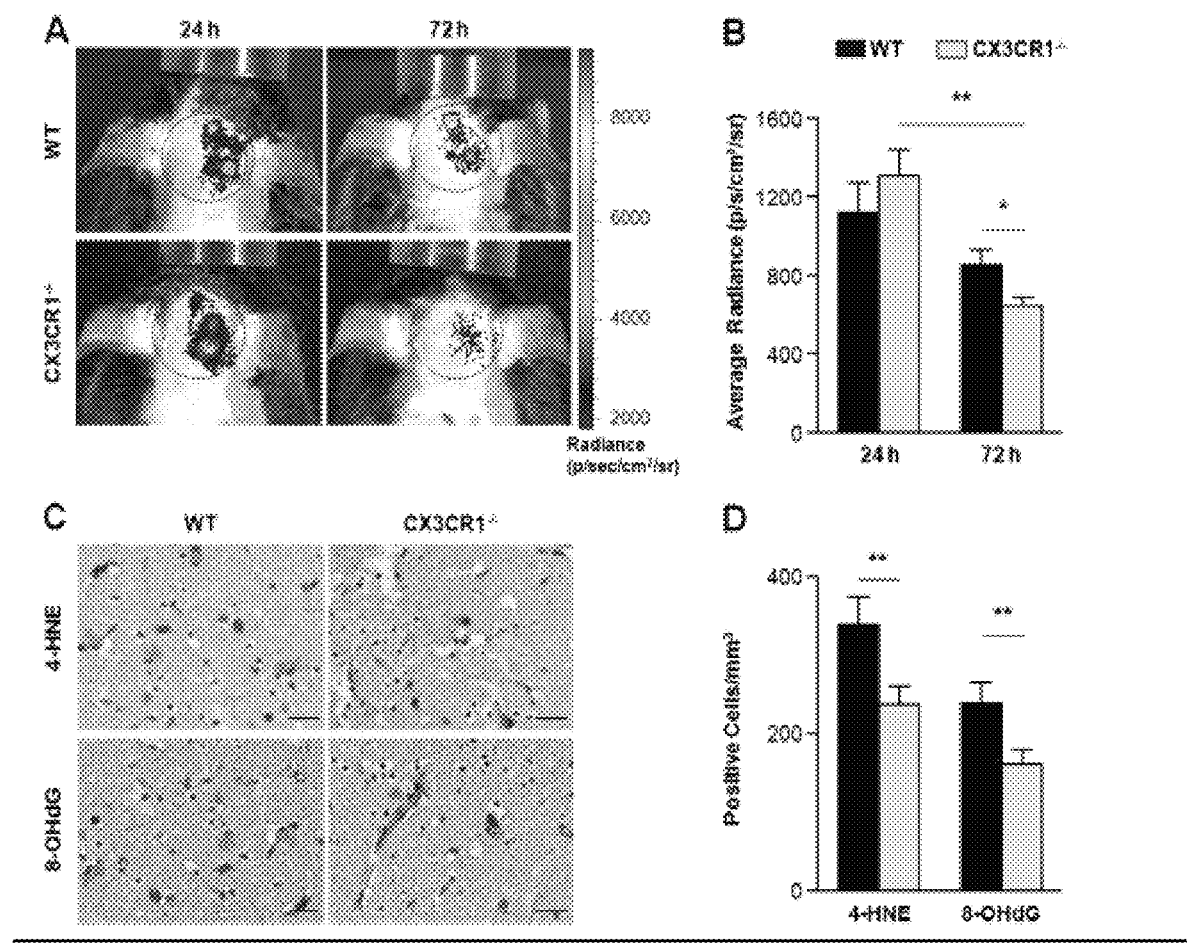
FIG. 32 depicts that CX3CR1 deficiency attenuates reactive oxygen species generation in brain after middle cerebral artery occlusion. (A) Reactive oxygen species (ROS) were evaluated by Xenogen IVIS200 imager in wild-type (WT) and CX3CR1$^{-/-}$ mice in vivo. (B) Quantification of ROS. No difference in ROS levels were observed between the two groups 24 hours after MCAO. ROS level decreased in CX3CR1$^{-/-}$ mice 72 hours after MCAO compared to 24 hours (P<0.0001 for genotype and time point, P=0.0036 for interaction by two-way analysis of variance; **P<0.01 by Bonferroni post-hoc tests) and is significantly less in CX3CR1$^{-/-}$ mice relative to WT mice (*P<0.05 by Bonferroni post-hoc tests). n=6 per group. p/s/cm$^2$/sr, photons per second per centimeter squared per steradian. (C) Immunohistochemistry for 4-hydroxy-2-nonenal (4-HNE) and 8-hydroxy-2-deoxyguanosine (8-OHdG) in the ischemic lesion 24 and 72 hours after MCAO. (D) Reduction of the number of stained cells in the CX3CR1$^{-/-}$ mice compared with WT mice. P<0.0001 for genotype, P=0.0003 for oxidative marker, and P=0.9827 for interaction by two-way analysis of variance. **P<0.01 by Bonferroni post-hoc tests. n=5 per group scale bars: 50 µm.

CX3CR1 Deficiency Attenuates Reactive Oxygen Species Generation in Brain after Middle Cerebral Artery Occlusion ROS, generated as by-products of cellular metabolism, have long been known to be a component of the inflammatory response after ischemia. To investigate whether CX3CR1 deficiency had effects upon ROS production, we assessed ROS levels in live mice using the Xenogen IVIS200 imager at 24 and 72 hours after MCAO. The chemiluminescence detection of ROS was performed in the brains, specifically in the ipsilateral hemisphere (FIG. 32 (A)). The mean chemiluminescence intensity of brain in WT mice was 1,090.3±127.4 p/s/cm$^2$/sr (photons per second per centimeter squared per steradian) at 24 hours and 850.9±81.7 p/s/cm$^2$/sr at 72 hours. Within CX3CR1$^{-/-}$ mice, mean chemiluminescence intensity values were 1,350.9±118.9 p/s/cm$^2$/sr at 24 hours and 641.7±47.6 p/s/cm$^2$/sr at 72 hours. At 24 hours post-ischemia, no differences in ROS levels were observed between the two groups (P>0.05). At 72 hours post-ischemia, the ROS levels decreased significantly in CX3CR1$^{-/-}$ mice compared to 24 hours (P<0.01), while no change was observed in WT mice (P>0.05) (FIG. 32 (B)). In addition, the oxidative impairment of neurons was immunohistochemically assessed by stain for lipid peroxidation with 4-HNE and damaged DNA with 8-OHdG (FIG. 32 (C)). The number of stained cells in the CX3CR1$^{-/-}$ mice was notably less compared with WT mice (P<0.01) (FIG. 32 (D)).

Example 45

Figure 33:
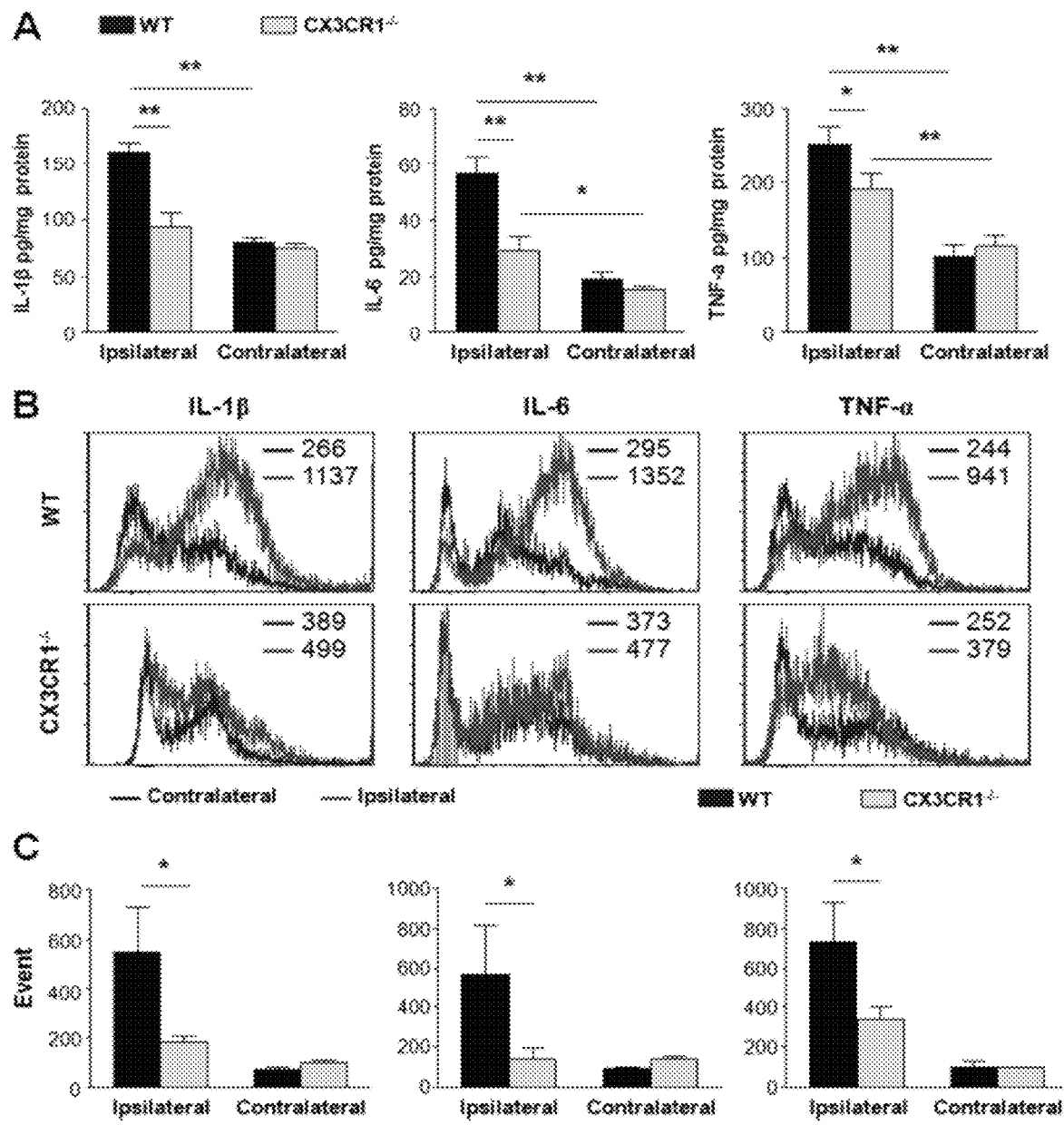
FIG. 33 depicts that CX3CR1 deficiency impairs inflammatory signaling in microglia and macrophage in ischemic brain. (A) The amounts of IL-1β, IL-6, and TNF-α in brain homogenates from wild-type (WT) and CX3CR1$^{-/-}$ mice 72 hours after middle cerebral artery occlusion (MCAO) were measured with ELISA. IL-1β: P=0.0018 for genotype, P=0.0002 for localization, and P=0.0052 for interaction by two-way analysis of variance; IL-6: P=0.0010 for genotype, P<0.0001 for localization, and P=0.0058 for interaction by two-way analysis of variance; TNF-α: P<0.0001 for genotype, P=0.0240 for localization, and P=0.0063 for interaction by two-way analysis of variance. *P<0.05, **P<0.01 by Bonferroni post-hoc tests. n=4 per group. (B) IL-1β, IL-6, and TNF-α expression were analyzed by flow cytometry within the CD11b$^+$Ly6G$^-$ gate. Representative histograms show IL-1β, IL-6, and TNF-α expression in the contralateral (blue) and ipsilateral (red) hemispheres of CX3CR1$^{-/-}$ and WT mice at 72 hours after MCAO. Mean fluorescent intensity is indicated within each representative histogram. (C) The number of IL-1β, IL-6, and TNF-α-producing CD11b$^+$Ly6G$^-$ cells was quantified from ischemic brain of CX3CR1$^{-/-}$ and WT mice at 72 hours after MCAO with flowcytometry. IL-1β$^+$/CD11b$^+$/Ly6G$^-$: P=0.0030 for genotype, P=0.0002 for localization, and P=0.0052 for interaction by two-way analysis of variance; IL-6$^+$/CD11b$^+$/Ly6G$^-$: P=0.0030 for genotype, P=0.0002 for localization, and P=0.0052 for interaction by two-way analysis of variance; TNF-α$^+$/CD11b$^+$/Ly6G$^-$: P=0.0386 for genotype, P=0.0332 for localization, and P=0.0173 for interaction by two-way analysis of variance. *P<0.05 by Bonferroni post-hoc tests. n=4 per group.

CX3CR1 Deficiency Impairs Inflammatory Signaling in Microglia and Macrophage in Ischemic Brain To determine whether CX3CR1 deficiency is associated with changes in the expression of inflammatory mediators produced by activated macrophages and microglia, ELISA was used to screen injured brain homogenates for differences in cytokine production. Consistent with previous reports, expression of a subset of inflammatory cytokines (IL-1β, IL-6, and TNF-α) was increased after MCAO regardless of genotype. In WT mice, the amounts of IL-10, IL-6, and TNF-α were 160.9±8.4, 56.5±6.1, 253.0±22.9 pg/mg in the ipsilateral hemisphere and 80.7±4.1, 19.2±2.2, 101.9±15.3 pg/mg in the contralateral hemisphere, respectively. In CX3CR1$^{-/-}$ mice, the amounts of IL-1β, IL-10, IL-6, and TNF-α were 94.2±11.9, 29.0±5.1, 191.9±19.8 pg/mg in the ipsilateral hemisphere and 74.5±5.1, 15.5±1.1, 116.5±13.7 pg/mg in the contralateral hemisphere, respectively. Notably, post-injury expressions of these cytokines were markedly reduced in CX3CR1$^{-/-}$ mice in the ipsilateral hemisphere, while no difference was observed in the contralateral hemisphere (FIG. 33 (A)).

To determine whether deficient CX3CR1 signaling in CNS microglia/macrophages could account for these cytokine expression changes, a series of controlled ex vivo flow cytometry assays were performed. Microglia and macrophages were isolated from ischemic brains of WT and CX3CR1$^{-/-}$ mice, followed by quantification of IL-1β$^+$/CD11b$^+$/Ly6G$^-$, IL-6$^+$/CD11b$^+$/Ly6G$^-$, and TNF-α$^+$/CD11b$^+$/Ly6G$^-$ cells using flow cytometry. Using this approach, an increased expression of IL-1β, IL-6, and TNF-α, in CD11b$^+$Ly6G$^-$ cells (fluorescent intensity in FIG. 33 (B)) as well as the numbers of cytokine-expressing CD11b$^+$Ly6G$^-$ cells (event quantification in FIG. 33 (C)) were detected 72 hours after MCAO in the ischemic lesions in WT mice (ipsilateral vs contralateral). This response was noticeably absent from the injured brain of CX3CR1$^{-/-}$ mice (FIGS. 33, (B) and (C)). In the ipsilateral hemisphere, CX3CR1$^{-/-}$ mice displayed significant reduction in expression of IL-1β, IL-6, and TNF-α in CD11b$^+$Ly6G$^-$ cells and cytokine-expressing CD11b$^+$Ly6G$^-$ cell numbers (P–0.05 vs WT, FIGS. 33, (B) and (C)).

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

The invention claimed is:

1. A method of reducing demyelination in a subject having multiple sclerosis, the method comprising the steps of:
   administering to the subject a therapeutically effective dosage of a composition comprising pertussis toxin (PTx) comprising subunits A and B wherein the therapeutically effective dosage is effective for reducing demyelination in the subject.

2. The method of claim 1, wherein the composition is administered intracerebroventricularly (icv) or intraperitoneally (ip).

3. The method of claim 1, wherein the therapeutically effective dosage is further effective at reducing inflammation in a spinal cord of the subject.

4. The method of claim 1, wherein the composition is administered to the subject in conjunction with a G-protein, chemokine and/or an adhesion blocking agent.

5. The method of claim 1, wherein the therapeutically effective dosage comprises at least 500 ng PTx.

6. The method of claim 1, wherein the therapeutically effective dosage comprises at least 1000 ng PTx.

7. The method of claim 1, wherein the therapeutically effective dosage comprises at least 2000 ng PTx.

8. The method of claim 1, wherein the therapeutically effective dosage comprises at least 3000 ng PTx.

9. The method of claim 1, wherein the therapeutically effective dosage is between 500 ng/day and 1000 ng/day PTx.

10. The method of claim 1, wherein the therapeutically effective dosage is between 1000 ng/day and 2000 ng/day PTx.

\* \* \* \* \*